United States Patent
Lee

(10) Patent No.: US 11,077,145 B2
(45) Date of Patent: Aug. 3, 2021

(54) METHOD FOR MASS PRODUCING PROTEINS IN MESENCHYMAL STEM CELLS

(71) Applicant: STEMMEDICARE CO., LTD., Seoul (KR)

(72) Inventor: Jang Ho Lee, Seoul (KR)

(73) Assignee: STEMMEDICARE CO., LTD., Seoul (KR)

( * ) Notice: Subject to any disclaimer, the term of this patent is extended or adjusted under 35 U.S.C. 154(b) by 486 days.

(21) Appl. No.: 15/562,382

(22) PCT Filed: Apr. 1, 2016

(86) PCT No.: PCT/KR2016/003421
§ 371 (c)(1),
(2) Date: Sep. 27, 2017

(87) PCT Pub. No.: WO2016/159721
PCT Pub. Date: Oct. 6, 2016

(65) Prior Publication Data
US 2018/0280441 A1    Oct. 4, 2018

(30) Foreign Application Priority Data

Apr. 3, 2015 (KR) .................. 10-2015-0047774

(51) Int. Cl.
| | | |
|---|---|---|
| *A61K 35/28* | (2015.01) | |
| *C07K 14/50* | (2006.01) | |
| *C07K 14/525* | (2006.01) | |
| *C07K 14/475* | (2006.01) | |
| *C07K 14/49* | (2006.01) | |
| *C07K 14/78* | (2006.01) | |
| *C07K 14/435* | (2006.01) | |
| *C07K 14/54* | (2006.01) | |
| *C12N 5/00* | (2006.01) | |
| *C07K 14/47* | (2006.01) | |
| *A61P 17/16* | (2006.01) | |
| *A61K 9/00* | (2006.01) | |
| *A61K 38/39* | (2006.01) | |
| *C07K 14/545* | (2006.01) | |

(52) U.S. Cl.
CPC ............ *A61K 35/28* (2013.01); *A61K 9/0014* (2013.01); *A61K 38/39* (2013.01); *A61P 17/16* (2018.01); *C07K 14/435* (2013.01); *C07K 14/47* (2013.01); *C07K 14/475* (2013.01); *C07K 14/49* (2013.01); *C07K 14/50* (2013.01); *C07K 14/525* (2013.01); *C07K 14/54* (2013.01); *C07K 14/545* (2013.01); *C07K 14/5409* (2013.01); *C07K 14/78* (2013.01); *C12N 5/00* (2013.01); *C12N 5/0031* (2013.01)

(58) Field of Classification Search
CPC ........ A61K 35/28; A61K 38/39; C07K 14/49; C07K 14/50; C07K 14/525
See application file for complete search history.

(56) References Cited

U.S. PATENT DOCUMENTS

| | | | | |
|---|---|---|---|---|
| 6,255,112 B1* | 7/2001 | Thiede | ............... | C12N 5/0643 424/93.21 |
| 2010/0196963 A1* | 8/2010 | Naughton | ............ | A61K 8/981 435/70.3 |
| 2011/0274670 A1* | 11/2011 | Nam | ................ | C07K 14/4753 424/93.21 |
| 2012/0141399 A1* | 6/2012 | You | ...................... | A61K 8/981 424/62 |
| 2014/0065240 A1* | 3/2014 | Mitsialis | ........... | A61K 38/1709 424/577 |

FOREIGN PATENT DOCUMENTS

| | | |
|---|---|---|
| KR | 10-2010-0105165 A | 9/2010 |
| KR | 10-2010-0105166 A | 9/2010 |

(Continued)

OTHER PUBLICATIONS

Yoon et al. "Secretory Profiles and Wound Healing Effects of Human Amniotic Fluid-Derived Mesenchymal Stem Cells" 2009 Stem Cells and Development, vol. 19, No. 6 (Year: 2009).*

Klein et al. "Amniotic and Placental Mesenchymal Stem Cell Isolation and Culture", in Mesenchymal Stem Cell Assays and Applications, 2011, Mehtods in Molecular Biology: Springer Protocols; pp. 75-88. (Year: 2011).*

Seung Ho Lee et al., "Paracrine Effects of Adipose-Derived Stem Cells on Keratinocytes and Dermal Fibroblasts", Annals of Dematology, vol. 24, No. 2, p. 136-143 (2012).

(Continued)

*Primary Examiner* — Teresa E Knight
(74) *Attorney, Agent, or Firm* — Novick, Kim & Lee, PLLC; Sang Ho Lee

(57) ABSTRACT

The present invention relates to the method for mass production of mesenchymal stem cell-derived proteins including various growth factors and cytokines, a mesenchymal stem cell conditioned medium containing a large amount of protein and produced by the above production method, cosmetic composition and pharmaceutical composition including the above conditioned medium for skin regeneration, anti-wrinkle, alopecia treatment, prevention of hair loss and promotion of hair growth. The method for mass production of the mesenchymal stem cell-derived protein of the present invention can greatly increase the amount of various growth factors and proteins which are known to be not expressed from mesenchymal stem cells or expressed only in very small amounts by the existing culture method, and the mesenchymal stem cell conditioned medium prepared by the above method contains a large amount of various kinds of cytokines and growth factors so that it has the excellent effect on skin regeneration, wrinkle improvement, prevention of hair loss, alopecia treatment and hair growth promotion.

4 Claims, 23 Drawing Sheets

(56) References Cited

FOREIGN PATENT DOCUMENTS

| KR | 10-2013-0006123 A | 1/2013 |
| WO | 2010/107285 A2 | 9/2010 |
| WO | 2010/107286 A2 | 9/2010 |
| WO | 2013/008960 A1 | 1/2013 |

OTHER PUBLICATIONS

D. Lee et al. "The hair growth-promoting effects of adipose tissue-derived stem cells", Journal of Investigative Dermatology. vol. 129, Suppl. 1, p. S99, 591 (2009).

Internet Material, Revive Organtech, Inc., "CRYO-GOLD, Chemically defined Slow Freezing Medium", Mar. 11, 2015.

Salazar, K. D. et al., "Mesenchymal Stem Cells Produce Wnt Isoforms and TGF-Beta1 that Mediate Proliferation and Procollagen Expression by Lung Fibroblasts", American Journal of Physiology-Lung Cellular and Molecular Physiology, 2009, vol. 297, No. 5, pp. L1002-L1011 (Sep. 4, 2009).

Revive Organtech, Inc., "Specification Sheet: CRYO-GOLD™, liquid, sterile-filtered, 100 mL". Mar. 30, 2015, pp. 1-3, Irvine CA, USA. Accessed on Oct. 4, 2018 "http://assets.stemgent.com/files/1441/original/Specification-10003-01-CRYO-GOLD-100%20mL-3.22.2015.pdf".

Sarah Tzu-Feng Hsiao et al: "Comparative Analysis of Paracrine Factor Expression in Human Adult IVIesenchymal Stern Cells Derived from Bone Narrow, Adipöse, and Dermal Tissue". Stem Gells and Development, Aug. 10, 2012, pp. 2189-2203, vol. 21, No. 12, Mary Ann Liebert, Inc.

Irene Ginis et al "Evaluation of Bone Marrow-Derived Mesenchymal Stem Cells After Cryopreservation and Hypothermie Storage in Clinically Safe Medium". Tissue Engineering: Part C, Method Dec. 2008. Jun. 1, 2012, pp. 453-463, vol. 18, No. 6, Mary Ann Liebert, Inc.

\* cited by examiner

HAIR FOLLICLE CONDITION OF MICE ON THE 4TH DAY

G1: DISTILLED WATER CONTROL,
G2: PLACEBO CONTROL, G3: TEST SUBSTANCE,
G4: POSITIVE CONTROL (5 % MINOXIDIL)

HAIR FOLLICLE CONDITION OF MICE ON THE 8TH DAY

G1: DISTILLED WATER CONTROL,
G2: PLACEBO CONTROL, G3: TEST SUBSTANCE,
G4: POSITIVE CONTROL (5 % MINOXIDIL)

G1: DISTILLED WATER CONTROL,
G2: PLACEBO CONTROL, G3: TEST SUBSTANCE,
G4: POSITIVE CONTROL (5 % MINOXIDIL)

HAIR FOLLICLE CONDITION OF MICE ON THE 13TH DAY

G1: DISTILLED WATER CONTROL,
G2: PLACEBO CONTROL, G3: TEST SUBSTANCE,
G4: POSITIVE CONTROL (5 % MINOXIDIL)

G1: DISTILLED WATER CONTROL,
G2: PLACEBO CONTROL, G3: TEST SUBSTANCE,
G4: POSITIVE CONTROL (5 % MINOXIDIL)

METHOD FOR MASS PRODUCING PROTEINS IN MESENCHYMAL STEM CELLS

TECHNICAL FIELD

The present invention relates to a method for mass production of mesenchymal stem cell-derived proteins, including various growth factors and cytokines, mesenchymal stem cell conditioned medium containing a large amount of protein produced by the production method, and the cosmetic composition for skin regeneration, anti-wrinkle, alopecia treatment, prevention of hair loss and promotion of hair growth and pharmaceutical composition for skin regeneration including the above conditioned medium

BACKGROUND ART

The cell therapy product is defined as the medicine for cure, diagnosis and prevention of diseases through more-than-minimal manipulation including in vitro proliferation, isolation or other methods changing biological properties of autologous, allogeneic or xenogeneic cells to restore the functions of cells and tissues. The stem cell therapy product is defined as specific cell therapy product including stem cells and is being actively developed as the medicine for the disease to which recovery and regeneration of lost cells is essential and is difficult to be cured naturally such as neurological diseases, heart diseases, lung diseases, liver diseases and cancer.

Stem cell has multipotency and ability to differentiate into specific cells and thus they have a great potential as a cell therapy production. However, to the date, survival rate after transplantation is not high and can cause immune rejection reaction, and it is difficult to find examples that have achieved such wide and stable clinical application.

As an alternative to the stem cell therapy product, the conditioned medium of the stem cells has been attracting attention.

The term "stem cell conditioned medium" refers to a medium that does not contain the obtained cells after culturing the cells, and includes various components essential for cell growth (ex, cytokines, growth factors and so on). The stem cell conditioned medium is used for promoting cell growth or for separating a specific component. In addition, the stem cell conditioned medium itself has been applied to the treatment of various diseases. For example, it is reported that the mesenchymal stem cell conditioned medium can be applied to the treatment of acute liver disease using the effect of inhibiting the death of hepatocytes and increasing the regeneration of hepatocytes. It is reported that the conditioned medium of mesenchymal stem cell derived from human amniotic fluid contains growth factors and proteins effective for regeneration and wound healing and promotes wound healing when applied to wound sites. In addition, it is reported that adipose-derived mesenchymal stem cells secrete genes and growth factors involved in blood vessel and cell regeneration, and hepatocyte-like cells differentiated from human embryonic stem cells and proteins secreted from these cells were treated with mouse and then restored liver damage.

However, since the medium used in the above studies contains bovine serum which is an animal-derived component, and buffer solution and indicator components which are poor in safety, it is difficult to apply directly to the clinical applications. In addition, in the case of the conventional cell culture method, there is a problem that the low concentration of the components secreted by the stem cell (for example, growth factors, etc.) thus large amount of stem cell conditioned medium is required in the clinical application and so, production cost for additional process including concentration increases remarkably and the economic efficiency is lowered. Various attempts have been made to overcome these problems, but no satisfactory results have been reported to date. For example, there have been reports of culturing stem cells under hypoxic condition for the purpose of increasing the content of a specific growth factor such as VEGF, but the yield has been limited. In addition, when serum-free medium is used to exclude bovine serum, it is difficult to maintain the stemness of the stem cells, resulting decreasing of physiological activities of the stem cell conditioned medium and so, can be obtained only once.

DISCLOSURE

Technical Problem

In order to solve this problem, the inventors developed a mesenchymal stem cell culture method that can produce large amounts of various growth factors and proteins rather than conventional cell culture method that expression no or small amount of growth factors and proteins in the stem cell conditioned medium. Further, the above culture method establishes optimized culture condition that increase the content of a useful protein containing growth factors through changing various culture conditions in a serum-free culture instead of subjecting the cell itself to an artificial manipulation in order to increase the content of specific growth factor. So, the mesenchymal stem cell conditioned medium produced by this method is expected to be very useful for human skin regeneration, anti-wrinkle, alopecia treatment, prevention of hair loss, and promotion of hair growth.

Technical Solution

The present invention is directed to provide a method for mass production of mesenchymal stem cell-derived proteins including various growth factors and cytokines, a mesenchymal stem cell conditioned medium containing a large amount of protein produced by the above production method, and cosmetic and pharmaceutical composition including the above conditioned medium for skin regeneration, anti-wrinkle, alopecia treatment, prevention of hair loss, and promotion of hair growth.

Advantageous Effects

In the present invention, the mass production method of the mesenchymal stem cell-derived proteins remarkably increases the kind and amount of the protein secreted from the mesenchymal stem cells compared to the conventional method. In particular, the mesenchymal stem cell conditioned medium produced by the above method contains a large amount of cytokines, growth factors and a large amount of collagen which is a major constituent of the skin, and it is an excellent effect on activating the collagen production. Therefore, it exerts an excellent effect on skin regeneration, anti-wrinkle, alopecia treatment, prevention of hair loss, and promotion of hair growth.

BEST MODE

Figure 1:
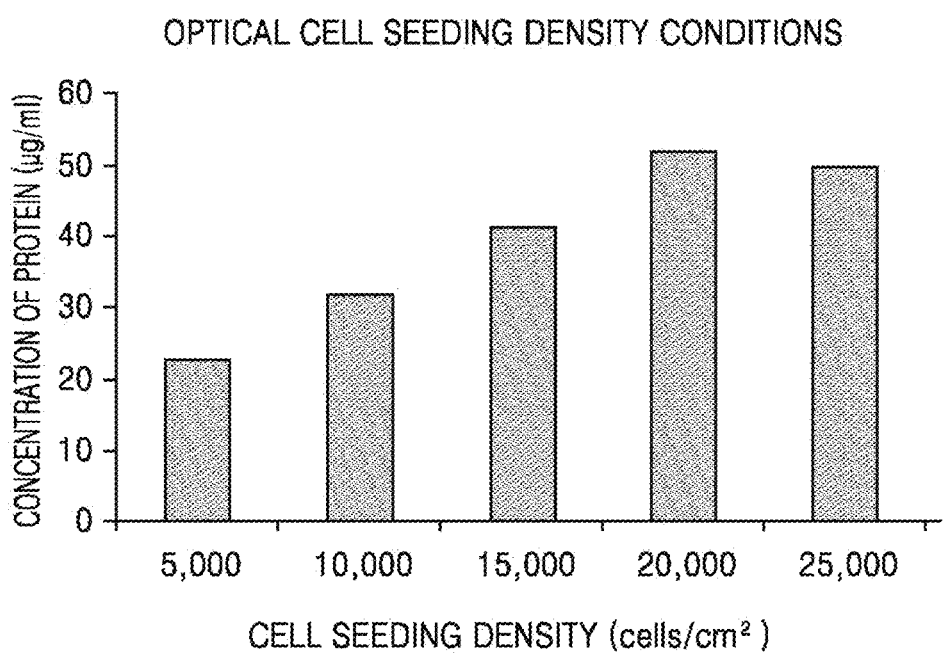
FIG. 1 shows the optimal cell seeding density conditions for the production of stem cell secretory proteins.

To accomplish the above objects, as one form, this invention provides a method for culturing a mesenchymal stem cell, comprising: (a) inoculating mesenchymal stem cells at a density of 18,000 to 22,000 cells/cm$^2$; (b) culturing the mesenchymal stem cells in a serum-free medium; and (c) obtaining a stem cell conditioned medium after 114 to 126 hours of culturing, and herein the above mesenchymal stem cells is stored in a deep-freezer with CRYO-GOLD freezing solution at a temperature of −90 to −70° C., and the above proteins may contain AR, bFGF, BMP-5, BMP-7, GH, IGFBP-1, IGFBP-2, IGFBP-3, IGFBP-4, SCF, TGF α, TGF β1, VEGF R3, VEGF D, ICAM-1, IL-1a, IL-5, MIP-1a, MIP-b, MIP-d, RANTES, TNF R1 and TNF RII The present inventors have optimized stem cell culture methods for mass production of useful proteins such as cytokines and growth factors from the stem cell conditioned medium. The stem cell culture medium obtained from the above optimized stem cell culture method contains a large amount of useful protein. In particular, it has a high level of collagen, and it has been confirmed that it enhances collagen synthesis in human fibroblast and exhibits excellent wound healing activity.

Hereinafter, each step of the mass production method of the mesenchymal stem cell-derived protein will be described in detail.

Step (a) is a step of inoculating the mesenchymal stem cells with an appropriate number of doses, in particular, inoculating at a density of 18,000 to 22,000 cells/cm$^2$.

In the present invention, the term "stem cell" refers to a cell having an ability to differentiate into various cells through suitable environment and stimulation, and having a self-renewal capacity.

The stem cells used in the present invention are not limited as long as they are capable of differentiating and self-renewal ability. Preferably, the stem cells may be mesenchymal stem cells, more preferably human fat-derived, umbilical code-derived, bone marrow-derived, amniotic fluid-derived or amnion-derived mesenchymal stem cells. Most preferably the stem cells may be amniotic fluid-derived mesenchymal stem cells.

In the present invention, the term "mesenchymal stem cell (MSC)" as used herein refers to a cell as the origins that can make cartilage, bone, fat, bone marrow, muscle, nerve and so on, and is present in umbilical code, peripheral blood, fat, amniotic fluid, and the other organs, in general, bone marrow in the case of an adult, and means mesenchymal stem cells obtained therefrom but is not particularly limited according to the origin thereof.

Mesenchymal stem cells may undergo different behaviors such as cell division, differentiation or migration depending on the surrounding microenvironment (stem cell niche) in vivo. More specifically, the mesenchymal stem cells may show different gene expression by the stimulation from the surrounding microenvironment, and thus the type and amount of secreted protein may vary. Such surrounding microenvironment includes not only the physical environment around the cell, that is, the characteristics of the tissue in which the cell is present, the location of the cell and the attachment state, but also a chemical environment, for example, the external cytokines or growth factors.

This tendency is similar to that observed in in vitro stem cell culture. Accordingly, the types and amounts of the proteins secreted from the stem cells can be changed by changing the conditions for culturing the stem cells.

The in vitro culture of stem cells includes a step of inoculating the stored stem cells, primary cultured cells or subcultured cells into a culture vessel, and density of the inoculating cells induces the change of the type and amount of proteins secreted from stem cells. This is because the gene expression patterns of stem cells are directly or indirectly affected by cell-cell interactions.

In the present invention the inoculated density of the cells may be 18,000 to 22,000 cells/cm$^2$, preferably 19,000 to 20,000 cells/cm$^2$, and more preferably 20,000 cells/cm$^2$.

In one specific example of the present invention, the mesenchymal stem cells were inoculated at a density of 5,000 to 25,000 cells/cm$^2$ and examine the concentration of the secreted protein. As a result, it was confirmed that the highest concentration of the protein was shown at a density of 20,000 cells/cm$^2$. (FIG. 1)

Especially, at 25,000 cells/cm$^2$, it was confirmed that the protein concentration was lower even though the cell number was higher. Therefore, it was found that the optimal cell density for mass production of mesenchymal stem cell-derived proteins was about 20,000 cells/cm$^2$.

Next, step (b) is a step of culturing mesenchymal stem cells in a serum-free medium.

In the present invention, the term "culture medium" as used herein refers to a culture medium capable of supporting the growth and survival of stem cells in vitro and it contained all ordinary culture medium generally used in stem cell culture. Depending on the type of cells, culture medium and culture conditions can be selected, appropriately. The medium used for the culture is preferably a cell culture minimum medium (CCMM), and generally includes carbon sources, nitrogen sources and trace element components. The medium may include, for example, DMEM (Dulbecco's Modified Eagle's Medium), MEM (Minimal Essential Medium), BME (Basal Medium Eagle), RPMI1640, F-10, F-12, α-MEM (α-Minimal essential Medium), GMEM (Glasgow's Minimal Essential Medium), and IMEM (Iscove's Modified Dulbecco's Medium), and so on, but they are not limited thereto. The culture medium may also contain antibiotics such as penicillin, streptomycin, or gentamicin.

Particularly, in the present invention, the medium is characterized by being serum-free medium. Serum is generally added to the culture medium when cells culture in vitro. In case serum is not added, the cell cycle arrest in which the cell cycle stays in the G0 phase may occur. If this state is maintained, senescence may proceed or apoptosis may occur. On the other hand, when serum is added, the cells can be continuously proliferated.

Because it is practically difficult to obtain a large amount of human serum, in vitro culture uses mainly animal serum such as fetal bovine, horse, donkey, and so on. Serum contains a variety of cytokines and growth factors to allow cell proliferation, but serum components are not yet fully understood. Therefore, since the animal-derived serum has a risk of causing an immune response or becoming a causative factor of a specific disease, the possibility of adverse effects on the application of cells or cell culture medium cultured in culture medium containing the animal-derived serum is constantly pointed out, and make it difficult to proceed with clinical practice.

Accordingly, the present invention has developed the method for mass production method of mesenchymal stem cell-derived proteins, including mesenchymal stem cell culture in a serum-free culture medium to obtain the safe cell conditioned medium for application to human.

Step (c) is a step of culturing the mesenchymal stem cells in the serum-free culture medium to obtain a stem cell conditioned medium during 114 to 126 hours.

As the above description, the type and amount of the proteins secreted by the external stimuli during the culturing process may vary, and factors influencing the external stimuli include the culturing time. That is, the type and amount of proteins secreted from stem cells can be changed according to the passage of time, and the content of proteins present in the culture medium can be changed. Therefore, the inventors of the present invention established optimal time conditions for mass production of protein through comparing the amount of protein produced in the conditioned medium according to different culture time conditions of stem cells.

In the present invention, the optimum time for culturing stem cells to obtain a stem cell conditioned medium may be from 114 to 126 hours, preferably from 117 to 123 hours, and more preferably from 120 hours.

Figure 2:
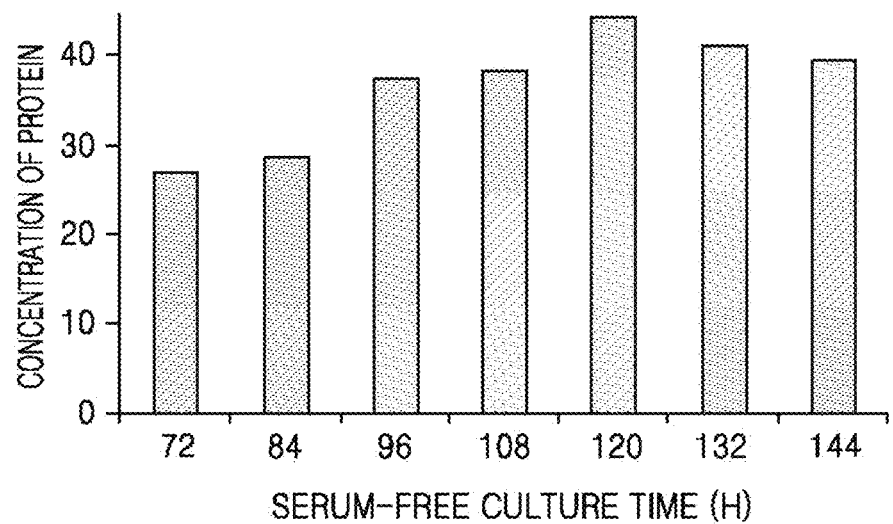
FIG. 2 shows the comparison of protein production according to the serum-free culture time (every 12 hours).

In one specific example of the present invention, the mesenchymal stem cells were cultured in serum-free medium for 72 to 144 hours and the protein yields at each time condition were compared (FIG. 2). As a result, it was verified that protein production is maximized in the conditioned medium of mesenchymal stem cell cultured during about 120 hours.

In the step of obtaining the above conditioned medium, the conditioned medium containing proteins produced from mesenchymal stem cells is collected from a culture vessel. After obtaining the above conditioned medium once, the stem cell conditioned medium can be obtained in addition during 114 to 126 hours culture after the cells are washed with the buffer solution and replaced with the fresh culture medium. The process for obtaining the stem cell conditioned medium like this may be repeated several times, preferably 1 to 3 times, but is not limited thereto.

Figure 5:
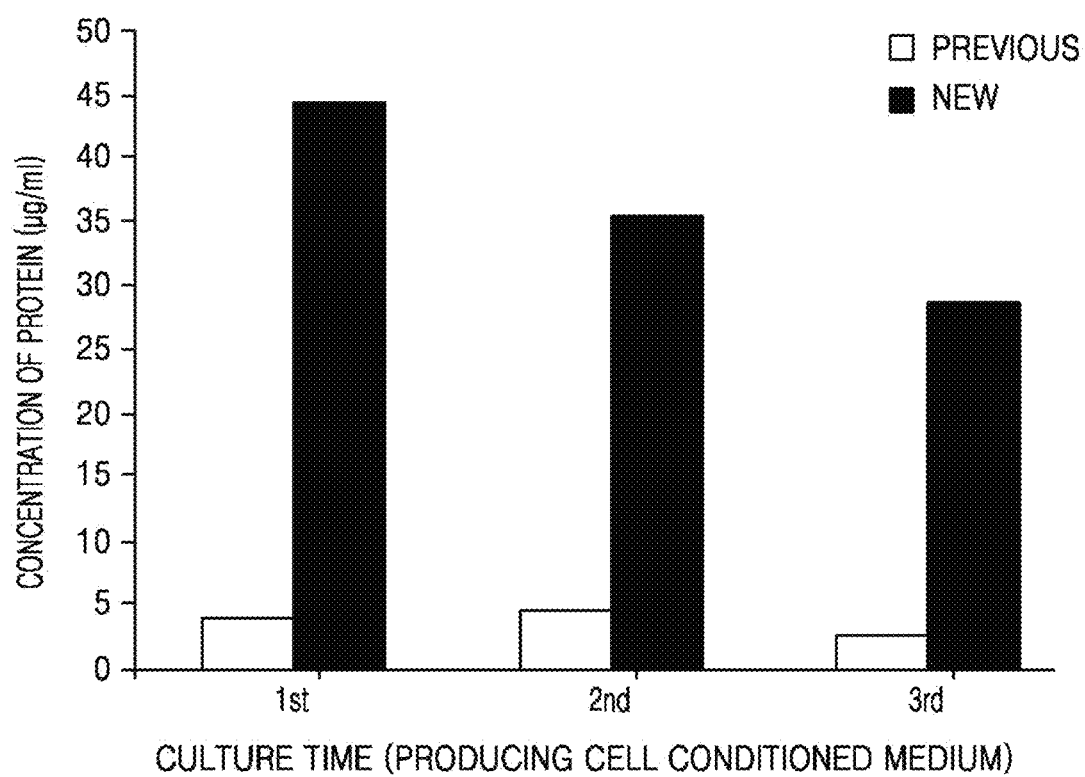
FIG. 5 shows the comparison of the total amount of proteins of the stem cell conditioned medium under both optimal serum-free culture and cryopreservation conditions.

In one specific example of the present invention, the stem cell conditioned medium produced by mass production method of the mesenchymal stem cell-derived protein of the present invention was obtained 3 times in succession, and protein concentration of the conditioned medium was verified. As a result, the protein concentration was slightly decreased as the number of obtain is increased, but it was verified that these stem cell conditioned medium contained a significantly larger amount of protein than the mesenchymal stem cell conditioned medium cultured by the conventional method (FIG. 5). Thus, it can be shown that this process can be repeated several times during the mesenchymal stem cells culture.

The method for mass production of the mesenchymal stem cell-derived protein is characterized in that the mesenchymal stem cells are stored in a CRYO-GOLD solution in a deep freezer at −90 to −70° C.

In case of culturing cells in vitro, the process of storing the cells may be necessary unless the cells cultured through the primary culture are used immediately. Stem cells are self-renewing cells that can infinitely proliferate, but since the in vitro culture is an artificially created environment, the cells can undergo ageing or apoptosis during long-term culture except for some cells including cancer cells and embryonic stem cells. In case of mesenchymal stem cells, there is a limit in subculture times. In addition, since cell culture requires a lot of cost and manpower, it is very important to store the cells in the cell culture process so that the cells can be cultured when necessary.

Cells are stored at a cryogenic temperature generally mixed with a freezing solution. The freezing solution serves to prevent cell membranes from being destroyed by crystallization when cells are frozen. Also, the cell freezing temperature can be important, and cells can be stored in a $LN_2$ (liquid nitrogen) tank at −196° C. or in a cryogenic freezer at higher temperature than $LN_2$ tank.

Figure 3:
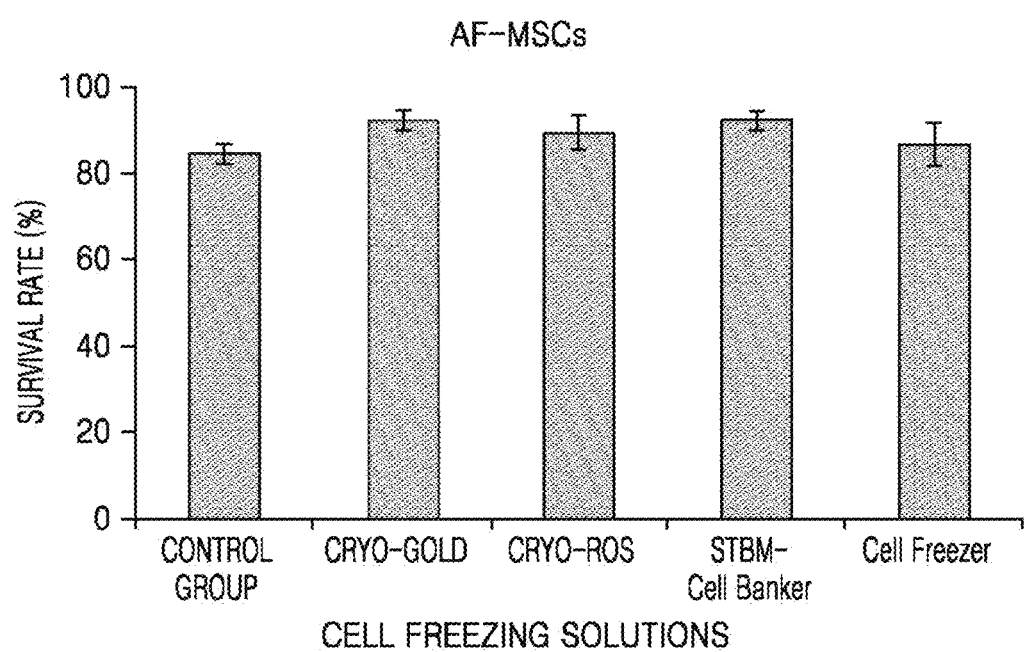
FIG. 3 shows the comparison of the cell survival rate of mesenchymal stem cells according to the cryopreservation conditions.
Figure 4:
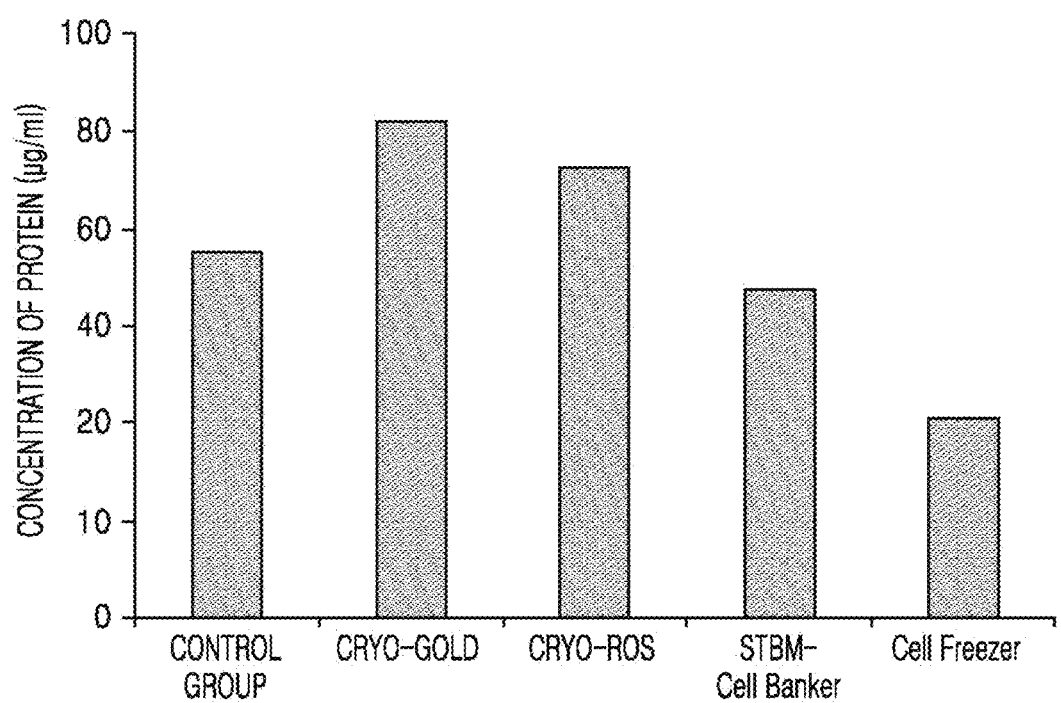
FIG. 4 shows the comparison of the secretory proteins of stem cells according to the type of cell freezing solution.

In one specific example of the present invention, the productivity of stem cell secretory proteins according to the kinds of freezing solution was confirmed at the stage of storing the mesenchymal stem cells. The viability of cells that were cryopreserved in the control group (containing 10% DMSO, 20% FBS and 70% cDMEM), CRYO-GOLD, CRYO-ROS, STEM-CELL BANKER and CellFreezer was confirmed, but there are no difference (FIG. 3). However, as a result of confirming the protein concentration of the conditioned medium of the above cells, it was confirmed that when the CRYO-GOLD solution was used as a freezing solution, the protein concentration was the highest. Thus, it was found that freezing storage of cells with CRYO-GOLD solution is the optimal condition for mass production of proteins from stem cells (FIG. 4)

In another specific example of the present invention, the concentrations of protein in human amniotic fluid-derived mesenchymal stem cell culture medium produced under optimized culture conditions or conventional culture conditions were examined. As a result, protein concentration was remarkably increased in optimized culture conditions (FIG. 5). This result for mesenchymal stem cells derived from amniotic fluid (FIG. 20) was similarly shown in cases of bone marrow (FIG. 21), umbilical cord (FIG. 22), and amniotic membrane (FIG. 23). Therefore, the mass production method of the mesenchymal stem cell-derived protein in the present invention can be applied regardless of the origin tissues of mesenchymal stem cells. Using above method, a variety of proteins including useful growth factors and cytokines in mesenchymal stem cells can be produced in large quantities.

The present invention object is mass production of proteins containing growth factors by culturing mesenchymal stem cells. The above proteins may increase the amount of a protein known to be secreted from mesenchymal stem cells, or may be newly secreted by the above method although it is not known to be secreted from them in the past.

Specifically, the proteins produced by the mass production method of the mesenchymal stem cell-derived proteins of the present invention contain AR, bFGF, BMP-5, BMP-7, GH, IGFBP-1, IGFBP-2, IGFBP-3, IGFBP-4, SCF, TGFα, TGFβ1, VEGF R3, VEGF-D, ICAM-1, IL-1a, IL-5, MIP-1a, MIP-b, MIP-d, RANTES, TNF R1 or TNF RII.

In addition, the stem cell conditioned medium produced by the mass production method of the mesenchymal stem cell-derived protein of the present invention may further include BDNF, BMP-4, b-NGF, EGF R, FGF-4, FGF-7, GDF-15, GDNF, HGF, IGFBP-6, IGF-I, Insulin, MCSF R, NGF R, NT-3, NT-4, OPG, PDGF-AA, PlGF, SCF R, VEGF, G-CSF, IL-2, IL-6, IL-8, IL-11, MCP-1, MCSF, MIG, TIMP-1, TIMP-2, TNFα, or TNFβ.

In the present invention, the term "FGF-7" (Fibroblast growth factor 7) belongs to the FGF family and plays an important role in embryonic development, cell proliferation, or cell differentiation. It is necessary for normal tissue formation and serves as a growth factor for keratinocytes and is a major factor for normal epithelial cell proliferation.

It is also known to play an important role in epithelialization, re-epithelialization of the wound, hair development, or lung organ formation.

In the present invention, the term "IGFBP-1" (insulin-like growth factor-binding protein 1) is the insulin-like growth factor binding protein that prolongs the half-life of IGF and inhibits or stimulates the growth promoting effect of IGF in cell culture. It is also known to promote cell migration.

In the present invention, the term "IGFBP-3" (insulin-like growth factor-binding protein 3) is insulin-like growth factor binding proteins that binds with IGFALS (insulin-like growth factor-binding protein 3) circulates plasma, prolongs the half-life of IGF and stimulates the growth promoting effect in cell culture. However, protein levels decrease during progression of prostate cancer and the like.

In the present invention, the term "MCSF-R" (Macrophage colony-stimulating factor receptor) is a receptor for MCSF which affects hematopoietic stem cells to differentiate into macrophages or other related cells, is produced in response to viral infection of eukaryotic cell, and is associated with placental development.

In the present invention, the term "NT-4" (Neurotrophin-4) is a neurotrophic factor and known to be a factor necessary for the survival of peripheral sensory sympathetic nerves by using the TrkB receptor tyrosine kinase as a receptor.

In the present invention, the term "TGF-β1" (Transforming growth factor-β1) is a protein having a complex function of regulating several growth factors both positively and negatively, and regulating cell proliferation, differentiation and various functions for many cell types.

It plays an important role in bone remodeling by stimulating osteoblast derived bone formation and s in wound healing.

It is also important for regulation of immune system and is known to be secreted from most immune cells.

In the present invention, the term "bFGF" (basic fibroblast growth factor 2) plays an important role in regulation of cell survival, cell division, angiogenesis, cell differentiation, cell migration, and wound healing.

In the present invention, the term "EGF-R" (epidermal growth factor receptor) is an epithelial growth factor receptor and tyrosine kinase.

In the present invention, the term "FGF-4" (Fibroblast growth factor 4) belongs to the FGF family and plays an important role in embryonic development, cell proliferation, or cell differentiation. It acts as a developmental protein, growth factor, mitogen, and is a protein necessary for normal limb and heart valve development during embryonic development.

In the present invention, the term "GDF-15" (growth/differentiation factor 15) belongs to the TGF-superfamily and is also known as TGF-PL, MIC-1, PDF, PLAB and PTGFB. It plays a role in regulation of inflammatory and apoptotic pathways during disease processes in damaged tissues.

In the present invention, the term "HGF" (Hepatocyte growth factor) is a hepatocyte growth factor and secreted from various kinds of mesenchymal cells. It plays a role in cell proliferation promoting activity, cell motility promoting activity, and epithelial morphogenesis inducing activity, and acts as neurotrophic factor and angiogenic factor. It is also involved in the formation of internal organs such as the liver, kidney, lung and so on, placenta, and skeletal system as a mediator of epithelial-mesenchymal interactions during development stage. In the adult body, it is expected to be a therapeutic agent for long-term diseases by functioning as an organ regenerative factor promoting the regeneration of liver, kidney, lung, and digestive tract.

In the present invention, the term "IGFBP-4" (insulin-like growth factor-binding protein 4) is circulating in the plasma in the glycosylated or unglycosylated forms by binding with IGF and prolongs the half-life of IGF. And it acts to inhibit or stimulate the growth promoting effect of IGF in cell culture. It is also known to acts as a cell death factor for various cancer cells in vivo and in vitro, thereby reducing the proliferation of cancers such as prostate cancer and colorectal cancer.

In the present invention, the term "IGFBP-6" (IGFBP-6) acts to inhibit or stimulate the growth promoting effect of IGF in cell culture by interaction and binding with IGF to its cell surface receptor to prolong the half-life of IGF.

In the present invention, the term "NT-3" (Neurotrophin-3) is a neurotrophin that is particularly present in brain and peripheral tissues and is a protein that contributes to promoting and controlling neurogenesis. It also promotes the survival of visceral sensory neurons and proprioceptive sensory neurons. It is known to have the characteristic of being expressed together with FGF5, TGF-1 and so on in the catagen of hair cycle.

In the present invention, the term "OPG" (Tumor necrosis factor receptor superfamily member 11B) is also known to osteoprotegerin (OPG) and osteocalostatic inhibitory factor (OCIF). It plays a role in offsetting bone destruction (osteoclastogenesis). It inhibits the activity of osteoclasts and promotes osteoclast cell death in vitro. Bone homeostasis depends on the local ratio between TNSF11 and TNFRSF11B. It is also known to prevent arterial calcification.

In the present invention, the term "PDGF-AA" (Platelet-derived growth factor subunit A) is a growth factor that plays an important role in regulation of fetal development, cell proliferation, cell migration, survival, and chemotaxis. It acts as a mitogen for mesenchymal cells and plays an important role in wound healing.

In the present invention, the term "PlGF" (placenta growth factor) is a placental growth factor that acts on stimulation and activation of neovascularization, endothelial cell growth, proliferation and migration.

In the present invention, the term "VEGF" (Vascular endothelial growth factor A) is known to act as a developmental protein, a growth factor, and a mitogen to activate neovascularization, angiogenesis, and endothelial cell growth. It also induces endothelial cell proliferation, promotes cell migration, inhibits apoptosis, and promotes vascular permeability.

In the present invention, the term "G-CSF" (Granulocyte-colony stimulating factor) acts as a granulocyte colony stimulating factor receptor to form a bone and to smooth blood circulation. It is also known to promote leukocyte production, differentiate tissues, regulate inflammatory cytokine regulatory signal JAK, and promote the activity of other cytokines (STAT, MAPK, PI3K, and Akt).

In the present invention, the term "ICAM-1" (Intercellular Adhesion Molecule 1) is a kind of inflammatory protein involved in adhesion and migration of inflammatory cells as intercellular adhesion molecules. It induces structural changes in the inner blood vessels and transforms the immune system cells.

In the present invention, the term "IL-6" (Interleukin 6) induces final differentiation of beta cells into antibody producing cells, and serves as muscle cells and forms bone marrow cells. It is known to prevent infection and resist bacteria.

In the present invention, the term "IL-11" (Interleukin 11) is a fibroblast of bone marrow and has a variety of biological activities, affecting proliferation of blood cell lines, differentiation of B lymphocytes, proliferation and differentiation of hematopoietic stem cells, proliferation and maturation of megakaryocytes, acting on hematopoietic system, and affecting skeleton and nervous system.

In the present invention, the term "MCP-1" (monocyte chemoattractant protein-1) selectively induces monocytes, lymphocytes, basophils, and the like as a CC chemokine. It is also produced in stromal cells, glomerular endothelial cells, tubular epithelial cells, capillary endothelial cells and smooth muscle cells in response to IL-1a, TNF-a, low-density lipoprotein (LDL) and so on. It is also known to play an important role in the pathophysiology of inflammatory renal disease from the infiltration of monocytes and polynuclear cells.

In the present invention, the term "MIP-1a" (macrophage inflammatory protein 1 alpha) is a member of CC chemokine or beta subfamily and is known to act as a chemoattractant for various cells such as MIP-1 alpha monocytes, T cells, and B cells.

In the present invention, the term "TIMP-1" (TIMP metallopeptidase inhibitor 1) is a constitutive genetic element of TIMP and a constitutive protein. It acts as an inhibitor of MMPs and is known to function to prevent apoptosis.

In the present invention, the term "TIMP-2" (TIMP metallopeptidase inhibitor 2) is a constitutive genetic element of TIMP and is known to modulate melanocyte by MITF.

In the present invention, the term "TNF RI" (Tumor necrosis factor—and TNF receptor I) is a tumor necrosis factor receptor that is a protein produced in the body by macrophages. TNF-related cytokines are associated with autoimmune diseases and are known to stimulate T cells in particular.

These above proteins were not secreted or secreted in a very small amount by the conventional mesenchymal stem cell culture method, but they were newly secreted or increased in secretion amount through the optimized culture method of the present invention (Table 3 and Table 4).

Through the above mass production method of the mesenchymal stem cell-derived proteins of the present invention, the proteins can be produced in larger quantities than through the conventional culture method.

Thus, by mass-producing proteins containing a variety of useful growth factors and cytokines, it can be very effective in producing and purifying desired target proteins. Besides, it can be used as a composition for skin regeneration and anti-wrinkle.

The total concentration of the secreted proteins obtained through the above production method is not limited thereto, but may be 30 μg/ml to 70 μg/ml by BCA assay.

According to another aspect of the present invention, it provides a mesenchymal stem cell conditioned medium containing proteins produced by the mass production method of the mesenchymal stem cell-derived protein.

Methods for mass production of mesenchymal stem cell-derived proteins and mesenchymal stem cell conditioned medium prepared therefrom are as described above.

The above stem cell conditioned medium may contain collagen in an amount of 5 to 20% by weight, preferably 10 to 15% by weight of the total conditioned medium, but is not limited thereto.

In addition, the stem cell conditioned medium may promote collagen production of fibroblasts.

In one specific example of the present invention, the amount of collagen contained in the stem cell conditioned medium of the present invention by absolute quantification method is 12.4% by weight of the total detected protein, and it is confirmed that this collagen content is more than double than that of the conventional method (Table 6).

Figure 7:
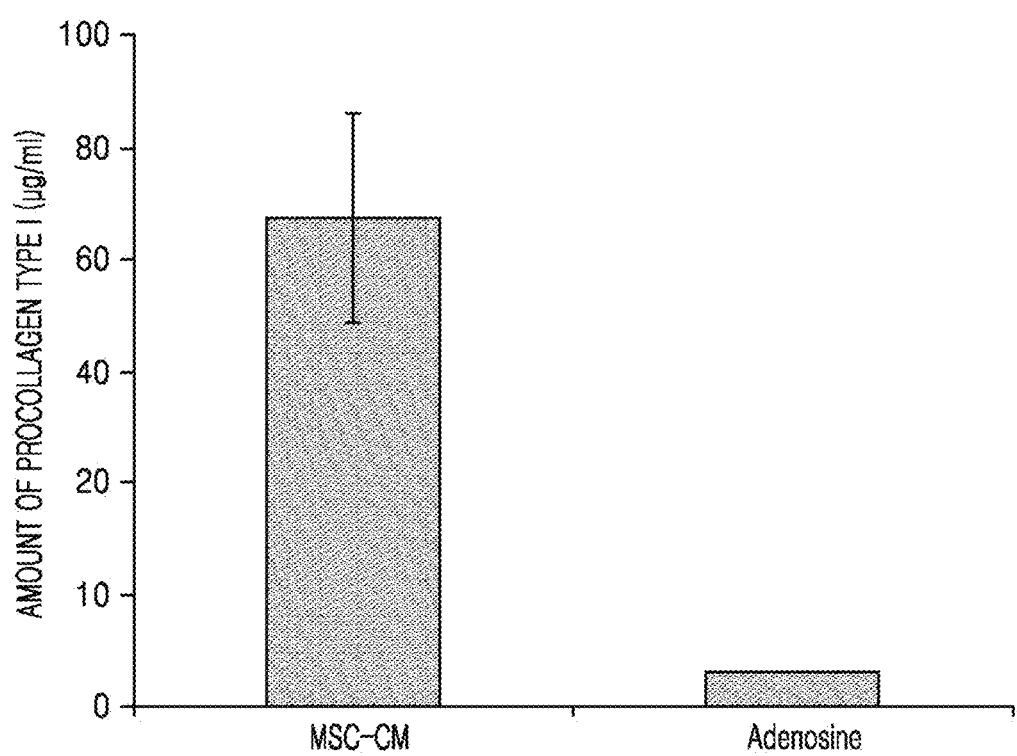
FIG. 7 shows the collagen synthesis effect of the stem cell conditioned medium under both optimal serum-free culture and cryopreservation conditions.

In another specific example of the present invention, the human fibroblast was treated with stem cell conditioned medium of the present invention, and it was confirmed that the collagen synthesis ability of the fibroblasts was improved more than 13 times than adenosine, which is a notification ingredient for functional cosmetic (FIG. 7).

According to another aspect of the present invention, it provides a cosmetic composition for skin regeneration or anti-wrinkle comprising the mesenchymal stem cell conditioned medium.

The above mesenchymal stem cell conditioned medium has been described above.

In the present invention, the term "skin regeneration" refers to the recovery process of skin tissue against damage caused by external and internal causes of the skin. The damage caused by the above external causes may include ultraviolet rays, external contaminants, wound and so on, and the damage caused by the above internal causes may be stress and so on.

In the present invention, the term "anti-wrinkle" means to maintain or improve the wrinkles and elasticity of the skin.

Figure 8:
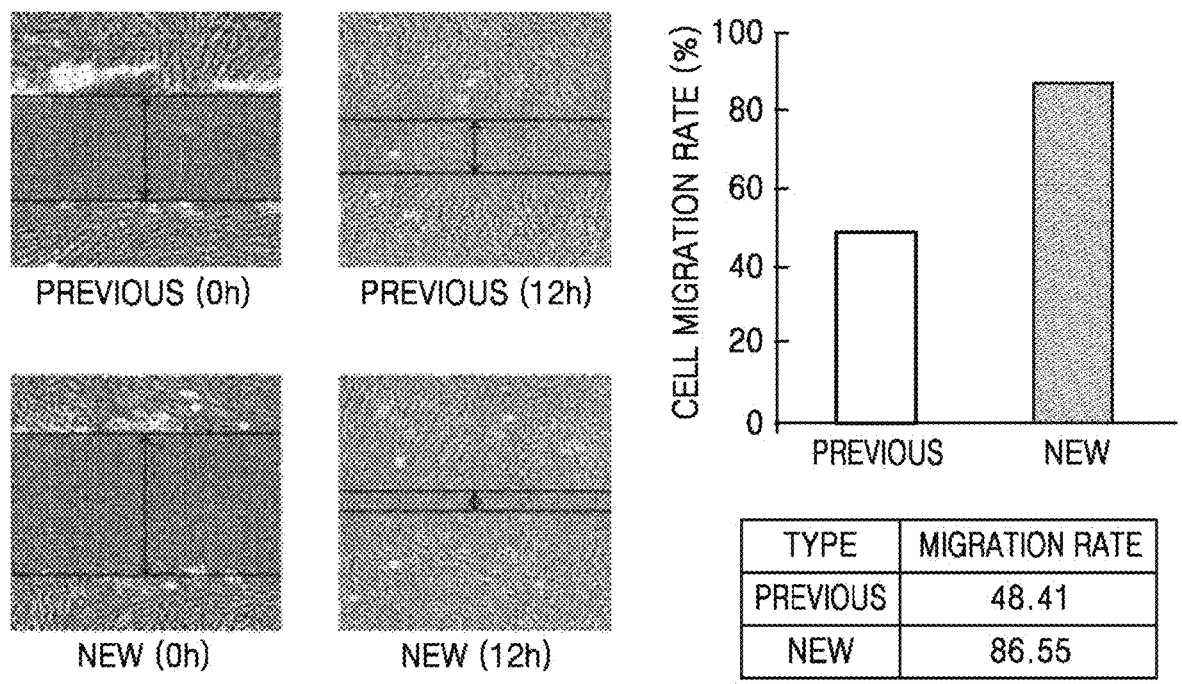
FIG. 8 shows the comparison of the wound healing efficacy of the stem cell conditioned medium under optimal serum-free culture conditions and cryopreservation conditions.
Figure 9:
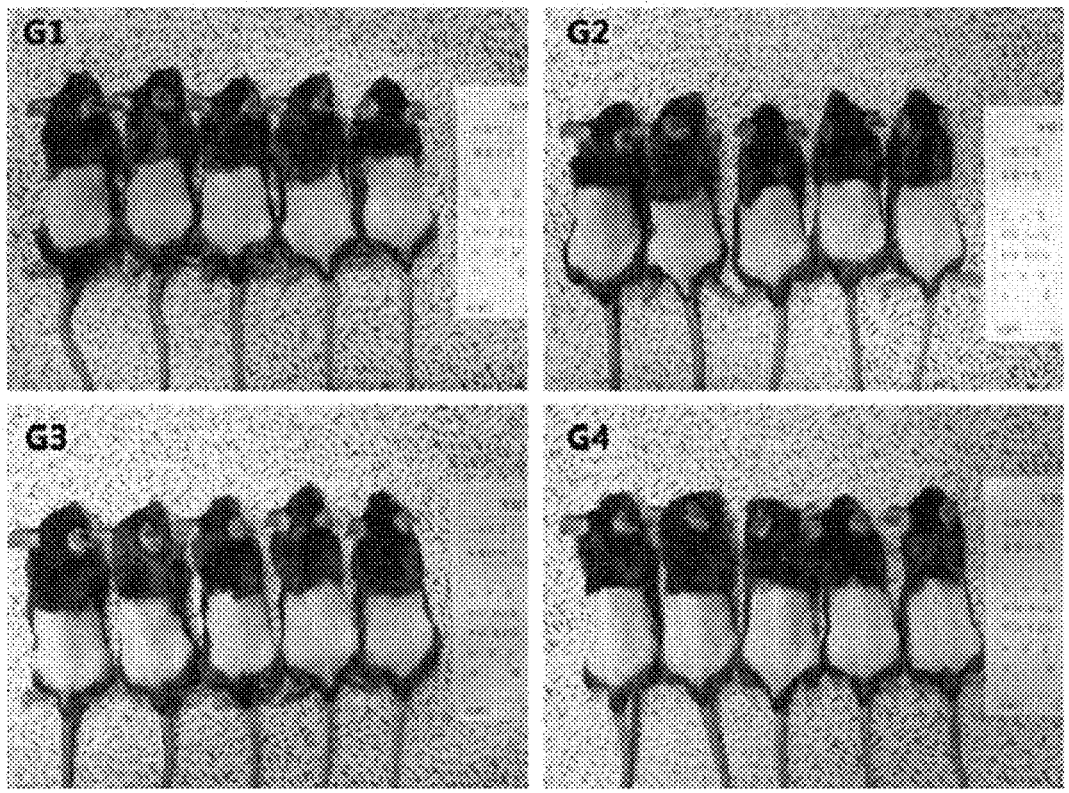
FIG. 9 shows the hair growth promoting effect of the mesenchymal stem cell conditioned medium in the hair growth inhibition model, showing the hair follicle condition on the 0th day of the test. G1 treated with distilled water, G2 treated with placebo, G3 treated with test substance and G4 treated with a positive control (5% Minoxidil).
Figure 10:
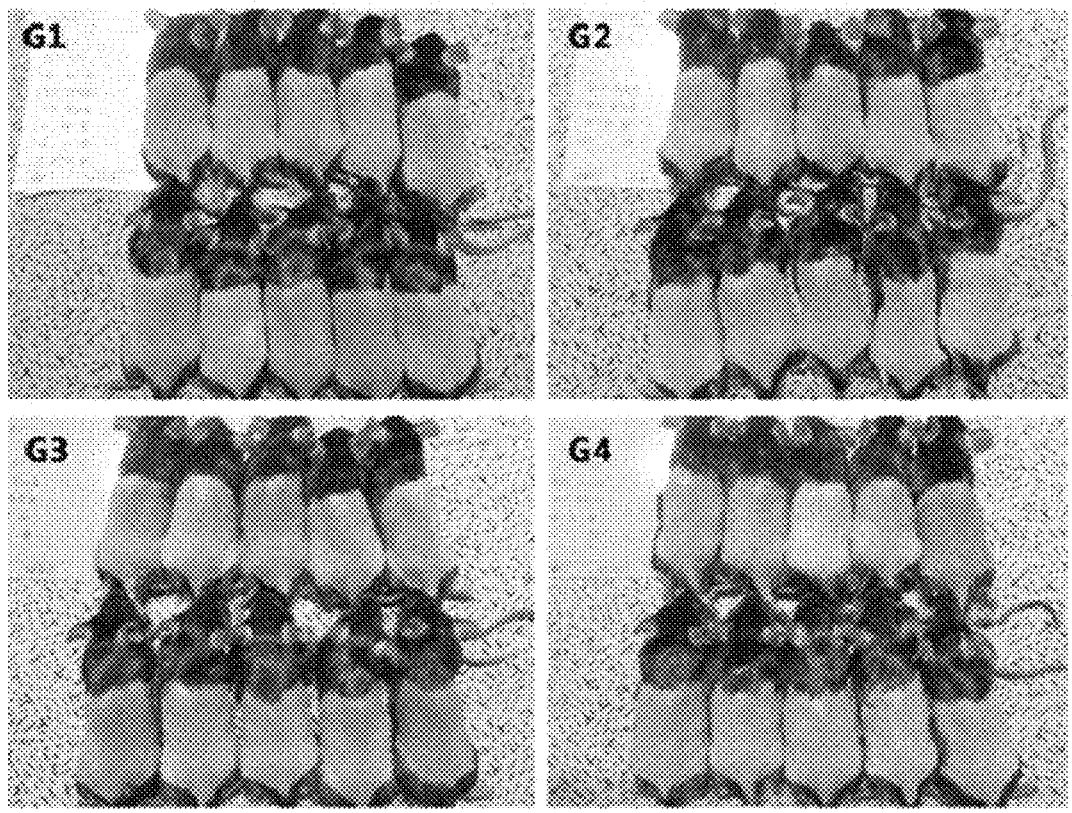
FIG. 10 shows the hair growth promoting effect of the mesenchymal stem cell conditioned medium in the hair growth inhibition model, showing the hair follicle condition on the 4th day of the test. G1 treated with distilled water, G2 treated with placebo, G3 treated with test substance and G4 treated with a positive control (5% Minoxidil).
Figure 11:
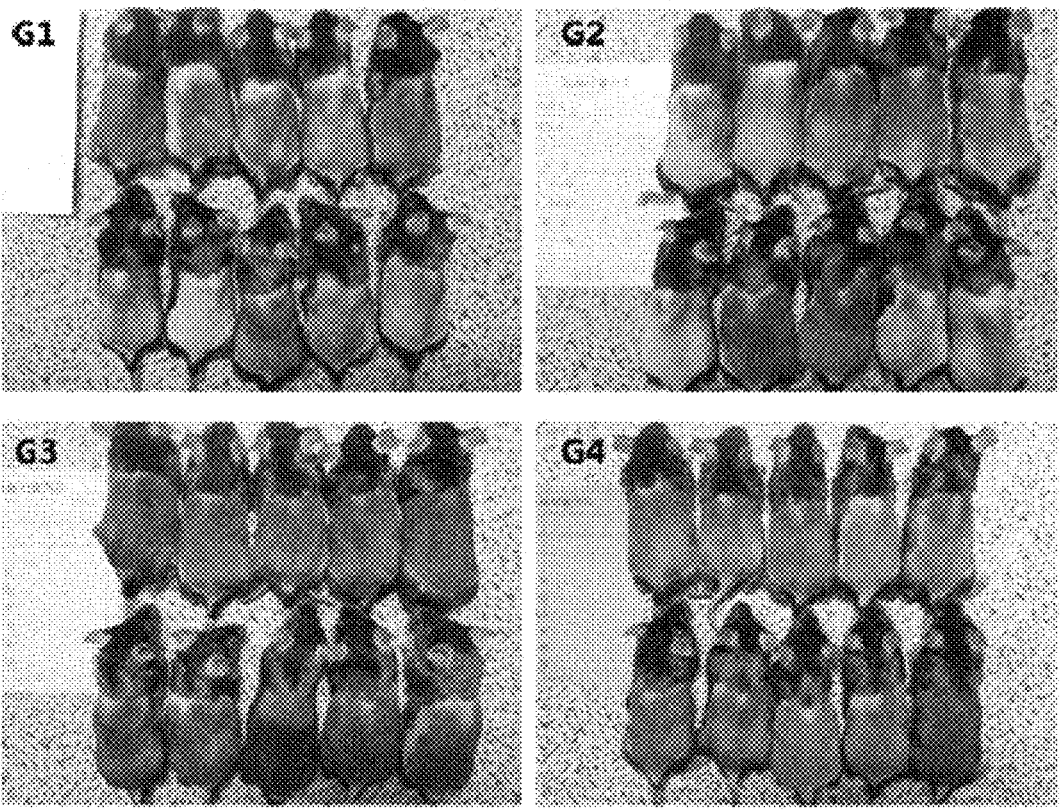
FIG. 11 shows the hair growth promoting effect of the mesenchymal stem cell conditioned medium in the hair growth inhibition model, showing the hair follicle condition on the 8th day of the test. G1 treated with distilled water, G2 treated with placebo, G3 treated with test substance and G4 treated with a positive control (5% Minoxidil).
Figure 12:
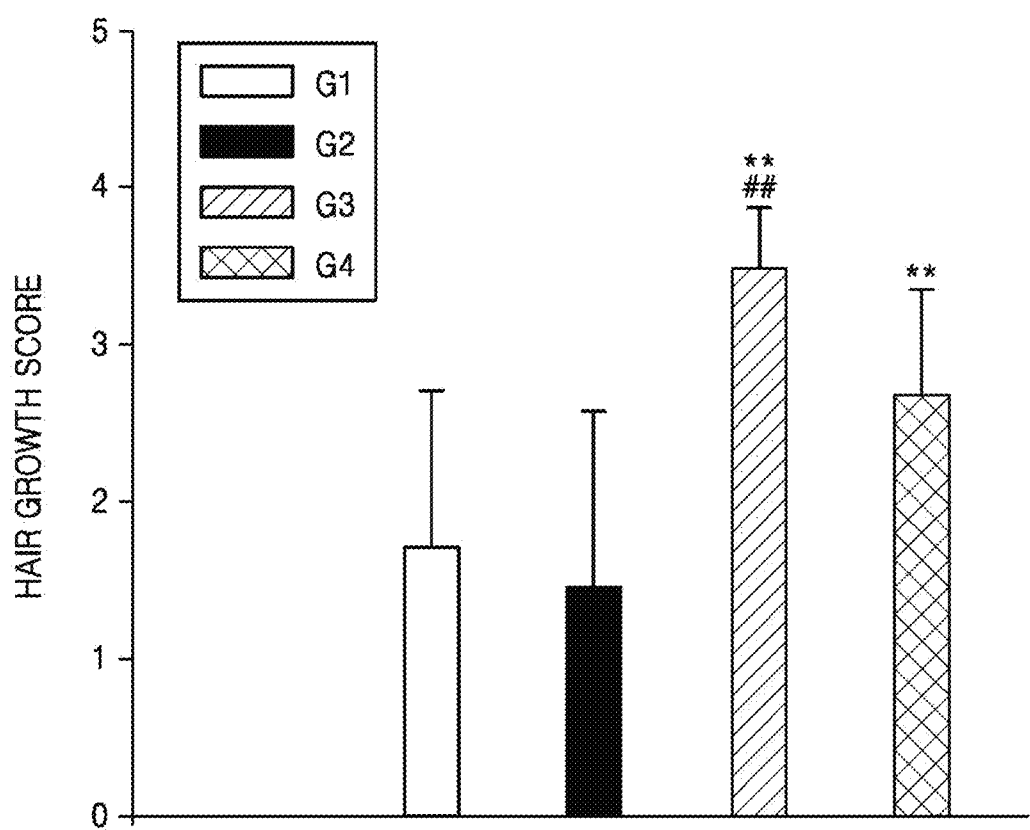
FIG. 12 shows the graph showing the hair growth score of the mesenchymal stem cell conditioned medium in the hair growth inhibition model. G1 treated with distilled water, G2 treated with placebo, G3 treated with test substance and G4 treated with a positive control (5% Minoxidil).
Figure 13:
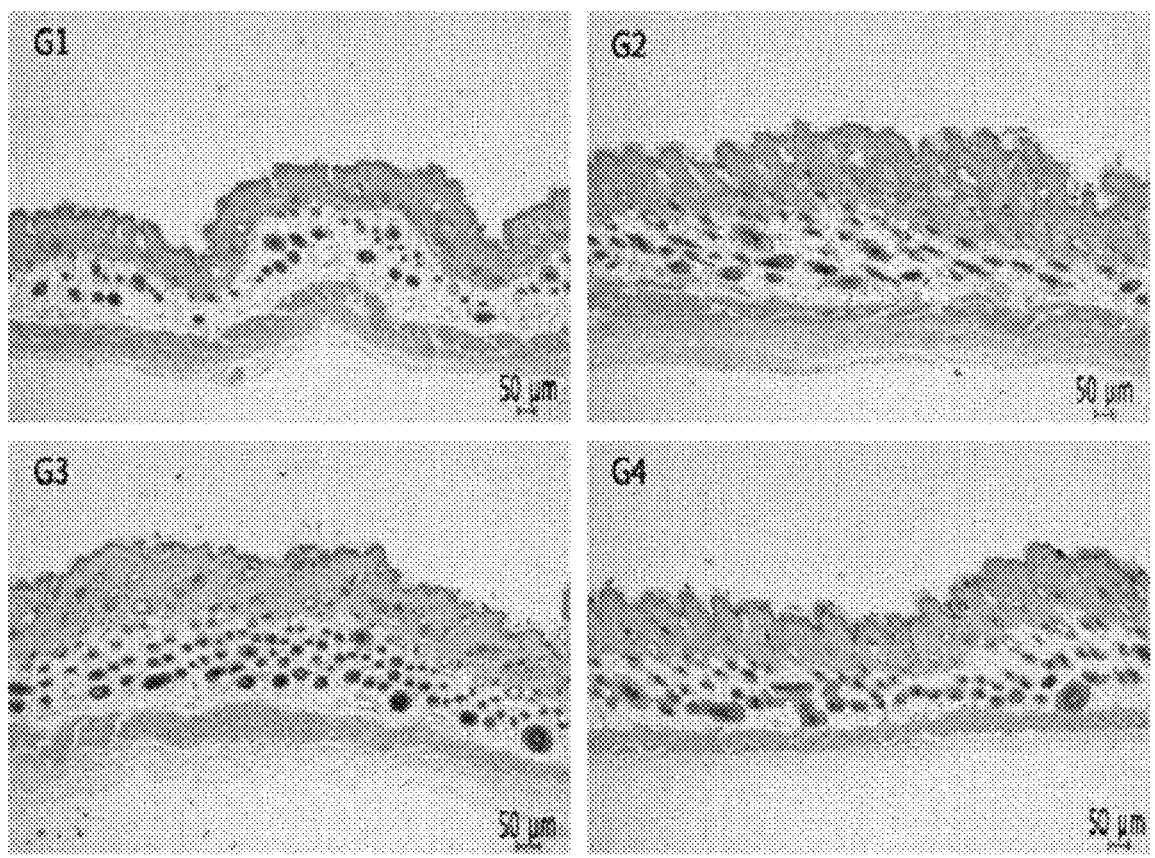
FIG. 13 is the histopathological follicle comparative photograph of a mouse treated with a mesenchymal stem cell conditioned medium in a hair growth inhibition model. G1 treated with distilled water, G2 treated with placebo, G3 treated with test substance and G4 treated with a positive control (5% Minoxidil).
Figure 14:
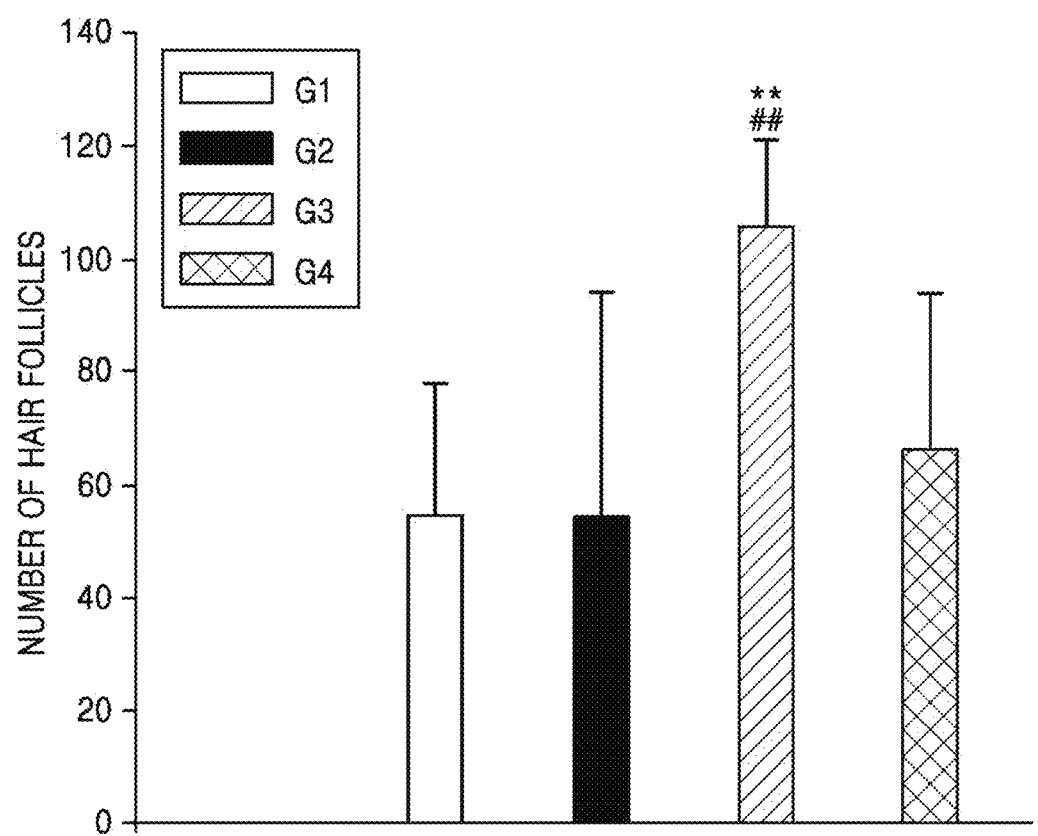
FIG. 14 is the graph comparing the number of hair follicles of a mouse treated with a mesenchymal stem cell conditioned medium in a hair growth inhibition model. G1 treated with distilled water, G2 treated with placebo, G3 treated with test substance and G4 treated with a positive control (5% Minoxidil).
Figure 15:
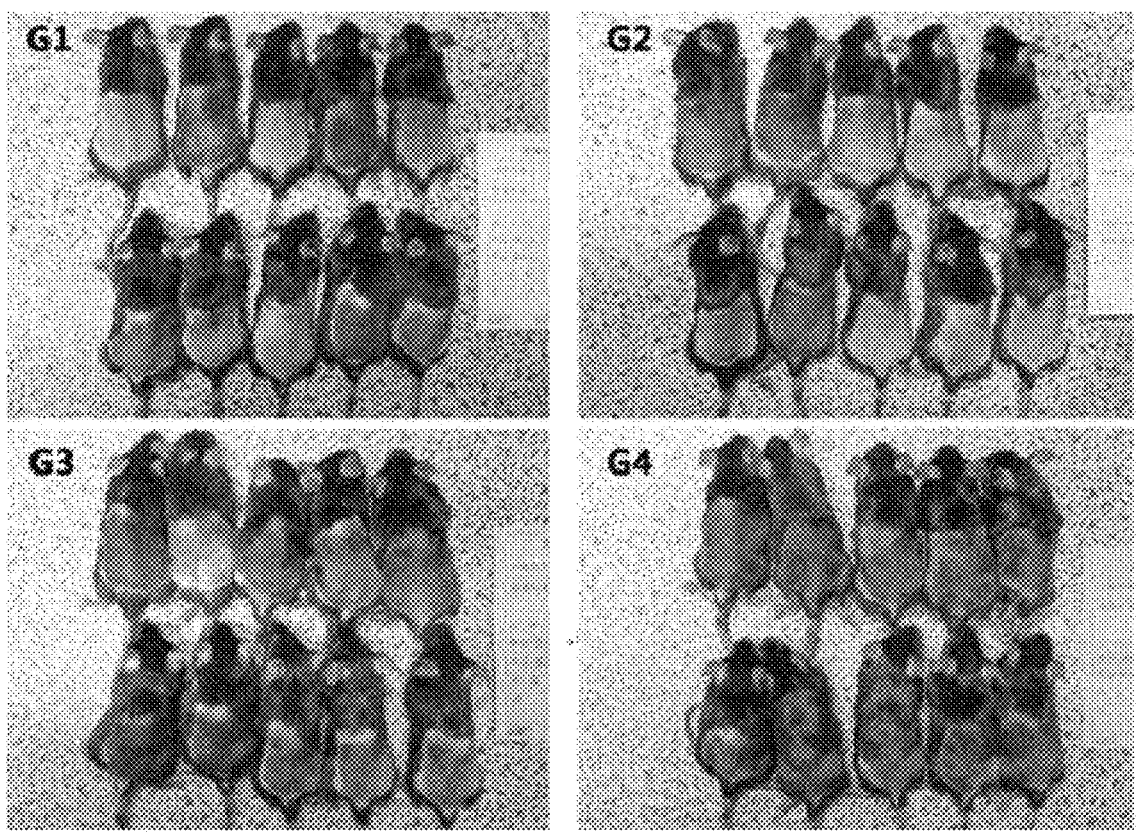
FIG. 15 shows the hair growth promoting effect of the mesenchymal stem cell conditioned medium in the anagen hair model, showing the hair follicle condition on the 13th day of the test. G1 treated with distilled water, G2 treated with placebo, G3 treated with test substance and G4 treated with a positive control (5% Minoxidil).
Figure 16:
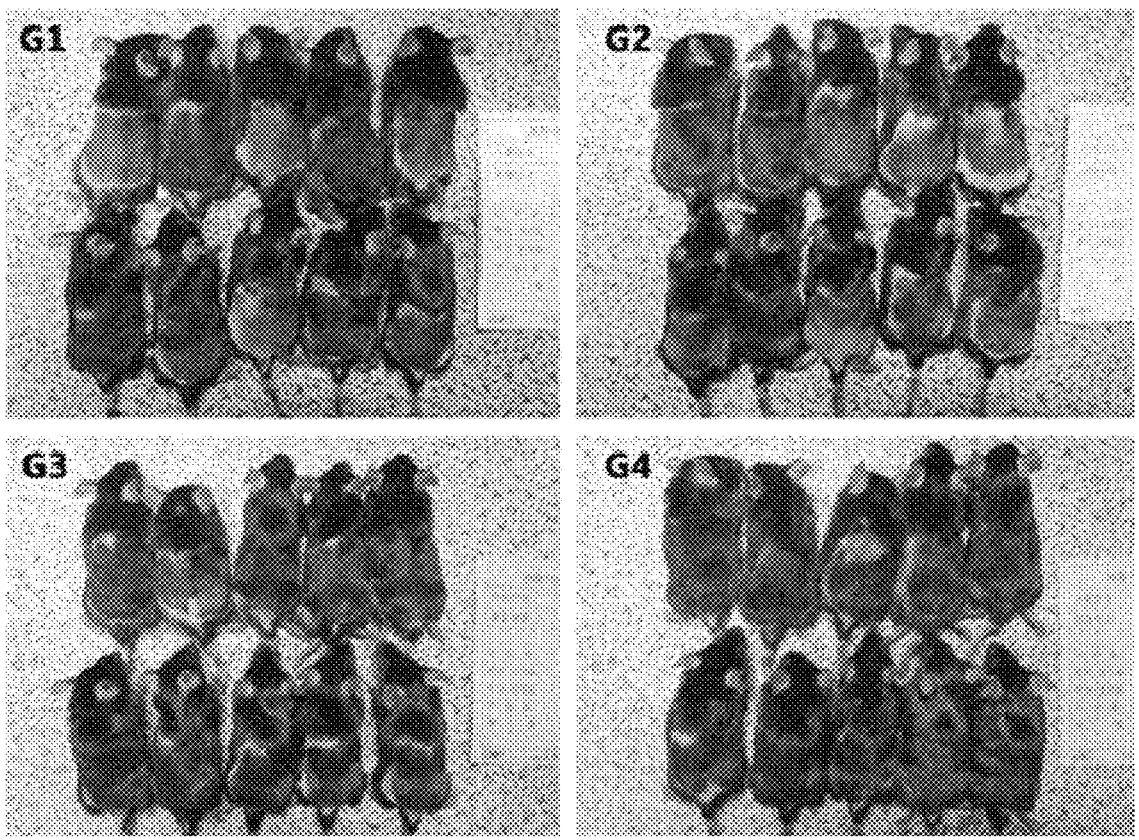
FIG. 16 shows the hair growth promoting effect of the mesenchymal stem cell conditioned medium in the anagen hair model, showing the hair follicle condition on the 15th day of the test. G1 treated with distilled water, G2 treated with placebo, G3 treated with test substance and G4 treated with a positive control (5% Minoxidil).
Figure 17:
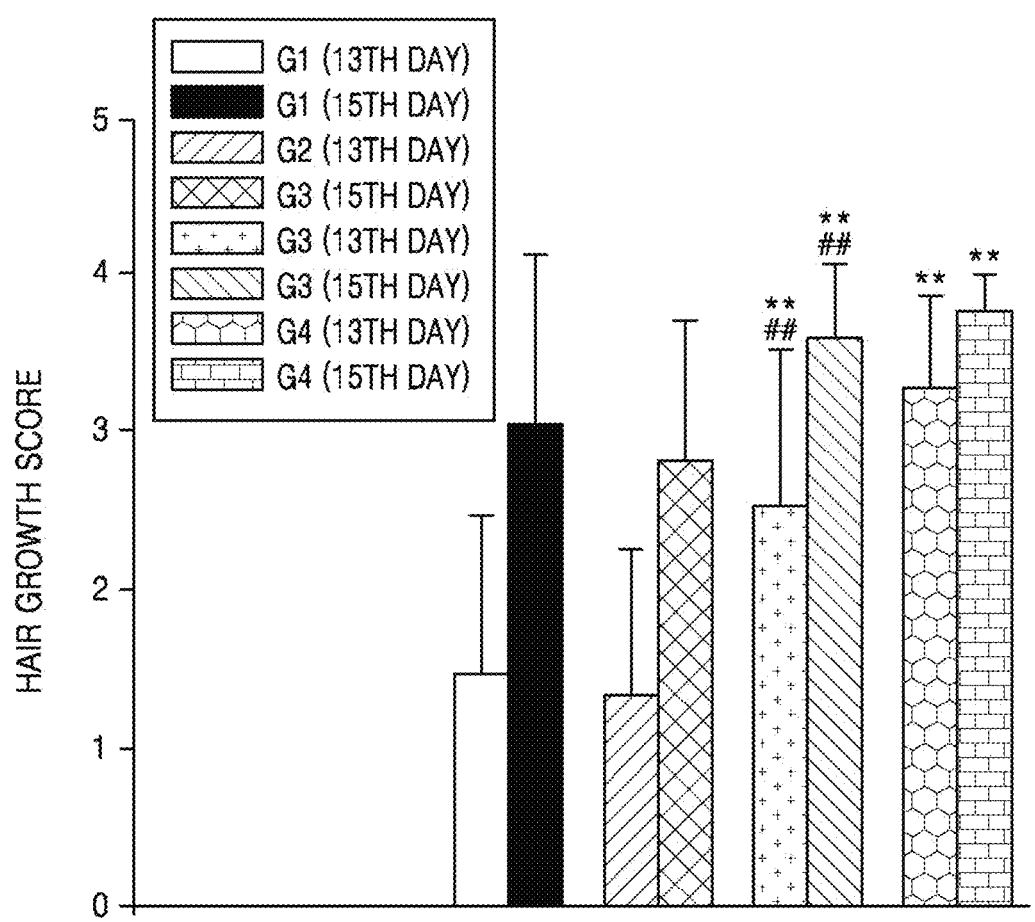
FIG. 17 is the graph showing the hair growth score of the mesenchymal stem cell conditioned medium in the anagen hair model. G1 treated with distilled water, G2 treated with placebo, G3 treated with test substance and G4 treated with a positive control (5% Minoxidil).
Figure 18:
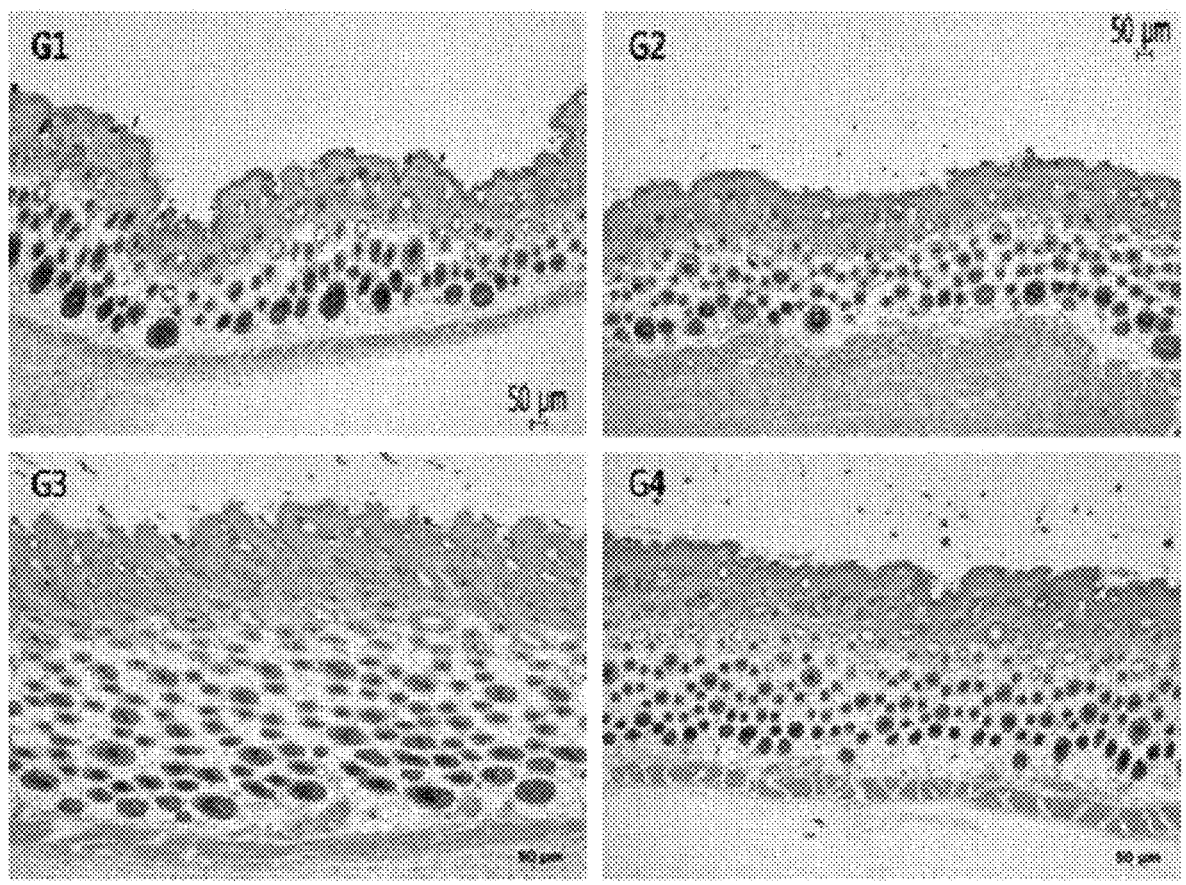
FIG. 18 is the histopathological follicle comparative photograph of a mouse treated with a mesenchymal stem cell conditioned medium in the anagen hair model. G1 treated with distilled water, G2 treated with placebo, G3 treated with test substance and G4 treated with a positive control (5% Minoxidil).
Figure 19:
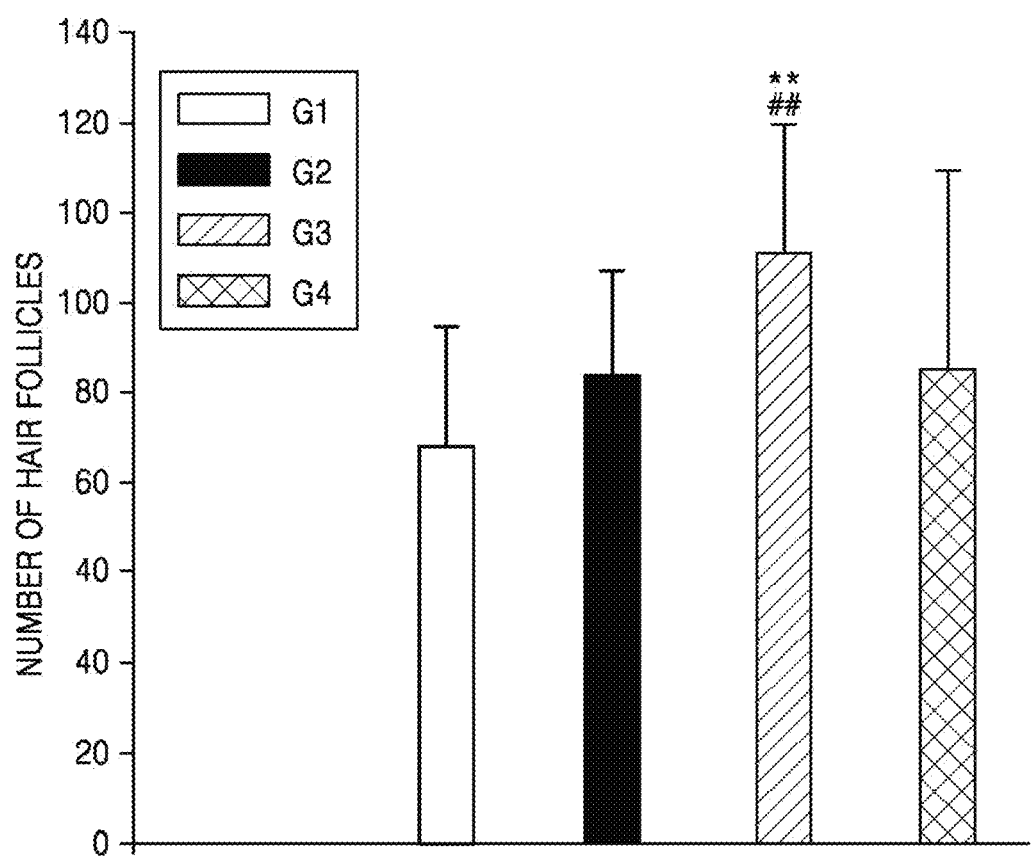
FIG. 19 is the graph comparing the number of hair follicles of a mouse treated with a mesenchymal stem cell conditioned medium in the anagen hair model. G1 treated with distilled water, G2 treated with placebo, G3 treated with test substance and G4 treated with a positive control (5% Minoxidil).

In a specific example of the present invention, through a wound healing assay capable of evaluating skin regeneration and wrinkle-improving efficacy, the above mesenchymal stem cell conditioned medium was compared with the mesenchymal stem cell conditioned medium from conventional method. As a result, it was confirmed that the wound healing was significantly increased in the above culture method (FIG. 8). As described above, since the mesenchymal stem cell conditioned medium of the present invention contains a large amount of proteins effective for wound healing, the composition containing the mesenchymal stem cell conditioned medium of the present invention can be used for skin regeneration and anti-wrinkle.

In the present invention, the mesenchymal stem cell conditioned medium described above may be contained in an appropriate amount to exhibit the above-described effects.

In addition to the above-mentioned mesenchymal stem cell conditioned medium, the cosmetic composition according to the present invention may contain various components commonly used in external preparations for skin, if necessary, within the range not deteriorating the effect of the present invention. For example, water-soluble components, powder components, surfactant, moisturizing agent, viscosity controlling agent, antiseptic, antioxidant, fragrance, pigment, and so on may be mixed.

Formulations of the cosmetic composition according to the present invention may be optionally selected and may be prepared by mixing the mesenchymal stem cell conditioned medium as an active ingredient with conventionally known excipients for cosmetics such as water, physiological saline, glycerol, oil, Surfactants, Sensitizing agents, Chelating agents, Dyes, Preservatives, Fragrances, and so on. And then a cosmetic composition in the form of Lotions, liquids, emulsions, suspensions, tablets and capsules is formed.

By using the cosmetic composition described above, it is possible to produce basic cosmetics such as Flexible lotion, Milk lotion, Nourishing cream, Massage cream, Essence, Cleansing foam, Cleansing water, Pack or body oil, etc., and color cosmetics such as Foundation, lipstick, mascara or make-up base, etc., and also to produce a cleanser and a bath agent.

In order to promote the absorption and fixation of the mesenchymal stem cell conditioned medium of the cosmetic composition into the skin, 1 to 7% by weight of glycerin may be contained in the excipient for cosmetic composition to constitute the cosmetic composition containing the mesenchymal stem cell conditioned medium but not limited thereto.

In addition, sunflower oil may be included in cosmetic excipients to provide an antioxidant function to the cosmetic composition, but is not limited thereto.

According to another aspect of the present invention, it provides a pharmaceutical composition for skin regeneration comprising the mesenchymal stem cell conditioned medium.

The above mesenchymal stem cell conditioned medium has been described above.

The composition of the present invention has confirmed from wound healing efficacy superior to that of the mesenchymal stem cell conditioned medium cultured by the conventional method through a wound healing assay (FIG. 8), and thus can be used as a pharmaceutical composition for skin regeneration.

The throughput of the pharmaceutical composition for skin regeneration used in the present invention should be a pharmacologically effective amount. In the present invention, the term "pharmaceutically effective amount" means an amount sufficient to treat a disease at a reasonable benefit/risk ratio applicable to medical treatment. An effective dosage level will vary depending on the species and severity, such as the type of disease, activity of the drug, sensitivity to the drug, time of administration, route of administration, rate of release, duration of the treatment, factors including co-administered drugs, and other factors well known in the medical field. Effective amounts may vary depending on the route of administration, the use of excipients, and the likelihood of use with other agents, as will be appreciated by those skilled in the this technical field.

In the present invention, the pharmaceutical compositions for skin regeneration may be prepared into pharmaceutical formulations using methods well known in this field so as to provide rapid, sustained or delayed release of the active ingredient after administration to the mammal.

Accordingly, the pharmaceutical composition of the present invention may be formulated in the form of powder, granule, tablet, capsule, suspension, emulsion, syrup, aerosol or the like oral preparation, external preparation and patch according to a conventional method. In addition, it may further contain suitable carriers, excipients or diluents conventionally used in the preparation of the composition.

The above carrier may contain non-naturally occurring carrier.

For example, carriers, excipients and diluents that can be included in the pharmaceutical composition of the present invention include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methylhydroxybenzoate, propylhydroxybenzoate, talc, magnesium stearate and mineral oil. In the case of medicine manufacture, it is prepared using diluents or excipients such as commonly used fillers, weighting, binding agents, wetting agents, disintegration, surfactants, and so on.

According to another aspect of the present invention, a cosmetic composition for prevention of hair loss or promotion of hair growth comprising the above mesenchymal stem cell conditioned medium is provided.

According to another aspect of the present invention, a pharmaceutical composition for alopecia treatment or promotion of hair growth comprising the above mesenchymal stem cell conditioned medium is provided.

The above mesenchymal stem cell conditioned medium, cosmetic composition and pharmaceutical composition are as described above.

In the present invention, the term "prevention of hair loss" means preventing and suppressing hair loss phenomena, and "alopecia treatment" means improving or alleviating symptoms of hair loss.

In the present invention, the above hair loss means a phenomenon in which the hair falls off the scalp or a condition in which the hair is loose or thinned, and the direct or indirect cause of its occurrence is unclear and all symptoms classified as hair loss in this field used as meaning to be included.

For instance, the above hair loss may include both hair loss symptoms due to blood circulation failure, sebum hypersecretion by hormones, decreased scalp function due to peroxide or bacteria, aging, genetic factors, stress, complex effects of these and the like.

In the present invention, the term "hair growth" includes not only promotion of new hair production, but also including making existing hair grow healthy, another terms used in the industry are concepts of broad sense that contain meaning of promotion of hair growth.

Human and animal hair repeat the cycle of hair composed during the growth phase(anagen), the regression phase(catagen), and the resting phase(telogen). In a specific example of the present invention, through an animal test using a mouse, by confirming the effect of delaying the transition from the anagen of the hair to the catagen (catagen suppression or anagen extension effect) and the effect of promoting the transition from the telogen to the anagen (anagen induction effect), it was evaluated the effect of prevention of hair loss, alopecia treatment and promotion hair growth using the stem cell conditioned medium of the present invention.

Human hair has a different hair cycle of individual hair, but in the case of a mouse, all hair is in the same hair cycle at the beginning and it is also possible to match the hair cycle in the same way by an artificial method. It is useful in experiments to see changes in hair cycle.

In addition, in the C57BL/6 mouse used in the examples of the present invention, since the melanocytes that make the pigment are not present in the epidermis but exist only in the hair follicle, it has the property that skin color is determined by the amount of melanin pigment in hair follicle.

Since the synthesis of melanin pigment from hair follicle occurs only during the anagen, skin color becomes black in the anagen, and becomes pink in the catagen and the telogen when melanin pigment synthesis does not occur.

By utilizing such characteristics, there is an advantage that it is possible to confirm the cycle of hair using skin color without performing skin tissue examination. Also, when the B6 mouse reaches 4 to 7 weeks old at the age of birth, most of the hair is in the telogen and the color of the skin becomes pink. In addition, when the hair in the telogen is pulled at the same time and removed, it is possible to shift all the hair simultaneously to the anagen.

In a specific example of the present invention, in order to evaluate the regression effect of catagen, after inducing the anagen by removing the hair of the telogen C57BL/6 mouse and treating a catagen inducer such as dexamethasone while treating the test substance, the degree of suppression of catagen was evaluated by observing hair growth level and the number of hair follicle. As a result, as shown in FIG. 9 to FIG. 14, it was found that the mesenchymal stem cell conditioned medium treated group had prevention of hair loss and hair growth promotion effects.

In another specific example of the present invention, in order to evaluate the growth-inducing effect, after the hair on the back of the telogen C57BL/6 mouse is cut, while treating the test substance, the degree of induction in the anagen was evaluated by observing the hair growth level and the number of hair follicles. As a result, as can be seen from the comparison of the results of FIG. 15 to FIG. 19, it was found that the treatment group of mesenchymal stem cell conditioned medium showed a hair growth promoting effect.

As described above in the present invention, using an animal model, it has been found that the mesenchymal stem cell conditioned medium of the present invention can contribute to prevention of hair loss, alopecia treatment and promotion of hair growth.

MODE FOR INVENTION

The present invention will be explained in more detail through the following examples. These examples are merely for illustrating the present invention, and the scope of the present invention is not construed as being limited by these examples.

Example 1. Confirm Optimum Conditions by Cell Inoculation Density

In order to find optimal cell inoculation density conditions, the total protein contents present in the stem cell conditioned medium obtained at various cell inoculation densities were investigated by BCA measurement method. About the stem cell culture liquid obtained by inoculating Human Amniotic Fluid-Derived mesenchymal stem cells at a density of 5,000, 10,000, 15,000, 20,000 and 25,000 cells/cm$^2$ into culture vessels, respectively, and then serum-free culturing for 120 hours, total Protein content was measured. The specific culture conditions and culture process are as follows.

First, $1\times10^6$ frozen mesenchymal stem cells were thawed and inoculated into a T75 flask. The medium used was DMEM (Low Glucose, Welgene) containing 10% FBS (Fetal Bovine Serum, Gibco, Austria origin) and 100 μg/ml penicillin and streptomycin (Gibco).

Next, when about 70 to 90% of the cells proliferate in the flask at 37° C. in a 5% $CO_2$ incubator for 3 days, subculture was carried out 2 to 3 times at a ratio of 1:3, and sufficient cells secured. Each subculture did not exceed 70% in the flask and subculture period took 3-5 days. After the above subculture, all media except the cells attached to the surface of the culture vessel were removed and washed 2 to 3 times with D-PBS. 2 ml Trypsin-EDTA was added to remove the cells from the surface of the culture vessel, and the cells were transferred to a 15 me tube, centrifuged at 1000 rpm for 5 minutes, and then all medium components were removed. DMEM/F12, a serum-free medium, was added to the new flask, inoculated at a cell density of 10,000 to 25,000 cells/cm², and then cultured at 37° C. in a 5% $CO_2$ incubator. After 120 hours, the conditioned medium was collected.

The concentration of protein was quantified using the BCA assay method for the conditioned medium collected in the above process. The specific experimental procedure is as follows.

First, proteins were extracted from 7 ml of conditioned medium. After filling the 1×PBS (GIBCO, NY, USA) to 20 ml, the sample was concentrated by centrifugation four times at 4000 rpm at 4° C. for 30 minutes using a 20 ml Vivaspin 3K filter (GE Healthcare, Chalfont St. Giles, UK). Concentration process was carried out while continuing to fill the 1×PBS. When it was concentrated to about 1 ml, it was centrifuged 4 times at 4° C. at 14,000 rpm for 30 minutes using a 500 μl Vivaspin 3K filter (GE Healthcare, Chalfont St. Giles, UK), and concentrated to 300 μl.

Next, protein quantitation was performed using a BCA quantitative kit (Thermo Fisher Scientific Inc, Rockford, Ill. USA). First, 2 mg/ml of BSA (Bovine serum albumin) ampoule was diluted to prepare the standard sample of Table 1 below.

TABLE 1

| Vial | Volume of Diluent (μl) | Volume and Source of BSA (μl) | Final BSA Concentration (μg/ml) |
|---|---|---|---|
| A | 0 | 300 of Stock | 2000 |
| B | 125 | 375 of Stock | 1500 |
| C | 325 | 325 of Stock | 1000 |
| D | 175 | 175 of vial B dilution | 750 |
| E | 325 | 325 of vial B dilution | 500 |
| F | 325 | 325 of vial B dilution | 250 |
| G | 325 | 325 of vial B dilution | 125 |
| H | 400 | 100 of vial B dilution | 25 |
| I | 400 | 0 | 0 = Blank |

Next, an operating reagent was prepared. BCA reagents A and B were mixed at a room temperature of 50:1. Then, loading 25 μl each of the standard sample and the above obtained stem cell conditioned medium concentrate to a 96-well plate, and then 200 μl of working reagents were loading. The above process was repeated three times. The sample-loaded 96-well plate was placed in Multiskan FC (Thermo Fisher Scientific Inc, Rockford, Ill. USA) and incubated at 37° C. for 30 minutes. After 30 minutes, after cooling at room temperature, the absorbance was measured at 562 nm.

As a result, according to the cell inoculation density, protein concentrations were confirmed as of 22.774 μg/ml, 31.831 μg/ml, 41.327 μg/ml, 51.933 μg/ml, and 49.711 μg/ml respectively. The protein concentration was found to be maximized at the cell inoculation density of 20,000 cells/cm², confirming the result that the total protein content decreased at 25,000 cells/cm² inoculation density rather than at 20,000 cells/cm² inoculation density. As a result, it was confirmed that the optimal stem cell inoculation density for high-level production of the protein secreted from the stem cells in the serum-free culture stage was 20,000 cells/cm² (FIG. 1).

Example 2. Comparison of Protein Production by Culture Time

After inoculation of human amniotic fluid stem cells into a culture vessel, total protein content present in the conditioned medium of stem cells by serum-free culture time until culture was collected was examined by BCA assay. Cells were inoculated in a culture vessel at a density of 20,000 cells and serum-free cultured, then protein concentrations were measured for stem cell conditioned medium obtained at intervals of 12 hours from 72 hours to 144 hours. The cell type, culture method, and protein concentration measurement method were carried out in the same manner as in Example 1, and the serum-free culture time was different.

As a result, the total protein contents present in the stem cell conditioned medium obtained when the serum-free culture time was from 72 hours to 84 hours, 96 hours, 108 hours, and 120 hours was increased to 26.934 μg/ml, 28.647 μg/ml, 37.674 μg/ml, 38.400 μg/ml, or 44.520 μg/ml. However, the total protein contents present in the stem cell conditioned medium obtained when the serum-free culture time exceeds 120 hours and is 132 hours and 144 hours was 41.166 μg/ml and 39.610 μg/ml, respectively, which were lower than the stem cell conditioned medium obtained in 120 hours (FIG. 2).

In view of the above results, it was confirmed that when the serum-free culture time is about 120 hours, the total protein content secreted from the stem cells was maximized.

Example 3. Comparison of Cell Viability According to Cryopreservation Conditions of Mesenchymal Stem Cells Cryopreservation conditions for mesenchymal stem cells, specifically, the survival rates of stem cells according to the type of freezing solution were compared, and optimal cryopreservation conditions were established. Generally, in order to cryopreserve mesenchymal stem cells, 1 ml of cell banking media mixed with 10% DMSO, 20% FBS and 70% cDMEM medium is placed in a cryopreservation vial with $1\times10^6$ stem cell and stored in a −196° C. liquid nitrogen tank. So, cryopreservation and cell viability of mesenchymal stem cells with various freezing solutions in which the cryopreserved stem cells can be thawed and then may further improve the productivity of the secreted protein of stem cells obtained through serum-free culture were compared with the conventional cryopreservation method together. Human amniotic fluid derived mesenchymal stem cells $1\times10^6$ of the same passage with 1 ml of various freezing solutions together in each cryopreservation vials were stored in a deep freezer at −80° C. for 2 weeks, after that, the cells were thawed and cell viabilities were measured and compared. The four cryopreservation solutions CRYO-GOLD (Revive Organtech, Cat. #10003), CRYO-ROS (Revive Organtech, Cat. #10002), STEM-CELL BANKER (Zenoaq, Cat. #BLC-3) and CellFreezer (Genenmed, Cat. #GEN-1000-050) were used. The specific experimental method are as follows.

First, the cell tube of the cryopreservation was taken out, placed in a constant temperature water bath at 37° C., and melted while shaking for about 2 minutes continuously. When frozen cells were dissolved by about 90%, they were transferred to a 15 ml tube containing 10 ml growth medium. Then, after centrifugation at 1000 rpm for 5 minutes, the supernatant media was removed, and 10 ml growth medium was added to the cell pellet. Next, 20 µl of the cell solution was placed in the 96-well plate, and 20 µl of 0.4% trypan blue was added, then pipetting and mixed well. The hemocytometer was covered with a cover glass, and 10 µl of the mixed solution was placed in both gaps. And then, the cell number was measured by adjusting the magnification of the microscope to 40-fold. At this time, dead cells stained blue were counted first, and live cells which were not stained were counted. We counted the four areas of the grid and averaged the number of live cells per one grid. The number of total live cells was calculated according to the following formula below.

live cells=live cells per one grid×2×$10^4$×Cell solution volume

Then, cell viability was calculated according to the following formula below.

cell viability=the number of live cells/(the number of live cells+the number of dead cells)×100

Consequently, it was confirmed that the mesenchymal stem cells thawed after cryopreservation for 2 weeks in a liquid nitrogen tank by a previously known cryopreservation method (control group; 10% DMSO+20% FBS+70% cDMEM) show average cell viability of 84.41%. Then, it was confirmed that the mesenchymal stem cells thawed after cryopreservation with the cell freezing solutions CRYO-GOLD, CRYO-ROS, STEM-CELL BANKER and CellFreezer for 2 weeks in −80° C. show average cell viability of 92.25%, 89.15%, 91.92% and 86.55%, respectively. As a result, the remaining three cell freezing solution except for CellFreezer showed superior cell viability as compared with the conventionally known cryopreservation method (FIG. 3).

Example 4. Comparison of Secretory Protein Contents of Mesenchymal Stem Cells According to Cell Freezing Solution The human amniotic fluid-derived mesenchymal stem cells, which were cryopreserved with the various cell freezing solutions used in above Example 3, were subjected to serum-free culture conditions established through Example 1 and Example 2 above, that is, the cells were inoculated in a culture vessel at a density of 20,000 cells/cm$^2$, and after serum-free culture, the total protein contents present in the stem cell conditioned medium collected at 120 hours were examined by BCA array and compared.

The stem cells cryopreserved in a liquid nitrogen tank for 2 weeks by a previously known cryopreservation method (control group; 10% DMSO+20% FBS+70% cDMEM) were inoculated at a density of 20,000 cells/cm$^2$, and after 120 hours of serum-free culture, the total protein content present in the collected stem cell conditioned medium was 37.754 µg/ml, and the stem cells thawed after cryopreservation in −80° C. for 2 weeks with the cell freezing solutions CRYO-GOLD, CRYO-ROS, STEM-CELL BANKER and CellFreezer were inoculated at a density of 20,000 cells/cm$^2$, after 120 hours of serum-free culture, the total protein contents present in the collected stem cell conditioned medium were 51.030 µg/ml, 46.229 µg/ml, 33.803 µg/ml and 20.477 µg/ml, respectively, and then it was confirmed that the largest amount of proteins were secreted in stem cells stored in CRYO-GOLD solution (FIG. 4).

In view of the above results, the cell viability and the protein production of stem cells cryopreserved with various CRYO-GOLD solutions was the most excellent compared with the mesenchymal stem cells stored in the previously liquid nitrogen tank. Then, it was confirmed that the method of cryopreserving stem cells at −80° C. using CYRO-GOLD was an optimal cryopreservation method that can maximize the content of stem cell-secreted proteins.

Example 5. Comparison of Acquisition Frequency of Stem Cell Conditioned Medium Obtained from Optimal Culture Conditions Next, the total protein contents in the stem cell conditioned medium obtained by a previously known serum-free culture conditions and cryopreservation conditions, and in the stem cell conditioned medium obtained through the present invention serum-free culture conditions and cryopreservation conditions was investigated and compared by BCA array method. The above conditioned medium was obtained three times at intervals of 120 hours.

The existing conditioned medium means the mixed conditioned medium cultured in serum-free medium and collected at 72 hours, 144 hours, and 216 hours, respectively, after inoculating mesenchymal stem cells cryopreserved together with 10% DMSO+20% FBS+70% cDMEM mixed medium in −196° C. liquid nitrogen tank, at a density of 10,000 cells/cm$^2$ in a culture vessel, and the new conditioned medium means the mixed conditioned medium cultured in serum-free medium and collected at 120 hours, 240 hours, and 360 hours, respectively, after inoculating mesenchymal stem cells cryopreserved together with CRYO-GOLD solution in −80° C. deep freezer, at a density of 20,000 cells/cm$^2$ in a culture vessel.

As a result, the total protein contents in the stem cell culture obtained at 72, 144, and 216 hours in the serum-free culture conditions inoculated with the mesenchymal stem cells stored in the previously cryopreservation method (−196° C., 10% DMSO+20% FBS+70% cDMEM) at a density of 10,000 cells/cm$^2$ in the culture vessel was 4.187 µg/ml, 4.52 µg/ml and 2.686 µg/ml, respectively. The total protein content produced over 3 times was measured with an average level of 3.6 µg/ml.

On the other hand, the total protein content present in the stem cell conditioned medium obtained at 120 hours, 240 hours, and 360 hours in the serum-free culture conditions inoculated with the mesenchymal stem cells cryopreserved in newly established cryopreservation method (−80° C., CRYO-GOLD) at a density of 20,000 cells/cm$^2$ in the same culture vessel was 44.52 µg/ml, 35.69 µg/ml and 28.74 µg/ml, with an average of 36.3 µg/ml, and it could be confirmed that the content of protein was greatly increased (FIG. 5).

In view of the above results, it was confirmed that the content of human amniotic fluid derived mesenchymal stem cell secretion protein obtained through the optimal cell cryopreservation and serum-free culture conditions established by the present invention was improved 10-fold or more.

Example 6. Quantitative Comparison Using Antibody Arrays of Growth Factors Contained in Stem Cell Cultures Obtained Under Optimum Culture and Storage Conditions The types of proteins produced under the culture and storage conditions of mesenchymal stem cells established through above Examples 1 to 5 were analyzed qualitatively.

A qualitative analysis was performed by repeating a total of 1357 proteins twice with Signaling Explorer Antibody Array (Cat. No. SET100) from Fullmoon BioSystems Inc. The specific experimental procedure is as follows.

First, 50 μg of the protein sample was adjusted to 75 μl using a labeling buffer, followed by biotin labeling with Biotin/DMF (N, N-dimethylformamide) solution. The above labeled protein binds to the antibody attached to the slide as a probe.

Next, Blocking was carried out to prevent binding of the slide to the protein, coupling mixture was prepared in the milk powder to prevent binding with the coupling reagent, and then coupled with the antibody microarray slide which had undergone the blocking process. The labeled protein binds to the antibody of the probe through the above process.

Then, the protein that has undergone the binding process was detected using fluorescence, and the extent of fluorescence by reading it with a scanner was quantified. Scanned protein array data was quantified by degree of expression of each protein through the data analysis process.

Scanning was through GenePix 400B (Agilent) scanner and GenePix Pro 6.0 (Agilent) Image Analysis, and standardization about whole spots was performed through Genowiz 4.0 (Ocimum Biosolutions, India) software.

Figure 6:
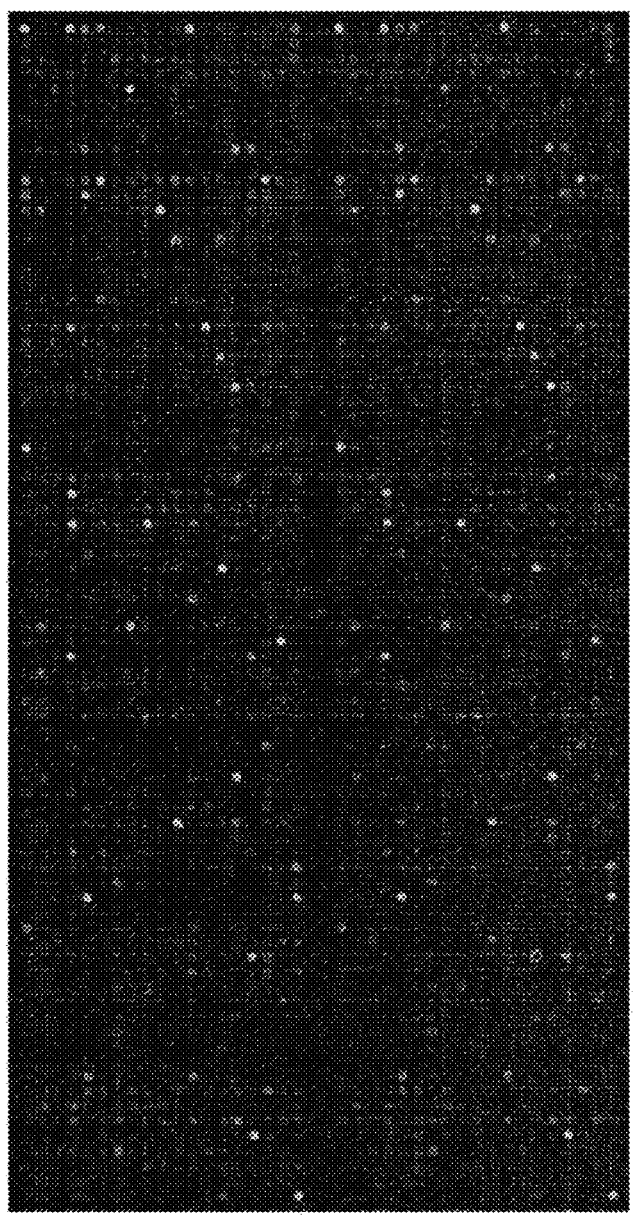
FIG. 6 is the scanning image of an antibody array of stem cell conditioned medium under both optimum serum-free culture and cryopreservation conditions.

FIG. 6 is photographs of the scanned antibody array data, and the analysis results are shown in Table 2 below.

TABLE 2

| ID | Antibody Name | Normalized data (log2) | Raw data | SwissProt | Length | Protein family |
|---|---|---|---|---|---|---|
| 1 | Actin-alpha-1 | 10.19 | 1172 | P68133 | 377 | Actin family |
| 2 | Actin-gamma2 | 8.24 | 303 | P63267 | 376 | Actin family |
| 3 | Actin-pan | 8.29 | 313 | P60709 | 375 | Actin family |
| 4 | Amylin | 7.41 | 170 | P10997 | 89 | Calcitonin family |
| 5 | Annexin A6 | 7.38 | 167 | P08133 | 673 | Annexin family |
| 6 | AP-2 | 7.48 | 178.5 | P05549 | 437 | AP-2 family |
| 7 | APAF-1-ALT | 7.25 | 152 | O14727 | 1248 | — |
| 8 | APC | 7.63 | 198.5 | P25054 | 2843 | Adenomatous polyposis coli (APC) family |
| 9 | ARC | 9.62 | 788 | O60936 | 219 | — |
| 10 | Bak | 7.35 | 163.5 | Q16611 | 211 | Bcl-2 family |
| 11 | Bax | 7.5 | 181 | Q07812 | 192 | Bcl-2 family |
| 12 | BIM | 7.38 | 166.5 | O43521 | 198 | Bcl-2 family |
| 13 | Caspase 10 | 7.24 | 151.5 | Q92851 | 521 | Peptidase C14A family |
| 14 | CARD6 | 7.42 | 171.5 | Q9BX69 | 1037 | — |
| 15 | Catenin-alpha1 | 7.72 | 210.5 | P35221 | 906 | Vinculin/alpha-catenin family |
| 16 | Catenin-gamma | 8.15 | 284.5 | P14923 | 745 | Beta-catenin family |
| 17 | NM23 | 7.43 | 172 | P22392 | 152 | NDK family |
| 18 | Nrf2 | 7.04 | 131.5 | Q16236 | 605 | BZIP family, CNC subfamily |
| 19 | NSE | 6.99 | 127.5 | P09104 | 434 | Enolase family |
| 20 | Octamer-binding transcription factor 1 | 7.37 | 165.5 | P14859 | 743 | POU transcription factor family, Class-2 subfamily |
| 21 | Octamer-binding transcription factor 2 | 7.29 | 156 | P09086 | 479 | POU transcription factor family, Class-2 subfamily |
| 22 | Octamer-binding transcription factor 3 | 7.19 | 146.5 | Q01860 | 360 | POU transcription factor family, Class-5 subfamily |
| 23 | Osteopontin | 7.14 | 141 | P10451 | 314 | Osteopontin family |
| 24 | p16 INK | 7.38 | 166 | P42771 | 156 | CDKN2 cyclin-dependent kinase inhibitor family |
| 25 | p14 ARF | 7.28 | 155 | Q8N726 | 132 | — |
| 26 | p15 INK | 7.39 | 168 | P42772 | 138 | CDKN2 cyclin-dependent kinase inhibitor family |
| 27 | p18 INK | 7.45 | 175 | P42773 | 168 | CDKN2 cyclin-dependent kinase inhibitor family |
| 28 | p300 | 7.29 | 156.5 | Q09472 | 2414 | — |
| 29 | p300/CBP | 7.33 | 160.5 | Q92831 | 832 | acetyltransferase family. GCN5 subfamily. |
| 30 | p50 Dynamitin | 7.28 | 155 | Q13561 | 401 | Dynactin subunit 2 family |
| 31 | p63 | 7.09 | 136.5 | Q9H3D4 | 680 | P53 family |
| 32 | Parathyroid Hormone | 7.33 | 161 | P01270 | 115 | Parathyroid hormone family |
| 33 | Parkin | 7.42 | 171 | O60260 | 465 | RBR family, Parkin subfamily |
| 34 | Cyclin L1 | 6.85 | 115 | Q9UK58 | 526 | Cyclin family, Cyclin L subfamily |
| 35 | Patched | 7.89 | 237 | Q13635 | 1447 | Patched family |
| 36 | Histone 1F0 | 7.38 | 167 | P07305 | 194 | Histone H1/H5 family |
| 37 | FES | 7.66 | 202 | P07332 | 822 | Protein kinase superfamily, Tyr protein kinase family, Fes/fps subfamily |
| 38 | Adrenergic Receptor alpha-2A | 7.15 | 142 | P08913 | 450 | G-protein coupled receptor 1 family, Adrenergic receptor subfamily, ADRA2A sub-subfamily |
| 39 | HMGB1 | 7.44 | 174 | P09429 | 215 | HMGB family |
| 40 | FGR | 7.67 | 203.5 | P09769 | 529 | Protein kinase superfamily, Tyr protein kinase family, SRC subfamily |

TABLE 2-continued

| ID | Antibody Name | Normalized data (log2) | Raw data | SwissProt | Length | Protein family |
|---|---|---|---|---|---|---|
| 41 | DNA Polymerase alpha | 7.2 | 147.5 | P09884 | 1462 | DNA polymerase type-B family |
| 42 | KAP0 | 7.91 | 240.5 | P10644 | 381 | CAMP-dependent kinase regulatory chain family |
| 43 | TOP2A | 7.41 | 170 | P11388 | 1531 | Type II topoisomerase family |
| 44 | UNG | 7.81 | 224.5 | P13051 | 313 | Uracil-DNA glycosylase family |
| 45 | Histone H2AX? | 7.78 | 220 | P16104 | 143 | Histone H2A family |
| 46 | TACD1 | 7.95 | 248 | P16422 | 314 | EPCAM family |
| 47 | ATF7 | 7.65 | 201 | P17544 | 494 | BZIP family |
| 48 | Adrenergic Receptor alpha-2B | 7.61 | 196 | P18089 | 450 | G-protein coupled receptor 1 family, Adrenergic receptor subfamily, ADRA2B sub-subfamily |
| 49 | Adrenergic Receptor alpha-2C | 7.58 | 192 | P18825 | 462 | G-protein coupled receptor 1 family, Adrenergic receptor subfamily, ADRA2C sub-subfamily |
| 50 | ATF1 | 7.45 | 175 | P18846 | 271 | BZIP family, ATF subfamily |
| 51 | ATF3 | 7.38 | 166 | P18847 | 181 | BZIP family, ATF subfamily |
| 52 | Elk1 | 7.29 | 156 | P19419 | 428 | ETS family |
| 53 | TBP | 7.02 | 130 | P20226 | 339 | TBP family |
| 54 | TNF Receptor II | 8.04 | 263.5 | P20333 | 461 | — |
| 55 | SLK | 7.25 | 152.5 | Q9H2G2 | 1235 | Protein kinase superfamily, STE Ser/Thr protein kinase family, STE20 subfamily |
| 56 | MUC13 | 7.76 | 217.5 | Q9H3R2 | 511 | — |
| 57 | CDCP1 | 7.73 | 213 | Q9H5V8 | 836 | — |
| 58 | CKI-gamma1 | 7.6 | 194 | Q9HCP0 | 422 | Protein kinase superfamily, CK1 Ser/Thr protein kinase family, Casein kinase I subfamily |
| 59 | BRMS1 | 7.34 | 162 | Q9HCU9 | 246 | BRMS1 family |
| 60 | BCA3 | 7.5 | 181 | Q9NQ31 | 210 | — |
| 61 | TSH2 | 7.54 | 186.5 | Q9NRE2 | 1034 | Teashirt C2H2-type zinc-finger protein family |
| 62 | SERC1 | 7.54 | 186 | Q9NRX5 | 453 | TDE1 family |
| 63 | CREBZF | 7.37 | 165.5 | Q9NS37 | 354 | BZIP family, ATF subfamily |
| 64 | EKI2 | 7.58 | 192 | Q9NVF9 | 386 | Choline/ethanolamine kinase family |
| 65 | FAKD2 | 7.44 | 173.5 | Q9NYY8 | 710 | FAST kinase family |
| 66 | MARK | 7.97 | 250 | Q9P0L2 | 795 | Protein kinase superfamily, CAMK Ser/Thr protein kinase family, SNF1 subfamily |
| 67 | HMG20B | 7.63 | 198 | Q9P0W2 | 317 | — |
| 68 | LW-1 | 7.34 | 161.5 | Q9UBD0 | 423 | HSF family |
| 69 | MRC2 | 7.41 | 170.5 | Q9UBG0 | 1479 | — |
| 70 | DNA Polymerase lambda | 7.41 | 169.5 | Q9UGP5 | 575 | DNA polymerase type-X family |
| 71 | KLHL3 | 7.84 | 229.5 | Q9UH77 | 587 | — |
| 72 | Mlx | 7.81 | 224 | Q9UH92 | 298 | Transcription |
| 73 | IP6K2 | 7.02 | 130 | Q9UHH9 | 426 | kinase |
| 74 | PARK7 | 7.01 | 128.5 | Q99497 | 189 | Peptidase C56 family |
| 75 | PARP3 | 7.06 | 133.5 | Q9Y6F1 | 533 | — |
| 76 | PHLA1 | 7.86 | 233 | Q8WV24 | 401 | — |
| 77 | PRPF19 | 7.48 | 178.5 | Q9UMS4 | 504 | WD repeat PRP19 family |
| 78 | RAD51L1 | 7.47 | 177.5 | O15315 | 384 | RecA family, RAD51 subfamily |
| 79 | RAD50 | 7.33 | 161 | Q92878 | 1312 | SMC family, RAD50 subfamily |
| 80 | XRCC3 | 7.28 | 155.5 | O43542 | 346 | RecA family, RAD51 subfamily |
| 81 | STAT5A/B | 8.84 | 458 | P42229 | 794 | Transcription factor STAT family |
| 82 | ABHD11 | 7.25 | 152 | Q8NFV4 | 315 | AB hydrolase superfamily |
| 83 | ABHD12 | 7.41 | 170 | Q8N2K0 | 398 | Serine esterase family |
| 84 | ABHD12B | 7.81 | 224.5 | Q7Z5M8 | 362 | Serine esterase family |
| 85 | ABHD14A | 7.28 | 155 | Q9BUJ0 | 271 | AB hydrolase superfamily, ABHD14 family |
| 86 | ABHD14B | 7.28 | 155.5 | Q96IU4 | 210 | AB hydrolase superfamily, ABHD14 family |
| 87 | ABHD4 | 7.2 | 147 | Q8TB40 | 342 | Peptidase S33 family, ABHD4/ABHD5 subfamily |
| 88 | ACTR3 | 7.38 | 167 | P61158 | 418 | Actin family, ARP3 subfamily |
| 89 | SLC25A6 | 7.12 | 139.5 | P12236 | 298 | Mitochondrial carrier family |
| 90 | SLC25A31 | 7.24 | 151.5 | Q9H0C2 | 315 | Mitochondrial carrier family |
| 91 | ADH7 | 7.3 | 158 | P40394 | 386 | Zinc-containing alcohol dehydrogenase family, Class-IV subfamily |
| 92 | ALDH3B1 | 7.09 | 136.5 | P43353 | 468 | Aldehyde dehydrogenase family |
| 93 | SAR1B | 7.07 | 134.5 | Q9Y6B6 | 198 | Small GTPase superfamily, SAR1 family |
| 94 | GNL3L | 7.09 | 136.5 | Q9NVN8 | 582 | MMR1/HSR1 GTP-binding protein family |
| 95 | HLAH | 7.16 | 143 | P01893 | 362 | MHC class I family |
| 96 | HLA-DOA | 7.14 | 141.5 | P06340 | 250 | MHC class II family |
| 97 | HOXA11/D11 | 7.5 | 181.5 | P31270 | 313 | Abd-B homeobox family |
| 98 | HOXA6 | 7.15 | 142.5 | P31267 | 233 | Antp homeobox family |
| 99 | HOXB2 | 7.19 | 146 | P14652 | 356 | Antp homeobox family, Proboscipedia subfamily |
| 100 | NKX26 | 7.23 | 150 | A6NCS4 | 301 | NK-2 homeobox family |
| 101 | SIX5 | 7.12 | 139 | Q8N196 | 739 | SIX/Sine oculis homeobox family |
| 102 | IGLL1 | 7.07 | 134 | P15814 | 213 | — |
| 103 | USP53 | 7.22 | 149.5 | Q70EK8 | 1073 | Peptidase C19 family |

TABLE 2-continued

| ID | Antibody Name | Normalized data (log2) | Raw data | SwissProt | Length | Protein family |
|---|---|---|---|---|---|---|
| 104 | KCNJ2 | 7.31 | 158.5 | P63252 | 427 | Inward rectifier-type potassium channel (TC 1.A.2.1) family, KCNJ2 subfamily |
| 105 | DCT | 7.11 | 138.5 | P40126 | 519 | Tyrosinase family |
| 106 | LILRA1 | 7.08 | 135.5 | O75019 | 489 | — |
| 107 | LILRA2 | 7.2 | 147 | Q8N149 | 483 | — |
| 108 | SLC27A4 | 7.28 | 155 | Q6P1M0 | 643 | ATP-dependent AMP-binding enzyme family |
| 109 | LDLRAD1 | 7.04 | 132 | Q5T700 | 205 | LDLR family |
| 110 | LDLRAD2 | 7.18 | 145 | Q5SZI1 | 272 | LDLR family |
| 111 | LDLRAD3 | 7.35 | 163.5 | Q86YD5 | 345 | LDLR family |
| 112 | SLC5A3 | 7.13 | 140 | P53794 | 718 | Sodium:solute symporter (SSF) (TC 2.A.21) family |
| 113 | SLC28A2 | 7.05 | 132.5 | O43868 | 658 | Concentrative nucleoside transporter (CNT) (TC 2.A.41) family |
| 114 | SLC24A4 | 7.11 | 138.5 | Q8NFF2 | 622 | Sodium/potassium/calcium exchanger family, SLC24A subfamily |
| 115 | SLC24A6 | 7.39 | 168 | Q6J4K2 | 584 | Sodium/potassium/calcium exchanger family, SLC24A subfamily |
| 116 | SLC5A6 | 7.32 | 159.5 | Q9Y289 | 635 | Sodium:solute symporter (SSF) (TC 2.A.21) family |
| 117 | SLC17A2 | 7.1 | 137.5 | O00624 | 439 | Major facilitator superfamily, Sodium/anion cotransporter family |
| 118 | SLC4A8/10 | 7.13 | 140.5 | Q6U841 | 1118 | Anion exchanger (TC 2.A.31) family |
| 119 | SLCO1A2 | 7.22 | 149.5 | P46721 | 670 | Organo anion transporter (TC 2.A.60) family |
| 120 | SPTBN1 | 7.31 | 158.5 | Q01082 | 2364 | Spectrin family |
| 121 | SPTBN5 | 7.04 | 132 | Q9NRC6 | 3674 | Spectrin family |
| 122 | STMN4 | 7.24 | 151 | Q9H169 | 189 | Stathmin family |
| 123 | STK39 | 7.12 | 139 | Q9UEW8 | 545 | Protein kinase superfamily, STE Ser/Thr protein kinase family, STE20 subfamily |
| 124 | SVOP | 7.09 | 136 | Q8N4V2 | 548 | Major facilitator superfamily |
| 125 | CCT6A | 7.24 | 151.5 | P40227 | 531 | TCP-1 chaperonin family |
| 126 | TNXB | 7.08 | 135.5 | P22105 | 4289 | Tenascin family |
| 127 | USP13 | 7.09 | 136.5 | Q92995 | 863 | Peptidase C19 family |
| 128 | USP19 | 7.11 | 138.5 | O94966 | 1318 | Peptidase C19 family |
| 129 | USP24 | 7.17 | 144 | Q9UPU5 | 2620 | Peptidase C19 family |
| 130 | USP30 | 7.54 | 186.5 | Q70CQ3 | 517 | Peptidase C19 family |
| 131 | Nucleophosmin (NPM) | 7.15 | 142 | Q9BYG9 | 294 | nucleoplasmin family |
| 132 | BCL-10 | 7.15 | 142.5 | O95999 | 233 | — |
| 133 | CD8 | 7.12 | 139 | P01732/P10966 | — | — |
| 134 | IFN-gamma | 7.09 | 136.5 | P01579 | 166 | Type II (or gamma) interferon family |
| 135 | IL-10 | 7.22 | 149.5 | P22301 | 178 | IL-10 family |
| 136 | IL-8 | 7.18 | 145.5 | P10145 | 99 | Intercrine alpha (chemokine CxC) family |
| 137 | CD14 | 7.2 | 147 | P08571 | 375 | — |
| 138 | IL-6 | 7.22 | 149 | P05231 | 212 | IL-6 superfamily |
| 139 | CD10 | 7.23 | 150 | P08473 | 750 | Peptidase M13 family |
| 140 | CD3 | 7.21 | 148 | P20963/P09693 | — | — |
| 141 | MCL-1 | 7.16 | 143 | Q07820 | 350 | Bcl-2 family |
| 142 | CD19 | 7.22 | 149 | P15391 | 556 | — |
| 143 | CHK1 | 7.22 | 149 | O14757 | 476 | Protein kinase superfamily, CAMK Ser/Thr protein kinase family, NIM1 subfamily |
| 144 | Foxp3 | 7.24 | 151 | B7ZLG1 | 454 | — |
| 145 | Rab25 | 7.19 | 146.5 | P57753 | 525 | Nuclear hormone receptor family, NR3 subfamily |
| 146 | cTnI (TNNI3) | 7.23 | 150 | P19429 | 210 | Troponin I family |
| 147 | Calcyclin (S100A6) | 7.2 | 147.5 | P06703 | 90 | S-100 family |
| 148 | HPRT | 7.13 | 140 | P00492 | 218 | Purine/pyrimidine phosphoribosyltransferase family |
| 149 | Dynamin-1 | 7.08 | 135 | Q05193 | 864 | Dynamin family |
| 150 | p53 (Acetyl-Lys386) | 7.34 | 162.5 | P04637 | 393 | p53 family |
| 151 | NF-kB p65 (Acetyl-Lys310) | 7.6 | 194.5 | Q04206 | 551 | — |
| 152 | GPR120 | 7.39 | 167.5 | Q5NUL3 | 377 | G-protein coupled receptor 1 family |
| 153 | GPR150 | 7.35 | 163 | Q8NGU9 | 434 | G-protein coupled receptor 1 family |
| 154 | GPR151 | 8.46 | 351.5 | Q8TDV0 | 419 | G-protein coupled receptor 1 family |
| 155 | GPR152 | 7.41 | 170 | Q8TDT2 | 470 | G-protein coupled receptor 1 family |
| 156 | GPR153 | 7.69 | 206 | Q6NV75 | 609 | G-protein coupled receptor 1 family |
| 157 | GPR160 | 7.3 | 158 | Q9UJ42 | 338 | G-protein coupled receptor 1 family |
| 158 | GPR171 | 7.25 | 152.5 | O14626 | 319 | G-protein coupled receptor 1 family |
| 159 | GPR173 | 7.51 | 182.5 | Q9NS66 | 373 | G-protein coupled receptor 1 family |
| 160 | GPR174 | 7.24 | 151.5 | Q9BXC1 | 333 | G-protein coupled receptor 1 family |
| 161 | CBP (Acetyl-Lys1535) | 7.09 | 136 | Q92793 | 2442 | — |
| 162 | EMR1 | 7.21 | 148 | Q14246 | 886 | G-protein coupled receptor 2 family, LN-TM7 subfamily |
| 163 | EMR2 | 7.11 | 138 | Q9UHX3 | 823 | G-protein coupled receptor 2 family, LN-TM7 subfamily |

TABLE 2-continued

| ID | Antibody Name | Normalized data (log2) | Raw data | SwissProt | Length | Protein family |
|---|---|---|---|---|---|---|
| 164 | EMR3 | 8.46 | 351.5 | Q98Y15 | 652 | G-protein coupled receptor 2 family, LN-TM7 subfamily |
| 165 | GPR132 | 8.16 | 287 | Q9UNW8 | 380 | G-protein coupled receptor 1 family |
| 166 | GPR175 | 7.31 | 159 | Q86W33 | 373 | UPF0359 family |
| 167 | GPR18 | 7.2 | 147 | Q14330 | 331 | G-protein coupled receptor 1 family |
| 168 | Caspase 6 (Cleaved-Asp162) | 7.73 | 212 | P55212 | 293 | Peptidase C14A family |
| 169 | Caveolin-1 | 8.65 | 401.5 | Q03135 | 178 | Caveolin family |
| 170 | Claudin 4 | 7.58 | 191 | O14493 | 209 | Claudin family |
| 171 | Claudin 1 | 7.31 | 158.5 | O95832 | 211 | Claudin family |
| 172 | Claudin 2 | 7.6 | 194 | P57739 | 230 | Claudin family |
| 173 | Claudin 3 | 7.92 | 241.5 | O15551 | 220 | Claudin family |
| 174 | Claudin 5 | 9.22 | 596 | O00501 | 218 | Claudin family |
| 175 | CSE1L | 7.64 | 199 | P55060 | 971 | XPO2/CSE1 family |
| 176 | E-cadherin | 7.59 | 192.5 | P12830 | 882 | — |
| 177 | Cadherin-pan | 7.55 | 188 | P12830 | 882 | — |
| 178 | Fos | 7.82 | 226 | P01100 | 380 | BZIP family, Fos subfamily |
| 179 | HER3 | 8.36 | 329.5 | P21860 | 1342 | Protein kinase superfamily, Tyr protein kinase family, EGF receptor subfamily |
| 180 | Claudin 10 | 7.83 | 228 | P78369 | 228 | Claudin family |
| 181 | Claudin 11 | 7.76 | 217 | O75508 | 207 | Claudin family |
| 182 | Claudin 7 | 7.58 | 192 | O95471 | 211 | Claudin family |
| 183 | Collagen I | 7.54 | 186.5 | P08123 | 1366 | Fibrillar collagen family |
| 184 | Collagen II | 7.45 | 175 | P02458 | 1487 | Fibrillar collagen family |
| 185 | Collagen III | 8.84 | 458.5 | P02461 | 1466 | Fibrillar collagen family |
| 186 | Collagen IV | 7.89 | 237 | P02462 | 1669 | Type IV collagen family |
| 187 | Connexin 43 | 7.47 | 177 | P17302 | 382 | Connexin family, Alpha-type (group II) subfamily |
| 188 | Pax-5 | 7.92 | 242 | Q02548 | 391 | — |
| 189 | PCNA | 7.22 | 149 | P12004 | 261 | PCNA family |
| 190 | PDGFB | 7.28 | 155 | P01127 | 241 | PDGF/VEGF growth factor family |
| 191 | PDGFR alpha | 7.41 | 169.5 | P16234 | 1089 | Protein kinase superfamily, Tyr protein kinase family, CSF-1/PDGF receptor subfamily |
| 192 | Peripherin | 10.26 | 1224 | P41219 | 470 | Intermediate filament family |
| 193 | PGP9.5 | 7.22 | 149.5 | P09936 | 223 | Peptidase C12 family |
| 194 | PML | 7.4 | 169 | P29590 | 882 | — |
| 195 | PMP22 | 7.44 | 174 | Q01453 | 160 | PMP-22/EMP/MP20 family |
| 196 | Potassium Channel Kv3.2b | 7.41 | 170.5 | Q96PR1 | 638 | Potassium channel family, C (Shaw) (TC 1.A.1.2) subfamily, Kv3.2/KCNC2 sub-subfamily |
| 197 | Presenilin 1 | 7.35 | 163.5 | P49768 | 467 | Peptidase A22A family |
| 198 | Prostate Apoptosis Response protein-4 | 7.16 | 143 | Q96IZ0 | 340 | — |
| 199 | Prostate Stem Cell Antigen | 7.2 | 147 | O43653 | 123 | — |
| 200 | Prostate-specific Antigen | 7.2 | 147.5 | P07288 | 261 | Peptidase S1 family, Kallikrein subfamily |
| 201 | RAN | 7.16 | 143 | P62826 | 216 | Small GTPase superfamily, Ran family |
| 202 | RASH/RASK | 7.47 | 177 | P01112 | 189 | Small GTPase superfamily, Ras family |
| 203 | RCBTB1 | 7.74 | 213.5 | Q8NDN9 | 531 | — |
| 204 | Retinoic Acid Receptor beta | 7.7 | 208.5 | P10826 | 455 | Nuclear hormone receptor family, NR1 subfamily |
| 205 | Retinoid X Receptor gamma | 7.34 | 161.5 | P48443 | 463 | Nuclear hormone receptor family, NR2 subfamily |
| 206 | RIT1 | 7.55 | 187 | Q92963 | 219 | Small GTPase superfamily, Ras family |
| 207 | EPHA1 | 7.61 | 195.5 | P21709 | 976 | Protein kinase superfamily, Tyr protein kinase family, Ephrin receptor subfamily |
| 208 | S6K | 8.25 | 303.5 | P23443 | 525 | Protein kinase superfamily, AGC Ser/Thr protein kinase family, S6 kinase subfamily |
| 209 | JAK1 | 7.12 | 139.5 | P23458 | 1154 | Protein kinase superfamily, Tyr protein kinase family, JAK subfamily |
| 210 | TNFL4 | 7.41 | 170.5 | P23510 | 183 | Tumor necrosis factor family |
| 211 | IP3KA | 7.52 | 183 | P23677 | 461 | Inositol phosphokinase (IPK) family |
| 212 | COT2 | 7.46 | 176 | P24468 | 414 | Nuclear hormone receptor family, NR2 subfamily |
| 213 | CDK2 | 7.4 | 169 | P24941 | 298 | Protein kinase superfamily, CMGC Ser/Thr protein kinase family, CDC2/CDKX subfamily |
| 214 | HMGB2 | 7.34 | 162.5 | P26583 | 209 | HMGB family |
| 215 | p44 MAPK | 7.64 | 199 | P27361 | 379 | Protein kinase superfamily, CMGC Ser/Thr protein kinase family, MAP kinase subfamily |
| 216 | p42 MAPK | 9.37 | 662.5 | P28482 | 360 | Protein kinase superfamily, CMGC Ser/Thr protein kinase family, MAP kinase subfamily |

TABLE 2-continued

| ID | Antibody Name | Normalized data (log2) | Raw data | SwissProt | Length | Protein family |
|---|---|---|---|---|---|---|
| 217 | ERCC5 | 7.25 | 152.5 | P28715 | 1186 | XPG/RAD2 endonuclease family, XPG subfamily |
| 218 | EPHB2 | 7.35 | 163.5 | P29323 | 1055 | Protein kinase superfamily, Tyr protein kinase family, Ephrin receptor subfamily |
| 219 | Akt | 7.47 | 177.5 | P31749 | 480 | Protein kinase superfamily, AGC Ser/Thr protein kinase family, RAC subfamily |
| 220 | CD153 | 7.34 | 162.5 | P32971 | 234 | Tumor necrosis factor family |
| 221 | GRK5 | 7.11 | 138 | P34947 | 590 | Protein kinase superfamily, AGC Ser/Thr protein kinase family, GPRK subfamily |
| 222 | RORA | 7.61 | 195.5 | P35398 | 556 | Nuclear hormone receptor family, NR1 subfamily |
| 223 | GRK3 | 7.47 | 177.5 | P35626 | 688 | Protein kinase superfamily, AGC Ser/Thr protein kinase family, GPRK subfamily |
| 224 | ATP7B | 7.34 | 161.5 | P35670 | 1465 | Cation transport ATPase (P-type) (TC 3.A.3) family, Type IB subfamily |
| 225 | CSK | 7.24 | 151.5 | P41240 | 450 | Protein kinase superfamily, Tyr protein kinase family, CSK subfamily |
| 226 | CARKL | 7.1 | 137.5 | Q9UHJ6 | 478 | FGGY kinase family |
| 227 | STAG3 | 7.38 | 166.5 | Q9UJ98 | 1225 | SCC3 family |
| 228 | S6K-alpha6 | 7.13 | 140.5 | Q9UK32 | 745 | Protein kinase superfamily, AGC Ser/Thr protein kinase family, S6 kinase subfamily |
| 229 | Mucin-14 | 7.25 | 152.5 | Q9ULC0 | 261 | — |
| 230 | PKCB1 | 7.26 | 153 | Q9ULU4 | 1186 | — |
| 231 | ASC | 7.49 | 180 | Q9ULZ3 | 195 | — |
| 232 | MOK | 7.23 | 150 | Q9UQ07 | 419 | Protein kinase superfamily, CMGC Ser/Thr protein kinase family, CDC2/CDKX subfamily |
| 233 | DLEC1 | 7.36 | 164.5 | Q9Y238 | 1755 | — |
| 234 | CHKB | 7.6 | 194 | Q9Y259 | 395 | Choline/ethanolamine kinase family |
| 235 | ATF5 | 7.28 | 155.5 | Q9Y2D1 | 282 | BZIP family |
| 236 | ATG4B | 7.41 | 169.5 | Q9Y4P1 | 393 | Peptidase C54 family |
| 237 | MRCKB | 7.18 | 145.5 | Q9Y5S2 | 1711 | Protein kinase superfamily, AGC Ser/Thr protein kinase family, DMPK subfamily |
| 238 | IRAK3 | 7.34 | 162.5 | Q9Y616 | 596 | Protein kinase superfamily, TKL Ser/Thr protein kinase family, Pelle subfamily |
| 239 | TAF6L | 7.25 | 152 | Q9Y6J9 | 622 | TAF6 family |
| 240 | IKK-gamma | 7.59 | 193 | Q9Y6K9 | 419 | — |
| 241 | ZHX2 | 7.28 | 155.5 | Q9Y6X8 | 837 | ZHX family |
| 242 | 14-3-3 eta | 7.21 | 148.5 | Q04917 | 246 | 14-3-3 family |
| 243 | 14-3-3 gamma | 7.19 | 146 | P61981 | 247 | 14-3-3 family |
| 244 | 14-3-3 zeta | 7.28 | 155.5 | P63104 | 245 | 14-3-3 family |
| 245 | ALDH1B1 | 7.36 | 164 | P30837 | 517 | Aldehyde dehydrogenase family |
| 246 | AKR1CL1 | 7.07 | 134.5 | Q5T2L2 | 129 | Aldo/keto reductase family |
| 247 | AKR1CL2 | 7.21 | 148 | Q96JD6 | 320 | Aldo/keto reductase family |
| 248 | AKR1B1 | 7.29 | 156.5 | P15121 | 316 | Aldo/keto reductase family |
| 249 | AMPD1 | 7.37 | 165 | P23109 | 780 | Adenosine and AMP deaminases family |
| 250 | APLP2 | 7.23 | 150.5 | Q06481 | 763 | APP family |
| 251 | AIG1 | 7.25 | 152.5 | Q9NVV5 | 245 | AIG1 family |
| 252 | APOF | 7.12 | 139 | Q13790 | 326 | — |
| 253 | APOL1 | 7.14 | 141.5 | O14791 | 398 | Apolipoprotein L family |
| 254 | APOL2 | 7.2 | 147 | Q9BQE5 | 337 | Apolipoprotein L family |
| 255 | ARFIP1 | 8.42 | 343 | P53367 | 373 | — |
| 256 | ARSA | 7.34 | 162.5 | P15289 | 507 | Sulfatase family |
| 257 | ARSD | 7.19 | 146 | P51689 | 593 | Sulfatase family |
| 258 | ARSI | 7.95 | 247.5 | Q5FYB1 | 569 | Sulfatase family |
| 259 | ARSK | 7.35 | 163.5 | Q6UWY0 | 536 | Sulfatase family |
| 260 | ATP5H | 7.64 | 199 | O75947 | 161 | ATPase d subunit family |
| 261 | ATP5D | 7.49 | 179.5 | P30049 | 168 | ATPase epsilon chain family |
| 262 | ATPG | 7.24 | 151.5 | P36542 | 298 | ATPase gamma chain family |
| 263 | ATP5G2 | 7.32 | 160 | Q06055 | 141 | ATPase C chain family |
| 264 | LRP10 | 7.04 | 132 | Q7Z4F1 | 713 | LDLR family |
| 265 | LRP11 | 7.29 | 156 | Q86VZ4 | 500 | LDLR family |
| 266 | LRP3 | 7.26 | 153.5 | O75074 | 770 | LDLR family |
| 267 | LAMP3 | 7.34 | 161.5 | Q9UQV4 | 416 | LAMP family |
| 268 | MRP9 | 7.42 | 171.5 | Q96J65 | 1359 | ABC transporter superfamily, ABCC family, Conjugate transporter (TC 3.A.1.208) subfamily |
| 269 | MDFI | 7.65 | 200.5 | Q99750 | 246 | MDFI family |
| 270 | MYOM1 | 7.23 | 150 | P52179 | 1685 | — |
| 271 | MYOM2 | 7.21 | 148.5 | P54296 | 1465 | — |
| 272 | MPRIP | 7.26 | 153.5 | Q6WCQ1 | 1025 | — |
| 273 | MYH14 | 7.11 | 138 | Q7Z406 | 1995 | — |
| 274 | MYH4 | 7.15 | 142.5 | Q9Y623 | 1939 | TRAFAC class myosin-kinesin ATPase superfamily. Myosin family |

TABLE 2-continued

| ID | Antibody Name | Normalized data (log2) | Raw data | SwissProt | Length | Protein family |
|---|---|---|---|---|---|---|
| 275 | MYBPC3 | 7.13 | 140 | Q14896 | 1273 | Immunoglobulin superfamily, MyBP family |
| 276 | MYO1D | 7.44 | 174 | O94832 | 1006 | TRAFAC class myosin-kinesin ATPase superfamily. Myosin family |
| 277 | CYB5R1 | 7.29 | 156.5 | Q9UHQ9 | 305 | Flavoprotein pyridine nucleotide cytochrome reductase family |
| 278 | CYB5R3 | 7.28 | 155 | P00387 | 301 | Flavoprotein pyridine nucleotide cytochrome reductase family |
| 279 | ME1 | 7.2 | 147.5 | P48163 | 572 | Malic enzymes family |
| 280 | ME3 | 7.07 | 134 | Q16798 | 604 | Malic enzymes family |
| 281 | NOX3 | 7.34 | 162 | Q9HBY0 | 568 | — |
| 282 | NOX5 | 7.51 | 182 | Q96PH1 | 765 | — |
| 283 | USP32 | 7.4 | 169 | Q8NFA0 | 1604 | Peptidase C19 family |
| 284 | USP36 | 7.04 | 132 | Q9P275 | 1121 | Peptidase C19 family |
| 285 | USP42 | 7.1 | 137 | Q9H9J4 | 1324 | Peptidase C19 family |
| 286 | UBTD1 | 7.08 | 135 | Q9HAC8 | 227 | — |
| 287 | UBFD1 | 7.1 | 137 | O14562 | 309 | — |
| 288 | UBA5 | 7.37 | 165.5 | Q9GZZ9 | 404 | Ubiquitin-activating E1 family, UBA5 subfamily |
| 289 | UBAC1 | 7.08 | 135.5 | Q9BSL1 | 405 | — |
| 290 | UBAP2L | 7.08 | 135.5 | Q14157 | 1087 | — |
| 291 | UBE3B | 7.38 | 167 | Q7Z3V4 | 1068 | — |
| 292 | USP6NL | 7.08 | 135 | Q92738 | 828 | — |
| 293 | ATP6V1B1 | 7.27 | 154 | P15313 | 513 | ATPase alpha/beta chains family |
| 294 | ATP6V1H | 7.15 | 142.5 | Q9UI12 | 483 | V ATPase H subunit family |
| 295 | VANGL1 | 7.15 | 142 | Q8TAA9 | 524 | Vang family |
| 296 | WDHD1 | 7.32 | 160 | O75717 | 1129 | — |
| 297 | WASF3 | 7.13 | 140.5 | Q9UPY6 | 502 | SCAR/WAVE family |
| 298 | WASF4 | 7.35 | 163 | Q8IV90 | | — |
| 299 | SLC30A1 | 7.14 | 141.5 | Q9Y6M5 | 507 | Cation diffusion facilitator (CDF) transporter (TC 2.A4) family, SLC30A subfamily |
| 300 | SLC30A4 | 7.54 | 185.5 | O14863 | 429 | Cation diffusion facilitator (CDF) transporter (TC 2.A.4) family, SLC30A subfamily |
| 301 | SLC30A8 | 7.53 | 184.5 | Q8IWU4 | 369 | Cation diffusion facilitator (CDF) transporter (TC 2.A.4) family, SLC30A subfamily |
| 302 | SRA | 7.06 | 133.5 | Q9HD15 | 236 | SRA1 family |
| 303 | SNCA (alpha-synuclein) | 7.05 | 132.5 | P37840 | 140 | Synuclein family |
| 304 | Akt3 | 7.11 | 138 | Q9Y243 | 479 | Protein kinase superfamily, AGC Ser/Thr protein kinase family, RAC subfamily |
| 305 | Fibulin 5 | 7.11 | 138 | Q9UBX5 | 448 | Fibulin family |
| 306 | Lck | 7.15 | 142.5 | P06239 | 509 | Protein kinase superfamily, Tyr protein kinase family, SRC subfamily |
| 307 | ATP2C1 | 7.16 | 143 | P98194 | 919 | Cation transport ATPase (P-type) (TC 3.A.3) family, Type IIA subfamily |
| 308 | BLK | 7.24 | 151 | P51451 | 505 | Protein kinase superfamily, Tyr protein kinase family, SRC subfamily |
| 309 | Tyk2 | 7.23 | 150.5 | P29597 | 1187 | Protein kinase superfamily, Tyr protein kinase family, JAK subfamily |
| 310 | ERK2 | 7.16 | 143.5 | P28482 | 360 | Protein kinase superfamily, CMGC Ser/Thr protein kinase family, MAP kinase subfamily |
| 311 | Myoglobin | 7.18 | 145 | P02144 | 154 | Globin family |
| 312 | GADD45 beta | 7.27 | 154 | O75293 | 160 | GADD45 family |
| 313 | MAP2K4 | 7.19 | 146.5 | P45985 | 399 | Protein kinase superfamily, STE Ser/Thr protein kinase family, MAP kinase kinase subfamily |
| 314 | EGFR | 7.14 | 141.5 | P00533 | 1210 | Protein kinase superfamily, Tyr protein kinase family, EGF receptor subfamily |
| 315 | 4E-BP1 | 7.18 | 145.5 | Q13541 | 118 | EIF4E-binding protein family |
| 316 | INHA (Inhibin alpha) | 7.2 | 147 | P05111 | 366 | TGF-beta family |
| 317 | Dynamin-2 | 7.18 | 145.5 | P50570 | 870 | Dynamin family |
| 318 | IKBKB (IKK beta) | 7.17 | 144.5 | O14920 | 756 | Protein kinase superfamily, Ser/Thr protein kinase family, I-kappa-B kinase subfamily |
| 319 | AURKB | 7.1 | 137.5 | Q96GD4 | 344 | Protein kinase superfamily, Ser/Thr protein kinase family, Aurora subfamily |
| 320 | S100A10/P11 | 7.12 | 139 | P60903 | 97 | S-100 family |
| 321 | Caspase 9 (Cleaved-Asp353) | 7.14 | 141 | Q9R0S9 | 393 | Peptidase C14A family |
| 322 | Caspase 9 (Cleaved-Asp330) | 7.55 | 188 | P55211 | 416 | Peptidase C14A family |
| 323 | Lamin A (Cleaved-Asp230) | 7.2 | 147 | P02545 | 664 | Intermediate filament family |
| 324 | PE2R3 | 7.46 | 175.5 | P43115 | 390 | G-protein coupled receptor 1 family |
| 325 | PE2R4 | 7.04 | 131.5 | P35408 | 488 | G-protein coupled receptor 1 family |

TABLE 2-continued

| ID | Antibody Name | Normalized data (log2) | Raw data | SwissProt | Length | Protein family |
|---|---|---|---|---|---|---|
| 326 | Caspase 7 (Cleaved-Asp198) | 8.03 | 261.5 | P55210 | 303 | Peptidase C14A family |
| 327 | Caspase 9 (Cleaved-Asp315) | 7.4 | 168.5 | P55211 | 416 | Peptidase C14A family |
| 328 | CASP1 (p20, Cleaved-Asn120) | 7.36 | 164 | P29466 | 404 | Peptidase C14A family |
| 329 | CASP2 (p18, Cleaved-Gly170) | 7.41 | 169.5 | P42575 | 452 | Peptidase C14A family |
| 330 | CASP2 (p18, Cleaved-Thr325) | 7.37 | 165 | P42575 | 452 | Peptidase C14A family |
| 331 | CASP4 (p20, Cleaved-Gln81) | 7.43 | 172 | P49662 | 377 | Peptidase C14A family |
| 332 | CASP5 (p20, Cleaved-Asp121) | 7.76 | 216.5 | P51878 | 434 | Peptidase C14A family |
| 333 | CASP5 (p10, Cleaved-Ser331) | 7.6 | 194 | P51878 | 434 | Peptidase C14A family |
| 334 | CASP8 (Cleaved-Asp384) | 7.3 | 158 | Q14790 | 479 | Peptidase C14A family |
| 335 | EFNA2 (Cleaved-Asn188) | 7.44 | 173.5 | O43921 | 213 | Ephrin family |
| 336 | MMP1 (Cleaved-Phe100) | 7.16 | 143.5 | P03956 | 469 | Peptidase M10A family |
| 337 | MMP12 (Cleaved-Glu106) | 7.31 | 159 | P39900 | 470 | Peptidase M10A family |
| 338 | MMP14 (Cleaved-Tyr112) | 7.48 | 178.5 | P50281 | 582 | Peptidase M10A family |
| 339 | MMP15 (Cleaved-Tyr132) | 7.14 | 141 | P51511 | 669 | Peptidase M10A family |
| 340 | COX1 | 7.65 | 201 | P23219 | 599 | Prostaglandin G/H synthase family |
| 341 | COX2 | 7.58 | 192 | P35354 | 604 | Prostaglandin G/H synthase family |
| 342 | CREB-BP | 7.76 | 217 | Q92793 | 2442 | — |
| 343 | Cullin 1 | 8.57 | 380 | Q13616 | 776 | Cullin family |
| 344 | Cullin 2 | 7.53 | 184.5 | Q13617 | 745 | Cullin family |
| 345 | Cullin 3 | 7.58 | 192 | Q13618 | 768 | Cullin family |
| 346 | Cyclin A | 7.83 | 227 | P78396 | 465 | Cyclin family, Cyclin AB subfamily |
| 347 | Cyclin A1 | 7.48 | 178.5 | P78396 | 465 | Cyclin family, Cyclin AB subfamily |
| 348 | Cyclin E1 | 7.5 | 180.5 | P24864 | 410 | Cyclin family, Cyclin E subfamily |
| 349 | Cyclin F | 7.67 | 204 | P41002 | 786 | Cyclin family, Cyclin AB subfamily |
| 350 | Cyclin G | 7.7 | 208.5 | P51959 | 295 | Cyclin family, Cyclin G subfamily |
| 351 | Cytochrome c | 7.65 | 201.5 | P99999 | 105 | Cytochrome c family |
| 352 | Desmin | 11.05 | 2126.5 | P17661 | 470 | Intermediate filament family |
| 353 | DJ-1 | 7.7 | 207.5 | Q99497 | 189 | Peptidase C56 family |
| 354 | DNA Polymerase beta | 7.32 | 160 | P06746 | 335 | DNA polymerase type-X family |
| 355 | DNA-PK | 7.46 | 176 | P78527 | 4128 | PI3/PI4-kinase family |
| 356 | DP-1 | 8.1 | 273.5 | Q14186 | 410 | E2F/DP family |
| 357 | Dysferlin | 7.84 | 229 | O75923 | 2080 | Ferlin family |
| 358 | E2F4 | 7.3 | 157.5 | Q16254 | 413 | E2F/DP family |
| 359 | S100 A1 | 7.95 | 246.5 | P23297 | 94 | S-100 family |
| 360 | SHIP1 | 7.36 | 164.5 | Q92835 | 1189 | Inositol 1,4,5-trisphosphate 5-phosphatase family |
| 361 | SH-PTP2 | 7.4 | 168.5 | Q06124 | 597 | Protein-tyrosine phosphatase family, Non-receptor class 2 subfamily |
| 362 | Sirp alpha1 | 7.36 | 164.5 | P78324 | 504 | — |
| 363 | SKP1A/p19 | 7.62 | 196.5 | P63208 | 163 | SKP1 family |
| 364 | SKP2/p45 | 7.55 | 187 | Q13309 | 424 | — |
| 365 | SNAP25 | 7.22 | 149.5 | P60880 | 206 | SNAP-25 family |
| 366 | Sodium Channel-pan | 7.26 | 153.5 | P35498 | 2009 | Sodium channel (TC 1.A.1.10) family, Nav1.1/SCN1A subfamily |
| 367 | Somatostatin | 7.52 | 184 | P61278 | 116 | Somatostatin family |
| 368 | Stefin A | 7.35 | 163 | P01040 | 98 | Cystatin family |
| 369 | Stefin B | 7.32 | 159.5 | P04080 | 98 | Cystatin family |
| 370 | SYK | 7.26 | 153.5 | P43405 | 635 | Protein kinase superfamily, Tyr protein kinase family, SYK/ZAP-70 subfamily |
| 371 | Synaptophysin | 7.28 | 155.5 | P08247 | 313 | Synaptophysin/synaptobrevin family |
| 372 | Synuclein gamma | 7.23 | 150 | O76070 | 127 | Synuclein family |
| 373 | Synuclein beta | 7.46 | 175.5 | Q16143 | 134 | Synuclein family |
| 374 | Synuclein-pan | 7.55 | 188 | P37840 | 140 | Synuclein family |
| 375 | TGF beta Receptor II | 7.48 | 178 | P37173 | 567 | Protein kinase superfamily, TKL Ser/Thr protein kinase family, TGFB receptor subfamily |
| 376 | TGF beta Receptor III | 7.29 | 156 | Q03167 | 851 | — |
| 377 | TGF beta1 | 7.21 | 148.5 | P01137 | 390 | TGF-beta family |
| 378 | STAT1 | 7.34 | 162 | P42224 | 750 | Transcription factor STAT family |
| 379 | STAT5A | 7.23 | 150.5 | P42229 | 794 | Transcription factor STAT family |
| 380 | FRK | 7.31 | 158.5 | P42685 | 505 | Protein kinase superfamily, Tyr protein kinase family, SRC subfamily |
| 381 | JNKK | 7.29 | 156.5 | P45985 | 399 | Protein kinase superfamily, STE Ser/Thr protein kinase family, MAP kinase kinase subfamily |
| 382 | KPB1/2 | 7.2 | 147 | P46020 | 1223 | Phosphorylase b kinase regulatory chain family |

TABLE 2-continued

| ID | Antibody Name | Normalized data (log2) | Raw data | SwissProt | Length | Protein family |
|---|---|---|---|---|---|---|
| 383 | ATRX | 7.39 | 167.5 | P46100 | 2492 | SNF2/RAD54 helicase family |
| 384 | YAP | 7.29 | 156 | P46937 | 504 | YORKIE family |
| 385 | CKI-alpha | 7.48 | 178.5 | P48729 | 337 | Protein kinase superfamily, CK1 Ser/Thr protein kinase family, Casein kinase I subfamily |
| 386 | CDK8 | 7.53 | 184.5 | P49336 | 464 | Protein kinase superfamily, CMGC Ser/Thr protein kinase family, CDC2/CDKX subfamily |
| 387 | Flt3 ligand | 7.37 | 165 | P49771 | 235 | — |
| 388 | ERF | 7.36 | 164 | P50548 | 548 | ETS family |
| 389 | CD253 | 7.58 | 192 | P50591 | 281 | Tumor necrosis factor family |
| 390 | BRCA2 | 7.44 | 173.5 | P51587 | 3418 | — |
| 391 | MAT1 | 8.94 | 491.5 | P51948 | 309 | — |
| 392 | MAP2K6 | 7.57 | 190 | P52564 | 334 | Protein kinase superfamily, STE Ser/Thr protein kinase family, MAP kinase kinase subfamily |
| 393 | RBM5 | 7.33 | 161 | P52756 | 815 | RBM5/RBM10 family |
| 394 | Hexokinase-3 | 7.4 | 168.5 | P52790 | 923 | Hexokinase family |
| 395 | EFNA3 | 7.32 | 160 | P52797 | 238 | Ephrin family |
| 396 | LIMK1 | 7.26 | 153 | P53667 | 647 | Protein kinase superfamily, TKL Ser/Thr protein kinase family |
| 397 | 5-HT-1A | 7.51 | 182 | P08908 | 422 | G-protein coupled receptor 1 family, 5-hydroxytryptamine receptor subfamily, HTR1A sub-subfamily |
| 398 | 5-HT-1F | 7.22 | 149 | P30939 | 366 | G-protein coupled receptor 1 family |
| 399 | 5-HT-2C | 7.19 | 146 | P28335 | 458 | G-protein coupled receptor 1 family |
| 400 | 5-HT-3A | 7.17 | 144.5 | P46098 | 478 | Ligand-gated ion channel (TC 1.A.9) family, 5-hydroxytryptamine receptor (TC 1.A.9.2) subfamily, HTR3A sub-subfamily |
| 401 | 5-HT-4 | 7.53 | 185 | Q13639 | 388 | G-protein coupled receptor 1 family |
| 402 | 5-HT-5A | 7.39 | 167.5 | P47898 | 357 | G-protein coupled receptor 1 family |
| 403 | ACTN 1/2/3/4 | 7.34 | 161.5 | P12814 | 892 | Alpha-actinin family |
| 404 | ADCY4 | 7.46 | 175.5 | Q8NFM4 | 1077 | Adenylyl cyclase class-4/guanylyl cyclase family |
| 405 | ADCY5/6 | 7.27 | 154.5 | O43306 | 1168 | Adenylyl cyclase class-4/guanylyl cyclase family |
| 406 | ADCY7 | 7.12 | 139.5 | P51828 | 1080 | Adenylyl cyclase class-4/guanylyl cyclase family |
| 407 | ADCY8 | 7.3 | 158 | P40145 | 1251 | Adenylyl cyclase class-4/guanylyl cyclase family |
| 408 | ADD2 | 7.24 | 151.5 | P35612 | 726 | Aldolase class II family, Adducin subfamily |
| 409 | ADD3 | 7.39 | 168 | Q9UEY8 | 706 | Aldolase class II family, Adducin subfamily |
| 410 | AIFM2 | 7.25 | 152 | Q9BRQ8 | 373 | FAD-dependent oxidoreductase family |
| 411 | AVEN | 7.4 | 168.5 | Q9NQS1 | 362 | — |
| 412 | BUB3 | 7.2 | 147 | O43684 | 328 | WD repeat BUB3 family |
| 413 | C56D2 | 7.47 | 177.5 | O14569 | 222 | — |
| 414 | Ik3-2 | 7.17 | 144 | Q9BTV7 | 478 | Cyclin family |
| 415 | CDH10 | 7.53 | 184.5 | Q9Y6N8 | 788 | — |
| 416 | ATP5G3 | 7.43 | 173 | P48201 | 142 | ATPase C chain family |
| 417 | ATP5A1 | 7.34 | 162 | P25705 | 553 | ATPase alpha/beta chains family |
| 418 | ATP5S | 7.61 | 195.5 | Q99766 | 215 | ATP synthase subunit s family |
| 419 | BAGE2 | 7.43 | 172.5 | Q86Y30 | 109 | BAGE family |
| 420 | BAGE3 | 7.19 | 146.5 | Q86Y29 | 109 | BAGE family |
| 421 | BAGE4 | 7.18 | 145.5 | Q86Y28 | 39 | BAGE family |
| 422 | C9orf89 | 7.36 | 164.5 | Q96LW7 | 228 | — |
| 423 | GCNT7 | 7.38 | 167 | Q6ZNI0 | 430 | Glycosyltransferase 14 family |
| 424 | GLB1L3 | 7.51 | 182 | Q8NCI6 | 653 | Glycosyl hydrolase 35 family |
| 425 | SLC27A5 | 7.3 | 158 | Q9Y2P5 | 690 | ATP-dependent AMP-binding enzyme family |
| 426 | BST2 | 7.22 | 149.5 | Q10589 | 180 | Tetherin family |
| 427 | BMP8A | 7.25 | 152.5 | Q7Z5Y6 | 402 | TGF-beta family |
| 428 | ARFGEF2 | 7.44 | 174 | Q9Y6D5 | 1785 | — |
| 429 | CHP2 | 7.16 | 143.5 | O43745 | 196 | Calcineurin regulatory subunit family, CHP subfamily |
| 430 | KCNMB2 | 9.72 | 843 | Q9Y691 | 235 | KCNMB (TC 8.A.14.1) family, KCNMB2 subfamily |
| 431 | CMC1 | 7.68 | 205.5 | O75746 | 678 | Mitochondrial carrier family |
| 432 | CNN2 | 7.22 | 149.5 | Q99439 | 309 | Calponin family |
| 433 | ARPP21 | 7.46 | 175.5 | Q9UBL0 | 812 | — |
| 434 | CAGE1 | 7.27 | 154 | Q8TC20 | 777 | — |
| 435 | NCR1 | 7.53 | 184.5 | O76036 | 304 | Natural cytotoxicity receptor (NCR) family |
| 436 | NCR3 | 7.59 | 193 | O14931 | 201 | Natural cytotoxicity receptor (NCR) family |
| 437 | NEGR1 | 7.22 | 149.5 | Q7Z3B1 | 354 | Immunoglobulin superfamily, IgLON family |
| 438 | C5orf13 | 7.18 | 145.5 | Q16612 | 68 | — |
| 439 | Septin-3 | 7.1 | 137 | Q9UH03 | 358 | Septin family |
| 440 | NSG1 | 7.47 | 177 | P42857 | 185 | NSG family |

TABLE 2-continued

| ID | Antibody Name | Normalized data (log2) | Raw data | SwissProt | Length | Protein family |
|---|---|---|---|---|---|---|
| 441 | NSG2 | 7.22 | 149.5 | Q9Y328 | 171 | NSG family |
| 442 | NPTN | 7.4 | 168.5 | Q9Y639 | 398 | — |
| 443 | NT | 7.18 | 145.5 | Q9P121 | 344 | Immunoglobulin superfamily, IgLON family |
| 444 | NLE1 | 7.28 | 155 | Q9NVX2 | 485 | NLE1/RSA4 family |
| 445 | NFRKB | 7.31 | 158.5 | Q6P4R8 | 1299 | NFRKB family |
| 446 | PPP1R8 | 7.08 | 135 | Q12972 | 351 | — |
| 447 | NCOA7 | 7.18 | 145 | Q8NI08 | 942 | OXR1 family |
| 448 | NRBF2 | 7.23 | 150 | Q96F24 | 287 | — |
| 449 | NFYC | 7.5 | 180.5 | Q13952 | 458 | NFYC/HAP5 subunit family |
| 450 | URB1 | 7.18 | 145.5 | O60287 | 227 | — |
| 451 | PDRG1 | 7.41 | 169.5 | Q9NUG6 | 133 | Prefoldin subunit beta family |
| 452 | PPRC1 | 7.08 | 135.5 | Q5VV67 | 1664 | — |
| 453 | PIGH | 7.11 | 138 | Q14442 | 188 | PIGH family |
| 454 | SLC39A7 | 6.94 | 123 | Q92504 | 469 | ZIP transporter (TC 2.A.5) family, KE4/Catsup subfamily |
| 455 | SLC39A1 | 7.42 | 171 | Q9NY26 | 324 | ZIP transporter (TC 2.A.5) family |
| 456 | ZADH1 | 7.01 | 128.5 | Q8N8N7 | 351 | NADP-dependent oxidoreductase L4BD family |
| 457 | ZADH2 | 7.27 | 154 | Q8N4Q0 | 377 | Zinc-containing alcohol dehydrogenase family, Quinone oxidoreductase subfamily |
| 458 | ZP1 | 7.11 | 138.5 | P60852 | 638 | ZP domain family, ZPB subfamily |
| 459 | CA181 | 7.28 | 155 | Q9NWK9 | 470 | BCD1 family |
| 460 | TTF2 | 7.04 | 131.5 | O00358 | 373 | — |
| 461 | LAMA1 | 7.12 | 139 | P25391 | 3075 | — |
| 462 | 14-3-3 theta | 7.34 | 162 | P27438 | 668 | Parvoviruses non-capsid protein family |
| 463 | INSL4 | 7.18 | 145.5 | Q14641 | 139 | Insulin family |
| 464 | EFEMP1 | 7.16 | 143 | Q12805 | 493 | Fibulin family |
| 465 | EEF1G | 7.1 | 137 | P26641 | 437 | — |
| 466 | TUFM | 7.22 | 149 | P49411 | 452 | GTP-binding elongation factor family, EF-Tu/EF-1A subfamily |
| 467 | ELOVL1 | 7.05 | 132.5 | Q9BW60 | 279 | ELO family |
| 468 | ZP4 | 7.51 | 182 | Q12836 | 540 | ZP domain family, ZPB subfamily |
| 469 | EPN2 | 7.33 | 160.5 | O95208 | 641 | Epsin family |
| 470 | MYC | 7.14 | 141 | P01106 | 439 | — |
| 471 | MET | 7.39 | 167.5 | P08581 | 1390 | Protein kinase superfamily, Tyr protein kinase family |
| 472 | EFNA1 | 7.49 | 180 | P20827 | 205 | Ephrin family |
| 473 | PTK6 (breast tumor kinase) | 7.03 | 130.5 | Q13882 | 451 | Protein kinase superfamily, Tyr protein kinase family, BRK/PTK6/SIK subfamily |
| 474 | LYN | 7.05 | 132.5 | P07948 | 512 | Protein kinase superfamily, Tyr protein kinase family, SRC subfamily |
| 475 | CD34 | 7.1 | 137 | P28906 | 385 | CD34 family |
| 476 | Thioredoxin (TRX) | 7.09 | 136.5 | P10599 | 105 | Thioredoxin family |
| 477 | CD31 | 7.09 | 136.5 | P16284 | 738 | — |
| 478 | TYRO3 | 7.16 | 143.5 | Q06418 | 890 | Protein kinase superfamily, Tyr protein kinase family, AXL/UFO subfamily |
| 479 | RSK1 (p90 RSK) | 7.12 | 139.5 | Q15418 | 735 | Protein kinase superfamily, AGC Ser/Thr protein kinase family, S6 kinase subfamily |
| 480 | MYST1 | 7.15 | 142.5 | Q9H7Z6 | 458 | MYST (SAS/MOZ) family |
| 481 | CIB1 | 7.13 | 140.5 | Q99828 | 191 | — |
| 482 | SORL1 | 7.16 | 143.5 | Q92673 | 2214 | VPS10-related sortilin family, SORL1 subfamily |
| 483 | DDR2 | 7.22 | 149 | Q16832 | 855 | Protein kinase superfamily, Tyr protein kinase family, Insulin receptor subfamily |
| 484 | MER | 7.17 | 144.5 | Q12866 | 999 | Protein kinase superfamily, Tyr protein kinase family, AXL/UFO subfamily |
| 485 | S100B | 7.13 | 140 | P04271 | 92 | S-101 family |
| 486 | AMACR | 7.25 | 152.5 | Q9UHK6 | 382 | CaiB/BaiF CoA-transferase family |
| 487 | MAPK 11 | 7.5 | 180.5 | Q15759 | 364 | Protein kinase superfamily, CMGC Ser/Thr protein kinase family, MAP kinase subfamily |
| 488 | HCK | 7.12 | 139.5 | P08631 | 526 | Protein kinase superfamily, Tyr protein kinase family, SRC subfamily |
| 489 | STYK1 | 7.2 | 147 | Q6J9G0 | 422 | Protein kinase superfamily, Tyr protein kinase family |
| 490 | RET | 7.2 | 147.5 | P07949 | 1114 | Protein kinase superfamily, Tyr protein kinase family |
| 491 | Influenza B virus Nucleoprotein | 7.18 | 145 | P04665 | 560 | Influenza viruses nucleoprotein family |
| 492 | MMP23 (Cleaved-Tyr79) | 9.86 | 928.5 | O75900 | 390 | Peptidase M10A family |
| 493 | MMP27 (Cleaved-Tyr99) | 7.75 | 215 | Q9H306 | 513 | Peptidase M10A family |
| 494 | MMP3 (Cleaved-Phe100) | 7.25 | 152.5 | P08254 | 477 | Peptidase M10A family |
| 495 | PARP (Cleaved-Asp214) | 7.25 | 152 | P09874 | 1014 | — |
| 496 | SUMO2/3 (Cleaved-Gly93) | 7.49 | 179.5 | P61956 | 95 | Ubiquitin family, SUMO subfamily |

TABLE 2-continued

| ID | Antibody Name | Normalized data (log2) | Raw data | SwissProt | Length | Protein family |
|---|---|---|---|---|---|---|
| 497 | ITGA5 (heavy chain, Cleaved-Phe42) | 6.98 | 126 | P08648 | 1049 | Integrin alpha chain family |
| 498 | ITGA5 (light chain, Cleaved-Glu874) | 7.3 | 158 | P08648 | 1049 | Integrin alpha chain family |
| 499 | ITGA6 (light chain, Cleaved-Glu942) | 7.28 | 155.5 | P23229 | 1130 | Integrin alpha chain family |
| 500 | ITGA7 (light chain, Cleaved-Glu959) | 7.27 | 154 | Q13683 | 1181 | Integrin alpha chain family |
| 501 | ITIH1 (Cleaved-Asp672) | 7.04 | 131.5 | P19827 | 911 | ITIH family |
| 502 | p53 | 7.26 | 153.5 | P04637 | — | — |
| 503 | B-RAF | 7.28 | 155 | P15056 | 766 | Protein kinase superfamily, TKL Ser/Thr protein kinase family, RAF subfamily |
| 504 | FER | 7.29 | 157 | P16591 | 822 | Protein kinase superfamily, Tyr protein kinase family, Fes/fps subfamily |
| 505 | MARK3 | 7.25 | 152.5 | P27448 | 753 | Protein kinase superfamily, CAMK Ser/Thr protein kinase family, SNF1 subfamily |
| 506 | Catenin-beta 1 | 7.78 | 220 | P35222 | 781 | Beta-catenin family |
| 507 | ACTN alpha-2/3 | 7.4 | 169 | P35609/Q08043 | — | alpha-actinin family |
| 508 | STAT3 | 7.68 | 205 | P40763 | 770 | Transcription factor STAT family |
| 509 | HNF4alpha/gamma | 7.69 | 207 | P41235/Q14541 | — | nuclear hormone receptor family. NR2 subfamily |
| 510 | CaMK2beta/gamma | 7.34 | 162 | Q13554/Q13555 | — | protein kinase superfamily. CAMK Ser/Thr protein kinase family. CaMK subfamily |
| 511 | E2F6 | 7.58 | 191 | O75461 | 281 | E2F/DP family |
| 512 | Collagen alpha1 XVIII | 7.38 | 166 | P39060 | 1754 | Multiplexin collagen family |
| 513 | EFNA4 | 7.74 | 214.5 | P52798 | 201 | Ephrin family |
| 514 | EFNB3 | 7.85 | 230.5 | Q15768 | 340 | Ephrin family |
| 515 | ERAB | 7.6 | 194 | Q99714 | 261 | Short-chain dehydrogenases/reductases (SDR) family |
| 516 | ERCC1 | 7.41 | 170.5 | P07992 | 297 | ERCC1/RAD10/SWI10 family |
| 517 | p44/42 MAPK | 7.5 | 181.5 | P27361 | 379 | Protein kinase superfamily, CMGC Ser/Thr protein kinase family, MAP kinase subfamily |
| 518 | Ezrin | 7.33 | 161 | P15311 | 586 | — |
| 519 | FAS ligand | 7.34 | 162.5 | P48023 | 281 | Tumor necrosis factor family |
| 520 | FGFR1 Oncogene Partner | 7.19 | 146 | O95684 | 399 | FGFR1OP family |
| 521 | FGFR2 | 7.18 | 145.5 | P21802 | 821 | Protein kinase superfamily, Tyr protein kinase family, Fibroblast growth factor receptor subfamily |
| 522 | FGFR3 | 7.24 | 151.5 | P22607 | 806 | Protein kinase superfamily, Tyr protein kinase family, Fibroblast growth factor receptor subfamily |
| 523 | FHIT | 7.45 | 174.5 | P49789 | 147 | — |
| 524 | Fibrillin-1 | 7.26 | 153 | P35555 | 2871 | Fibrillin family |
| 525 | IKB alpha | 8.33 | 322 | P25963 | 317 | NF-kappa-B inhibitor family |
| 526 | FLI1 | 7.11 | 138.5 | Q01543 | 452 | ETS family |
| 527 | Fra-2 | 7.32 | 160 | P15408 | 326 | BZIP family, Fos subfamily |
| 528 | GABA-B Receptor | 7.13 | 140.5 | Q9UBS5 | 961 | G-protein coupled receptor 3 family, GABA-B receptor subfamily |
| 529 | GAD1 | 7.75 | 215.5 | Q99259 | 594 | Group II decarboxylase family |
| 530 | TGF beta2 | 7.19 | 146 | P61812 | 414 | TGF-beta family |
| 531 | TGF beta3 | 7.2 | 147 | P10600 | 412 | TGF-beta family |
| 532 | TGF alpha | 7.27 | 154 | P01135 | 160 | — |
| 533 | Thrombin Receptor | 11 | 2044 | P25116 | 425 | G-protein coupled receptor 1 family |
| 534 | Thyroid Hormone Receptor alpha | 7.23 | 150.5 | P10827 | 490 | Nuclear hormone receptor family, NR1 subfamily |
| 535 | Thyroid Hormone Receptor beta | 7.26 | 153.5 | P10828 | 461 | Nuclear hormone receptor family, NR1 subfamily |
| 536 | TIMP1 | 7.43 | 172 | P01033 | 207 | Protease inhibitor I35 (TIMP) family |
| 537 | TIMP2 | 7.24 | 151.5 | P16035 | 220 | Protease inhibitor I35 (TIMP) family |
| 538 | TIMP3 | 7.23 | 150 | P35625 | 211 | Protease inhibitor I35 (TIMP) family |
| 539 | Transglutaminase 2 | 7.46 | 175.5 | P21980 | 687 | Transglutaminase superfamily, Transglutaminase family |
| 540 | AOS1 | 7.86 | 233 | Q9UBE0 | 346 | Ubiquitin-activating E1 family |
| 541 | CD40 | 7.58 | 192 | P25942 | 277 | — |
| 542 | CDK7 | 7.5 | 181.5 | P50613 | 346 | Protein kinase superfamily, CMGC Ser/Thr protein kinase family, CDC2/CDKX subfamily |
| 543 | EDD | 7.25 | 152 | O95071 | 2799 | — |
| 544 | FAS | 7.17 | 144 | P25445 | 335 | — |
| 545 | HAT | 7.35 | 163 | O14929 | 419 | HAT1 family |
| 546 | NCoR1 | 7.27 | 154.5 | O75376 | 2440 | N-CoR nuclear receptor corepressors family |
| 547 | NEDD8 | 7.14 | 141.5 | Q15843 | 81 | Ubiquitin family |
| 548 | NYREN18 | 7.17 | 144.5 | Q9Y5A7 | 615 | — |

TABLE 2-continued

| ID | Antibody Name | Normalized data (log2) | Raw data | SwissProt | Length | Protein family |
|---|---|---|---|---|---|---|
| 549 | LIMK2 | 7.04 | 131.5 | P53671 | 638 | Protein kinase superfamily, TKL Ser/Thr protein kinase family |
| 550 | MAPK10 | 7.52 | 183.5 | P53779 | 464 | Protein kinase superfamily, CMGC Ser/Thr protein kinase family, MAP kinase subfamily |
| 551 | TPD52 | 7.17 | 144.5 | P55327 | 224 | TPD52 family |
| 552 | IPKA | 7.41 | 169.5 | P61925 | 76 | PKI family |
| 553 | BLCAP | 7.51 | 182.5 | P62952 | 87 | BLCAP family |
| 554 | CKI-gamma2 | 7.38 | 166 | P78368 | 415 | Protein kinase superfamily, CK1 Ser/Thr protein kinase family, Casein kinase I subfamily |
| 555 | ST5 | 7.25 | 152.5 | P78524 | 1137 | — |
| 556 | CDKL1 | 7.2 | 147.5 | Q00532 | 357 | Protein kinase superfamily, CMGC Ser/Thr protein kinase family, CDC2/CDKX subfamily |
| 557 | MEF2B | 7.69 | 207 | Q02080 | 365 | MEF2 family |
| 558 | SP3/4 | 7.71 | 210 | Q02447 | 781 | Sp1 C2H2-type zinc-finger protein family |
| 559 | HEN1/2 | 7.68 | 204.5 | Q02575 | 133 | — |
| 560 | Octamer-binding transcription factor 6 | 7.49 | 179.5 | Q03052 | 451 | POU transcription factor family, Class-3 subfamily |
| 561 | CREM | 7.78 | 219.5 | Q03060 | 361 | BZIP family |
| 562 | Mevalonate Kinase | 7.31 | 158.5 | Q03426 | 396 | GHMP kinase family, Mevalonate kinase subfamily |
| 563 | ERCC6 | 7.72 | 211 | Q03468 | 1493 | SNF2/RAD54 helicase family |
| 564 | HSF2 | 7.58 | 191 | Q03933 | 536 | HSF family |
| 565 | TLE2 | 7.36 | 164.5 | Q04725 | 743 | WD repeat Groucho/TLE family |
| 566 | TLE4 | 7.44 | 174 | Q04727 | 773 | WD repeat Groucho/TLE family |
| 567 | SRY | 7.76 | 217.5 | Q05066 | 204 | SRY family |
| 568 | CDH11 | 7.08 | 135.5 | P55287 | 796 | — |
| 569 | CDH18 | 7.21 | 148.5 | Q13634 | 790 | — |
| 570 | CDH20 | 7.34 | 162 | Q9HBT6 | 801 | — |
| 571 | CDH24 | 9.13 | 559.5 | Q86UP0 | 819 | — |
| 572 | CDH2 | 7.24 | 151.5 | P19022 | 906 | — |
| 573 | CDH3 | 7.85 | 231.5 | P22223 | 829 | — |
| 574 | CDH4 | 7.5 | 181 | P55283 | 916 | — |
| 575 | CDH8 | 7.5 | 181 | P55286 | 799 | — |
| 576 | CDH9 | 9.06 | 534 | Q9ULB4 | 789 | — |
| 577 | CD2 Tail-binding | 7.3 | 157.5 | O95400 | 341 | — |
| 578 | CD302 | 7.36 | 164.5 | Q8IX05 | 232 | — |
| 579 | APC6 | 7.78 | 220 | Q13042 | 620 | APC6/CDC16 family |
| 580 | p55CDC | 7.25 | 152.5 | Q12834 | 499 | WD repeat CDC20/Fizzy family |
| 581 | p50 CDC37 | 7.09 | 136.5 | Q16543 | 378 | CDC37 family |
| 582 | CDC6 | 7.64 | 199.5 | Q99741 | 560 | CDC6/cdc18 family |
| 583 | CDCA2 | 7.22 | 149.5 | Q69YH5 | 1023 | — |
| 584 | CDCA3 | 7.33 | 161 | Q99618 | 268 | — |
| 585 | CDCA4 | 7.6 | 194 | Q9BXL8 | 241 | — |
| 586 | CDCA7 | 7.29 | 156.5 | Q9BWT1 | 371 | — |
| 587 | CLIP1 | 7.09 | 136 | P30622 | 1438 | — |
| 588 | CHST10 | 7.11 | 138.5 | O43529 | 356 | Sulfotransferase 2 family |
| 589 | CHST2 | 7.38 | 166.5 | Q9Y4C5 | 530 | Sulfotransferase 1 family, Gal/GlcNAc/GalNAc subfamily |
| 590 | CHST6 | 7.28 | 155.5 | Q9GZX3 | 395 | Sulfotransferase 1 family, Gal/GlcNAc/GalNAc subfamily |
| 591 | CHST8 | 7.23 | 150 | Q9H2A9 | 424 | Sulfotransferase 2 family |
| 592 | CA13 | 7.29 | 156.5 | Q8N1Q1 | 262 | Alpha-carbonic anhydrase family |
| 593 | CA14 | 7.21 | 148 | Q9ULX7 | 337 | Alpha-carbonic anhydrase family |
| 594 | CA5B | 7.51 | 182 | Q9Y2D0 | 317 | Alpha-carbonic anhydrase family |
| 595 | CA6 | 7.19 | 146.5 | P23280 | 308 | Alpha-carbonic anhydrase family |
| 596 | CBR3 | 7.17 | 144 | O75828 | 277 | Short-chain dehydrogenases/reductases (SDR) family |
| 597 | CPB2 | 7.33 | 160.5 | Q96IY4 | 423 | Peptidase M14 family |
| 598 | CPM | 7.26 | 153.5 | P14384 | 443 | Peptidase M14 family |
| 599 | CPN1 | 7.11 | 138 | P15169 | 458 | Peptidase M14 family |
| 600 | CNTROB | 7.48 | 179 | Q8N137 | 903 | — |
| 601 | CBLN1 | 7.37 | 165.5 | P23435 | 193 | — |
| 602 | CBLN2 | 7.22 | 149 | Q8IUK8 | 224 | — |
| 603 | CBLN3 | 7.33 | 161 | Q6UW01 | 205 | — |
| 604 | CBLN4 | 7.22 | 149 | Q9NTU7 | 201 | — |
| 605 | CLN6 | 7.15 | 142 | Q9NWW5 | 311 | — |
| 606 | PIGY | 7.08 | 135.5 | Q3MUY2 | 71 | — |
| 607 | PIP5K1C | 7.58 | 191 | O60331 | 668 | — |
| 608 | PIK3R5 | 7.02 | 129.5 | Q8WYR1 | 880 | — |
| 609 | PLA1A | 7.09 | 136 | Q53H76 | 456 | AB hydrolase superfamily, Lipase family |
| 610 | PLD4 | 7.77 | 219 | Q96BZ4 | 506 | Phospholipase D family |
| 611 | Serpin A5 | 7.13 | 140.5 | P05154 | 406 | Serpin family |
| 612 | POLDIP3 | 7.33 | 161 | Q9BY77 | 421 | — |

TABLE 2-continued

| ID | Antibody Name | Normalized data (log2) | Raw data | SwissProt | Length | Protein family |
|---|---|---|---|---|---|---|
| 613 | KCNK15 | 7.13 | 140.5 | Q9H427 | 330 | Two pore domain potassium channel (TC 1.A.1.8) family |
| 614 | KCNK17 | 7.37 | 165 | Q96T54 | 332 | Two pore domain potassium channel (TC 1.A.1.8) family |
| 615 | KCNK4 | 7.13 | 140 | Q9NYG8 | 393 | Two pore domain potassium channel (TC 1.A.1.8) family |
| 616 | KCNT1 | 7.29 | 157 | Q5JUK3 | 1230 | Potassium channel family, Calcium-activated (TC 1.A.1.3) subfamily, KCa4.1/KCNT1 sub-subfamily |
| 617 | KCNA1 | 7.48 | 178.5 | Q09470 | 495 | Potassium channel family, A (Shaker) (TC 1.A.1.2) subfamily, Kv1.1/KCNA1 sub-subfamily |
| 618 | KCND1 | 7.13 | 140 | Q9NSA2 | 647 | Potassium channel family, D (Shal) (TC 1.A.1.2) subfamily, Kv4.1/KCND1 sub-subfamily |
| 619 | KCNG3 | 7.54 | 186.5 | Q8TAE7 | 436 | Potassium channel family, G (TC 1.A.1.2) subfamily, Kv6.3/KCNG3 sub-subfamily |
| 620 | KCNV2 | 7.46 | 176.5 | Q8TDN2 | 545 | Potassium channel family, V (TC 1.A.1.2) subfamily, Kv8.2/KCNV2 sub-subfamily |
| 621 | CDC40 | 7.1 | 137 | O60508 | 579 | — |
| 622 | SLU7 | 7.13 | 140 | O95391 | 586 | SLU7 family |
| 623 | A26C2/3 | 7.13 | 140.5 | Q6S5H5 | 508 | POTE family |
| 624 | POTE8 | 7.23 | 150.5 | Q6S8J7 | 498 | POTE family |
| 625 | GRK6 | 7.22 | 149 | P43250 | 576 | Protein kinase superfamily, AGC Ser/Thr protein kinase family, GPRK subfamily |
| 626 | CLK1 | 7.3 | 157.5 | P49759 | 484 | Protein kinase superfamily, CMGC Ser/Thr protein kinase family, Lammer subfamily |
| 627 | CLK2 | 6.99 | 127.5 | P49760 | 499 | Protein kinase superfamily, CMGC Ser/Thr protein kinase family, Lammer subfamily |
| 628 | p57KIP2 | 7.43 | 173 | P49918 | 316 | CDI family |
| 629 | EFNA5 | 7.04 | 132 | P52803 | 228 | Ephrin family |
| 630 | EPHB4 | 7.2 | 147 | P54760 | 987 | Protein kinase superfamily, Tyr protein kinase family, Ephrin receptor subfamily |
| 631 | p19 INK4d | 7.21 | 148 | P55273 | 166 | CDKN2 cyclin-dependent kinase inhibitor family |
| 632 | S6K-alpha2 | 7.35 | 163.5 | Q15349 | 733 | Protein kinase superfamily, AGC Ser/Thr protein kinase family, S6 kinase subfamily |
| 633 | p97 MAPK | 7.35 | 163 | Q16659 | 721 | Protein kinase superfamily, CMGC Ser/Thr protein kinase family, MAP kinase subfamily |
| 634 | MARK4 | 7.43 | 172.5 | Q96L34 | 752 | Protein kinase superfamily, CAMK Ser/Thr protein kinase family, SNF1 subfamily |
| 635 | EPHA6 | 7.54 | 186 | Q9UF33 | 1035 | Protein kinase superfamily, Tyr protein kinase family, Ephrin receptor subfamily |
| 636 | 14-3-3 beta | 7.51 | 182.5 | P31946 | 246 | 14-3-3 family |
| 637 | 14-3-3 epsilon | 7.16 | 143.5 | P62258 | 255 | 14-3-3 family |
| 638 | Cytochrome b561 D1 | 11.5 | 2889 | Q8N8Q1 | 229 | — |
| 639 | Cytochrome c-type Heme Lyase | 7.41 | 169.5 | P53701 | 268 | Cytochrome c-type heme lyase family |
| 640 | Cofilin | 7.32 | 160 | Q9Y281 | 166 | Actin-binding proteins ADF family |
| 641 | Cytochrome P450 1A1/2 | 7.49 | 179.5 | P04798 | 512 | Cytochrome P450 family |
| 642 | Cytochrome P450 24A1 | 7.41 | 169.5 | Q07973 | 514 | Cytochrome P450 family |
| 643 | Cytochrome P450 27A1 | 7.3 | 157.5 | Q02318 | 531 | Cytochrome P450 family |
| 644 | IKBKE (IKK epsilon) | 7.09 | 136 | Q14164 | 716 | Protein kinase superfamily, Ser/Thr protein kinase family, I-kappa-B kinase subfamily |
| 645 | MLL | 7.08 | 135.5 | Q03164 | 3969 | Histone-lysine methyltransferase family, TRX/MLL subfamily |
| 646 | Calreticulin | 7.07 | 134.5 | P27797 | 417 | Calreticulin family |
| 647 | YES1 | 7.04 | 132 | P07947 | 543 | Protein kinase superfamily, Tyr protein kinase family, SRC subfamily |
| 648 | GATA3 | 7.14 | 141 | P23771 | 443 | — |
| 649 | Calnexin | 7.19 | 146 | P27824 | 592 | Calreticulin family |
| 650 | cAMP | 7.22 | 149.5 | N/A | — | — |
| 651 | Glucose-6-phosphate isomerase | 7.13 | 140.5 | P06744 | 558 | GPI family |
| 652 | SRC | 7.08 | 135.5 | P12931 | 536 | Protein kinase superfamily, Tyr protein kinase family, SRC subfamily |
| 653 | IGFBP2 | 7.14 | 141 | P18065 | 325 | — |
| 654 | PYK2 (FAK2) | 7.16 | 143.5 | Q14289 | 1009 | Protein kinase superfamily, Tyr protein kinase family, FAK subfamily |
| 655 | PAR4 | 7.06 | 133.5 | Q96IZ0 | 340 | — |
| 656 | ITK (LYK) | 7.15 | 142.5 | Q08881 | 620 | Protein kinase superfamily, Tyr protein kinase family, TEC subfamily |
| 657 | ALCAM | 7.14 | 141.5 | Q13740 | 583 | — |
| 658 | TNK1 | 7.21 | 148 | Q13470 | 666 | Protein kinase superfamily, Tyr protein kinase family |

TABLE 2-continued

| ID | Antibody Name | Normalized data (log2) | Raw data | SwissProt | Length | Protein family |
|---|---|---|---|---|---|---|
| 659 | CHK2 | 7.18 | 145 | O96017 | 543 | Protein kinase superfamily, CAMK Ser/Thr protein kinase family, CHK2 subfamily |
| 660 | SND1/P100 | 7.43 | 173 | Q7KZF4 | 910 | — |
| 661 | MAP4K4 | 7.34 | 161.5 | O95819 | 1239 | — |
| 662 | PARL | 7.13 | 140 | Q9H300 | 379 | Peptidase S54 family |
| 663 | CRYAB | 7.01 | 129 | P02511 | 175 | Small heat shock protein (HSP20) family |
| 664 | E2F2 | 7.08 | 135 | Q14209 | 437 | E2F/DP family |
| 665 | TAF1A | 7.18 | 145.5 | Q15573 | 450 | — |
| 666 | Smad1/5/9 | 7.1 | 137 | Q15797 Q99717 Q15198 | — | dwarfin/SMAD family |
| 667 | MAP3KL4 | 7.58 | 191.5 | Q5TCX8 | 1036 | Protein kinase superfamily, STE Ser/Thr protein kinase family, MAP kinase kinase kinase subfamily |
| 668 | CaMK1-beta | 7.42 | 171 | Q6P2M8 | 343 | Protein kinase superfamily, CAMK Ser/Thr protein kinase family, CaMK subfamily |
| 669 | STRAD | 7.39 | 167.5 | Q7RTN6 | 431 | Protein kinase superfamily, STE Ser/Thr protein kinase family, STE20 subfamily |
| 670 | SIAH1 | 7.28 | 155.5 | Q8IUQ4 | 282 | SINA (Seven in absentia) family |
| 671 | IP6K3 | 7.4 | 169 | Q96PC2 | 410 | Inositol phosphokinase (IPK) family |
| 672 | RBAK | 7.37 | 165 | Q9NYW8 | 714 | Krueppel C2H2-type zinc-finger protein family |
| 673 | PIP5K | 7.28 | 155 | Q9Y2I7 | 2098 | — |
| 674 | FGF22 | 8.39 | 336.5 | Q9HCT0 | 170 | Heparin-binding growth factors family |
| 675 | HER2 | 7.29 | 157 | P04626 | 1255 | Protein kinase superfamily, Tyr protein kinase family, EGF receptor subfamily |
| 676 | ARF4 | 7.32 | 159.5 | P18085 | 180 | Small GTPase superfamily, Arf family |
| 677 | ATPAF2 | 7.29 | 156 | Q8N5M1 | 289 | ATP12 family |
| 678 | ADA2L | 7.26 | 153 | O75478 | 443 | — |
| 679 | ACTL6A | 7.33 | 161 | O96019 | 429 | Actin family |
| 680 | ACVL1 | 7.06 | 133 | P37023 | 503 | Protein kinase superfamily, TKL Ser/Thr protein kinase family, TGFB receptor subfamily |
| 681 | ADK | 7.68 | 205.5 | P55263 | 362 | Carbohydrate kinase PfkB family |
| 682 | GFR alpha-1 | 7.32 | 159.5 | P56159 | 465 | GDNFR family |
| 683 | GAD1/2 | 7.93 | 244.5 | Q99259 | 594 | Group II decarboxylase family |
| 684 | GADD153 | 7.23 | 150.5 | P35638 | 169 | BZIP family |
| 685 | Galectin 3 | 7.19 | 146.5 | P17931 | 250 | — |
| 686 | GANP | 7.16 | 143 | O60318 | 1980 | SAC3 family |
| 687 | Gastrin | 7.13 | 140.5 | P01350 | 101 | Gastrin/cholecystokinin family |
| 688 | Glucagon | 7.19 | 146 | P01275 | 180 | Glucagon family |
| 689 | mGluR2/3 | 8.71 | 417.5 | Q14416 | 872 | G-protein coupled receptor 3 family |
| 690 | mGluR4 | 7.39 | 168 | Q14833 | 912 | G-protein coupled receptor 3 family |
| 691 | GluR5 | 7.24 | 151 | P39086 | 918 | Glutamate-gated ion channel (TC 1.A.10.1) family, GRIK1 subfamily |
| 692 | mGluR6 | 7.17 | 144.5 | O15303 | 877 | G-protein coupled receptor 3 family |
| 693 | mGluR7 | 7.43 | 173 | Q14831 | 915 | G-protein coupled receptor 3 family |
| 694 | mGluR8 | 7.42 | 171 | O00222 | 908 | G-protein coupled receptor 3 family |
| 695 | GLUT1 | 7.7 | 208 | P11166 | 492 | Major facilitator superfamily, Sugar transporter (TC 2.A.1.1) family, Glucose transporter subfamily |
| 696 | GLUT3 | 7.23 | 150 | P11169 | 496 | Major facilitator superfamily, Sugar transporter (TC 2.A.1.1) family, Glucose transporter subfamily |
| 697 | Granzyme B | 7.15 | 142.5 | P10144 | 247 | Peptidase S1 family, Granzyme subfamily |
| 698 | GRP75 | 7.17 | 144.5 | P38646 | 679 | Heat shock protein 70 family |
| 699 | GRP78 | 7.59 | 193 | P11021 | 654 | Heat shock protein 70 family |
| 700 | GRP94 | 7.12 | 139 | P14625 | 803 | Heat shock protein 90 family |
| 701 | PIAS1 | 7.46 | 176.5 | O75925 | 651 | PIAS family |
| 702 | PIAS2 | 7.06 | 133.5 | O75928 | 621 | PIAS family |
| 703 | PIAS3 | 7.06 | 133.5 | Q9Y6X2 | 628 | PIAS family |
| 704 | PIAS4 | 7.34 | 162.5 | Q8N2W9 | 510 | PIAS family |
| 705 | SENP1 | 7.39 | 168 | Q9P0U3 | 644 | Peptidase C48 family |
| 706 | SENP2 | 7.32 | 159.5 | Q9HC62 | 589 | Peptidase C48 family |
| 707 | SENP3 | 7.07 | 134.5 | Q9H4L4 | 574 | Peptidase C48 family |
| 708 | SENP5 | 7.16 | 143 | Q96HI0 | 755 | Peptidase C48 family |
| 709 | SENP6 | 7.13 | 140.5 | Q9GZR1 | 1112 | Peptidase C48 family |
| 710 | SENP7 | 7.24 | 151.5 | Q9BQF6 | 1050 | Peptidase C48 family |
| 711 | SENP8 | 7.27 | 154 | Q96LD8 | 212 | Peptidase C48 family |
| 712 | Sumo1 | 7.25 | 152 | P63165 | 101 | Ubiquitin family, SUMO subfamily |
| 713 | TIMP4 | 7.11 | 138.5 | Q99727 | 224 | Protease inhibitor I35 (TIMP) family |
| 714 | TNF Receptor I | 7.22 | 149.5 | P19438 | 455 | — |
| 715 | TOP2B | 7.23 | 150.5 | Q02880 | 1626 | Type II topoisomerase family |
| 716 | TRADD | 7.26 | 153.5 | Q15628 | 312 | — |
| 717 | TRXR2 | 7.34 | 162.5 | Q9NNW7 | 524 | Class-I pyridine nucleotide-disulfide oxidoreductase family |

TABLE 2-continued

| ID | Antibody Name | Normalized data (log2) | Raw data | SwissProt | Length | Protein family |
|---|---|---|---|---|---|---|
| 718 | Tubulin alpha | 9.36 | 655.5 | Q71U36 | 451 | Tubulin family |
| 719 | Tubulin beta | 7.29 | 156.5 | Q13509 | 450 | Tubulin family |
| 720 | MEF2C | 7.07 | 134 | Q06413 | 473 | MEF2 family |
| 721 | SMF | 7.31 | 159 | Q12766 | 1538 | — |
| 722 | CDK5R2 | 7.42 | 171.5 | Q13319 | 367 | Cyclin-dependent kinase 5 activator family |
| 723 | MTA1 | 9.54 | 744 | Q13330 | 715 | — |
| 724 | TUSC3 | 7.19 | 146 | Q13454 | 348 | OST3/O5T6 family |
| 725 | Smad4 | 7.13 | 140 | Q13485 | 552 | Dwarfin/SMAD family |
| 726 | SERC3 | 7.16 | 143.5 | Q13530 | 473 | TDE1 family |
| 727 | GAS6 | 7.22 | 149 | Q14393 | 721 | — |
| 728 | CHD4 | 7.24 | 151 | Q14839 | 1912 | SNF2/RAD54 helicase family |
| 729 | CDK5R1 | 7.16 | 143 | Q15078 | 307 | Cyclin-dependent kinase 5 activator family |
| 730 | IRF4 | 7.23 | 150 | Q15306 | 451 | IRF family |
| 731 | EPHA7 | 7.35 | 163.5 | Q15375 | 998 | Protein kinase superfamily, Tyr protein kinase family, Ephrin receptor subfamily |
| 732 | TAF5 | 7.38 | 167 | Q15542 | 800 | WD repeat TAF5 family |
| 733 | RhoH | 7.47 | 177.5 | Q15669 | 191 | Small GTPase superfamily, Rho family |
| 734 | SPR1 | 7.3 | 158 | Q15743 | 365 | G-protein coupled receptor 1 family |
| 735 | CEBPE | 8.29 | 313.5 | Q15744 | 281 | BZIP family, C/EBP subfamily |
| 736 | MAPK3 | 7.4 | 169 | Q16644 | 382 | Protein kinase superfamily, CAMK Ser/Thr protein kinase family |
| 737 | DGKD | 7.15 | 142 | Q16760 | 1214 | Eukaryotic diacylglycerol kinase family |
| 738 | DOK7 | 7.31 | 158.5 | Q18PE1 | 504 | — |
| 739 | CMKLR1 | 7.39 | 168 | Q99788 | 373 | G-protein coupled receptor 1 family |
| 740 | CNTD2 | 8.08 | 271.5 | Q9H8S5 | 307 | — |
| 741 | Collagen I alpha2 | 7.16 | 143.5 | P08123 | 1366 | Fibrillar collagen family |
| 742 | Collagen IV alpha2 | 7.25 | 152 | P08572 | 1712 | Type IV collagen family |
| 743 | Collagen IV alpha3 | 7.28 | 155 | Q01955 | 1670 | Type IV collagen family |
| 744 | Collagen IV alpha4 | 7.2 | 147.5 | P53420 | 1690 | Type IV collagen family |
| 745 | Collagen IV alpha5 | 7.24 | 151.5 | P29400 | 1685 | Type IV collagen family |
| 746 | Collagen IV alpha6 | 7.54 | 186 | Q14031 | 1691 | Type IV collagen family |
| 747 | Collagen V alpha1 | 7.44 | 174 | P20908 | 1838 | Fibrillar collagen family |
| 748 | Collagen V alpha2 | 7.22 | 149.5 | P05997 | 1499 | Fibrillar collagen family |
| 749 | Collagen VI alpha3 | 7.19 | 146.5 | P12111 | 3177 | Type VI collagen family |
| 750 | Collagen IX alpha3 | 7.33 | 161 | Q14050 | 684 | Fibril-associated collagens with interrupted helices (FACIT) family |
| 751 | Collagen XI alpha1 | 7.32 | 159.5 | P12107 | 1806 | Fibrillar collagen family |
| 752 | Collagen XII alpha1 | 7.15 | 142.5 | Q99715 | 3063 | Fibril-associated collagens with interrupted helices (FACIT) family |
| 753 | Collagen XIV alpha1 | 7.39 | 168 | Q05707 | 1796 | Fibril-associated collagens with interrupted helices (FACIT) family |
| 754 | Collagen XVIII alpha1 | 7.13 | 140.5 | P39060 | 1754 | Multiplexin collagen family |
| 755 | Collagen XIX alpha1 | 7.36 | 164.5 | Q14993 | 1142 | Fibril-associated collagens with interrupted helices (FACIT) family |
| 756 | Collagen XX alpha1 | 7.14 | 141 | Q9P218 | 1284 | — |
| 757 | Collagen XXIII alpha1 | 7.39 | 168 | Q86Y22 | 540 | — |
| 758 | CLCC1 | 6.98 | 126 | Q96S66 | 551 | Chloride channel MCLC family |
| 759 | CLIC3 | 7.01 | 129 | O95833 | 236 | Chloride channel CLIC family |
| 760 | CLIC4 | 7.24 | 151 | Q9Y696 | 253 | Chloride channel CLIC family |
| 761 | CDYL2 | 7.41 | 170.5 | Q8N8U2 | 506 | — |
| 762 | KIF4A | 7.47 | 177.5 | O95239 | 1232 | Kinesin-like protein family, Chromokinesin subfamily |
| 763 | CKLF2 | 7.44 | 174 | Q8TAZ6 | 248 | Chemokine-like factor family |
| 764 | CLDN19 | 7.27 | 154 | Q8N6F1 | 224 | Claudin family |
| 765 | CLDN6 | 7.43 | 172 | P56747 | 220 | Claudin family |
| 766 | CSTF2T | 7.25 | 152.5 | Q9H0L4 | 616 | — |
| 767 | CLASP1 | 7.25 | 152 | Q7Z460 | 1538 | CLASP family |
| 768 | ST6GAL1 | 7.25 | 152 | P15907 | 406 | Glycosyltransferase 29 family |
| 769 | RCL | 7.26 | 153.5 | O43598 | 174 | Deoxyribonucleoside 5'-monophosphate N-glycosidase family |
| 770 | COPZ1 | 7.59 | 192.5 | P61923 | 177 | Adaptor complexes small subunit family |
| 771 | C1S | 7.11 | 138.5 | P09871 | 688 | Peptidase S1 family |
| 772 | CD55 | 7.13 | 140.5 | P08174 | 381 | Receptors of complement activation (RCA) family |
| 773 | CNTN4 | 7.09 | 136.5 | Q8IWV2 | 1026 | Immunoglobulin superfamily, Contactin family |
| 774 | CPNE8 | 7.43 | 173 | Q86YQ8 | 564 | Copine family |
| 775 | CXADR | 7.32 | 160 | P78310 | 365 | — |
| 776 | CNGA2 | 7.28 | 155.5 | Q16280 | 664 | Cyclic nucleotide-gated cation channel (TC 1.A.1.5) family, CNGA2 subfamily |
| 777 | ENAH | 7.57 | 190 | Q8N857 | 591 | Ena/VASP family |
| 778 | PMS2/PMS2CL | 7.66 | 202.5 | Q68D20 | 193 | DNA mismatch repair MutL/HexB family |
| 779 | RED | 7.14 | 141 | Q13123 | 557 | RED family |
| 780 | S100A16 | 7.14 | 141.5 | Q96FQ6 | 103 | S-100 family |
| 781 | S100A3 | 7.26 | 153.5 | P33764 | 101 | S-100 family |
| 782 | S100Z | 7.24 | 151 | Q8WXG8 | 99 | S-100 family |

TABLE 2-continued

| ID | Antibody Name | Normalized data (log2) | Raw data | SwissProt | Length | Protein family |
|---|---|---|---|---|---|---|
| 783 | PC | 7.11 | 138 | P11498 | 1178 | — |
| 784 | PDK2 | 7.46 | 175.5 | Q15119 | 407 | PDK/BCKDK protein kinase family |
| 785 | RABEP1 | 7.2 | 147.5 | Q15276 | 862 | Rabaptin family |
| 786 | RABEP2 | 7.28 | 155.5 | Q9H5N1 | 569 | Rabaptin family |
| 787 | CHML | 7.25 | 152.5 | P26374 | 656 | Rab GDI family |
| 788 | RAB11FIP2 | 7.17 | 144.5 | Q7L804 | 512 | — |
| 789 | RAB11FIP3 | 7.16 | 143 | O75154 | 756 | — |
| 790 | RAB11FIP4 | 7.51 | 182.5 | Q86Y53 | 637 | — |
| 791 | RAB3GAP1 | 7.28 | 155 | Q15042 | 981 | Rab3-GAP catalytic subunit family |
| 792 | RAB3GAP2 | 7.06 | 133.5 | Q9H2M9 | 1393 | Rab3-GAP regulatory subunit family |
| 793 | RDX | 7.16 | 143 | P35241 | 583 | — |
| 794 | RASSF2 | 7.83 | 227 | P50749 | 326 | — |
| 795 | RASSF4 | 7.11 | 138 | Q9H2L5 | 321 | — |
| 796 | Cytochrome P450 2C8/9/18/19 | 7.35 | 163 | P33260 | 490 | Cytochrome P450 family |
| 797 | Cytochrome P450 2C19 | 7.63 | 197.5 | P33261 | 490 | Cytochrome P450 family |
| 798 | Cytochrome P450 2E1 | 6.95 | 123.5 | P05181 | 493 | Cytochrome P450 family |
| 799 | Cytochrome P450 2R1 | 7.24 | 151 | Q6VVX0 | 501 | Cytochrome P450 family |
| 800 | Cytochrome P450 2S1 | 7.5 | 181 | Q96SQ9 | 504 | Cytochrome P450 family |
| 801 | Cytochrome P450 4Z1 | 7.48 | 178 | Q86W10 | 505 | Cytochrome P450 family |
| 802 | Cytochrome P450 7B1 | 7 | 128 | O75881 | 506 | Cytochrome P450 family |
| 803 | MLH1 | 7.46 | 176 | P40692 | 756 | DNA mismatch repair MutL/HexB family |
| 804 | C9 | 7.92 | 242.5 | P02748 | 559 | Complement C6/C7/C8/C9 family |
| 805 | GRB2 | 7.57 | 190 | P62993 | 217 | GRB2/sem-5/DRK family |
| 806 | WEE2 | 7.58 | 191 | P0C1S8 | 567 | Protein kinase superfamily, Ser/Thr protein kinase family, WEE1 subfamily |
| 807 | SIAH2 | 7.3 | 158 | O43255 | 324 | SINA (Seven in absentia) family |
| 808 | Cytochrome P450 3A7 | 7.05 | 132.5 | A4D288 | 503 | — |
| 809 | Cytochrome P450 2D6 | 7.28 | 155.5 | Q2XND8/P1063 | — | Cytochrome P450 family |
| 810 | Histone H1 (Acetyl-Lys25) | 7.47 | 177 | Q8IZA3 | 346 | Histone H1/H5 family |
| 811 | Histone H2A(Acetyl-Lys5) | 7.6 | 194.5 | P0C0S5 | 128 | Histone H2A family |
| 812 | Histone H2B(Acetyl-Lys5) | 7.45 | 175 | P57053 | 126 | Histone H2B family |
| 813 | Histone H2B (Acetyl-Lys12) | 7.35 | 163.5 | P57053 | 126 | Histone H2B family |
| 814 | Histone H2B (Acetyl-Lys15) | 7.25 | 152 | P57053 | 126 | Histone H2B family |
| 815 | DDR1 | 7.03 | 131 | Q08345 | 913 | Protein kinase superfamily, Tyr protein kinase family, Insulin receptor subfamily |
| 816 | MDM4 | 6.98 | 126 | O15151 | 490 | MDM2/MDM4 family |
| 817 | AXL | 6.98 | 126 | P30530 | 894 | Protein kinase superfamily, Tyr protein kinase family, AXL/UFO subfamily |
| 818 | RON | 7.02 | 130 | Q04912 | 1400 | Protein kinase superfamily, Tyr protein kinase family |
| 819 | PAR1 | 7.08 | 135 | P25116 | 425 | G-protein coupled receptor 1 family |
| 820 | CD33 | 7.07 | 134 | P20138 | 364 | Immunoglobulin superfamily, SIGLEC (sialic acid binding Ig-like lectin) family |
| 821 | SOX2 | 7.07 | 134.5 | P48431 | 317 | — |
| 822 | human Albumin | 7.08 | 135 | P02768 | 609 | ALB/AFP/VDB family |
| 823 | NCOA3 | 7.11 | 138.5 | Q9Y6Q9 | 1424 | SRC/p160 nuclear receptor coactivator family |
| 824 | Keratin 1 (CK1) | 7.11 | 138.5 | P04264 | 644 | Intermediate filament family |
| 825 | CER1 | 7.13 | 140 | O95813 | 267 | DAN family |
| 826 | CD44 | 7.13 | 140 | P16070 | 742 | — |
| 827 | CDKN1B | 7.12 | 139 | Q6I9V6 | 198 | — |
| 828 | LPA | 7.11 | 138.5 | P08519 | 4548 | Peptidase S1 family, Plasminogen subfamily |
| 829 | CD45 | 7.14 | 141.5 | P08575 | 1304 | Protein-tyrosine phosphatase family, Receptor class 1/6 subfamily |
| 830 | Myeloperoxidase | 7.3 | 157.5 | P05164 | 745 | Peroxidase family, XPO subfamily |
| 831 | Myostatin | 7.18 | 145.5 | O14793 | 375 | TGF-beta family |
| 832 | IL-2 | 7.16 | 143.5 | P60568 | 153 | IL-2 family |
| 833 | R-spondin 1 | 7.09 | 136.5 | Q2MKA7 | 263 | R-spondin family |
| 834 | ADAR1 | 7.24 | 151 | P55265 | 1226 | — |
| 835 | ADCK2 | 7.1 | 137.5 | Q7Z695 | 626 | Protein kinase superfamily, ADCK protein kinase family |
| 836 | ADCK1 | 7.06 | 133 | Q86TW2 | 530 | Protein kinase superfamily |
| 837 | ACTR-1C | 7.51 | 182.5 | Q8NER5 | 493 | Protein kinase superfamily, TKL Ser/Thr protein kinase family, TGFB receptor subfamily |
| 838 | ADCK3 | 7.07 | 134 | Q8NI60 | 647 | Protein kinase superfamily, ADCK protein kinase family |
| 839 | ADPGK | 7.39 | 167.5 | Q9BRR6 | 497 | ADP-dependent glucokinase family |
| 840 | ADNP | 7.54 | 185.5 | Q9H2P0 | 1102 | — |
| 841 | AATF | 7.5 | 181.5 | Q9NY61 | 560 | AATF family |

TABLE 2-continued

| ID | Antibody Name | Normalized data (log2) | Raw data | SwissProt | Length | Protein family |
|---|---|---|---|---|---|---|
| 842 | ADRB1 | 7.24 | 151 | P08588 | 477 | G-protein coupled receptor 1 family, Adrenergic receptor subfamily, ADRB1 sub-subfamily |
| 843 | ACAD10 | 714 | 141.5 | Q6JQN1 | 1059 | Acyl-CoA dehydrogenase family |
| 844 | ACBD6 | 7.48 | 178.5 | Q9BR61 | 282 | — |
| 845 | ACOT2 | 6.88 | 117.5 | P49753 | 483 | C/M/P thioester hydrolase family |
| 846 | ACOT4 | 7.06 | 133 | Q8N9L9 | 421 | C/M/P thioester hydrolase family |
| 847 | AARSD1 | 7.38 | 166 | Q9BTE6 | 412 | Class-II aminoacyl-tRNA synthetase family, Alax-L subfamily |
| 848 | ABCA8 | 7.16 | 143 | O94911 | 1581 | ABC transporter superfamily, ABCA family |
| 849 | ABCB7 | 7.26 | 153.5 | O75027 | 752 | ABC transporter superfamily, ABCB family, Heavy Metal importer (TC 3.A.1.210) subfamily |
| 850 | ABCD1 | 8.26 | 307.5 | P33897 | 745 | ABC transporter superfamily, ABCD family, Peroxisomal fatty acyl CoA transporter (TC 3.A.1.203) subfamily |
| 851 | AASDHPPT | 7.23 | 150.5 | Q9NRN7 | 309 | P-Pant transferase superfamily, AcpS family |
| 852 | ACSL6 | 7.06 | 133.5 | Q9UKU0 | 697 | ATP-dependent AMP-binding enzyme family |
| 853 | Guanylate Cyclase beta | 7.17 | 144.5 | Q02153 | 619 | Adenylyl cyclase class-4/guanylyl cyclase family |
| 854 | BAD | 7.54 | 186.5 | Q92934 | 168 | Bcl-2 family |
| 855 | HDAC1 | 7.06 | 133.5 | Q13547 | 482 | Histone deacetylase family, HD type 1 subfamily |
| 856 | HDAC10 | 7.1 | 137.5 | Q96958 | 669 | Histone deacetylase family, HD type 2 subfamily |
| 857 | HDAC3 | 7.32 | 159.5 | O15379 | 428 | Histone deacetylase family, HD type 1 subfamily |
| 858 | HDAC5 | 7.23 | 150.5 | Q9UQL6 | 1122 | Histone deacetylase family, HD type 2 subfamily |
| 859 | HDAC6 | 7.19 | 146 | Q9UBN7 | 1215 | Histone deacetylase family, HD type 2 subfamily |
| 860 | HDAC7 | 7.17 | 144.5 | Q8WUI4 | 952 | Histone deacetylase family, HD type 2 subfamily |
| 861 | HDAC9 | 7.26 | 153.5 | Q9UKV0 | 1011 | Histone deacetylase family, HD type 2 subfamily |
| 862 | Heregulin | 7.5 | 181.5 | Q15491 | 862 | — |
| 863 | HSP10 | 7.32 | 159.5 | P61604 | 102 | GroES chaperonin family |
| 864 | HSP105 | 7.55 | 187.5 | Q92598 | 858 | Heat shock protein 70 family |
| 865 | HSP40 | 7.32 | 160 | P25685 | 340 | — |
| 866 | HSP60 | 7.12 | 139 | P10809 | 573 | Chaperonin (HSP60) family |
| 867 | HSP90A | 10.12 | 1110.5 | P07900 | 732 | Heat shock protein 90 family |
| 868 | Integrin beta5 | 7.27 | 154.5 | P18084 | 799 | Integrin beta chain family |
| 869 | Involucrin | 7.39 | 167.5 | P07476 | 585 | Involucrin family |
| 870 | JAB1 | 7.59 | 192.5 | Q9UNS2 | 423 | CSN3 family |
| 871 | JM4 | 7.14 | 141.5 | O60831 | 178 | PRA1 family |
| 872 | Tubulin gamma | 7.23 | 150.5 | P23258 | 451 | Tubulin family |
| 873 | Tyrosinase | 6.98 | 126 | P14679 | 529 | Tyrosinase family |
| 874 | UBA2 | 7.08 | 135.5 | Q9UBT2 | 640 | Ubiquitin-activating E1 family |
| 875 | UBE1L | 7.27 | 154.5 | P41226 | 1012 | Ubiquitin-activating E1 family |
| 876 | Ubiquitin | 7.14 | 141.5 | P62988 | — | — |
| 877 | Urocortin | 7.21 | 148.5 | P55089 | 124 | Sauvagine/corticotropin-releasing factor/urotensin I family |
| 878 | USF2 | 7.14 | 141 | Q15853 | 346 | — |
| 879 | VEGFB | 7.45 | 175 | P49765 | 207 | PDGF/VEGF growth factor family |
| 880 | Vimentin | 7.29 | 157 | P08670 | 466 | Intermediate filament family |
| 881 | 60S Ribosomal Protein L10 | 7.21 | 148 | P27635 | 214 | Ribosomal protein L10e family |
| 882 | WNT1 | 7.24 | 151.5 | P04628 | 370 | Wnt family |
| 883 | XPA | 7.28 | 155 | P23025 | 273 | XPA family |
| 884 | XPF | 7.28 | 155.5 | Q92889 | 916 | XPF family |
| 885 | XRCC1 | 7.09 | 136.5 | P18887 | 633 | |
| 886 | XRCC2 | 7.19 | 146.5 | O3543 | 280 | RecA family, RAD51 subfamily |
| 887 | XRCC3 | 7.28 | 155.5 | O3542 | 346 | RecA family, RAD51 subfamily |
| 888 | XRCC4 | 7.38 | 167 | Q13426 | 336 | XRCC4 family |
| 889 | XRCC5 | 7.16 | 143 | P13010 | 732 | Ku80 family |
| 890 | XRCC6 | 7.07 | 134.5 | P12956 | 609 | Ku70 family |
| 891 | LRRK1 | 7.28 | 155.5 | Q385D2 | 2015 | Protein kinase superfamily, TKL Ser/Thr protein kinase family, ROCO subfamily |
| 892 | DAK | 7.22 | 149 | Q3LXA3 | 575 | Dihydroxyacetone kinase (DAK) family |
| 893 | ADCK5 | 7.05 | 132.5 | Q3MIX3 | 580 | Protein kinase superfamily, ADCK protein kinase family |
| 894 | FAKD1 | 7.12 | 139.5 | Q53R41 | 847 | FAST kinase family |
| 895 | SGOL1 | 7.55 | 188 | Q5FBB7 | 561 | Shugoshin family |
| 896 | DGKK | 7.48 | 178 | Q5KSL6 | 1271 | Eukaryotic diacylglycerol kinase family |
| 897 | RBM26 | 7.34 | 161.5 | Q5T8P6 | 1007 | — |

TABLE 2-continued

| ID | Antibody Name | Normalized data (log2) | Raw data | SwissProt | Length | Protein family |
|---|---|---|---|---|---|---|
| 898 | STEA3 | 7.57 | 189.5 | Q658P3 | 488 | STEAP family |
| 899 | STEAP4 | 7.2 | 147 | Q687X5 | 459 | STEAP family |
| 900 | TENS3 | 7.51 | 182 | Q68CZ2 | 1445 | — |
| 901 | LDOC1L | 7.55 | 188 | Q6ICC9 | 239 | LDOC1 family |
| 902 | DOK6 | 7.64 | 199 | Q6PKX4 | 331 | DOK family, Type B subfamily |
| 903 | KSR2 | 7.64 | 199 | Q6VAB6 | 950 | Protein kinase superfamily, TKL Ser/Thr protein kinase family |
| 904 | TSH1 | 7.48 | 179 | Q6ZSZ6 | 1077 | Teashirt C2H2-type zinc-finger protein family |
| 905 | MARK2 | 7.21 | 148.5 | Q7KZI7 | 788 | Protein kinase superfamily, CAMK Ser/Thr protein kinase family, SNF1 subfamily |
| 906 | DOK3 | 7.22 | 149 | Q7L591 | 496 | DOK family, Type A subfamily |
| 907 | ATBP3 | 7.61 | 195 | Q7Z7A3 | 348 | TtcA family, CTU1/NCS6/AIPBD3 subfamily |
| 908 | DGKH | 7.2 | 147 | Q86XP1 | 1220 | Eukaryotic diacylglycerol kinase family |
| 909 | LATH | 7.69 | 206 | Q86YQ2 | 179 | BPI/LBP/Plunc superfamily, Plunc family |
| 910 | Collagen XXV alpha1 | 6.91 | 120.5 | Q9BXS0 | 654 | — |
| 911 | COX11 | 7.48 | 178 | Q9Y6N1 | 276 | COX11/CtaG family |
| 912 | COX15 | 7.11 | 138 | Q7KZN9 | 410 | COX15/CtaA family |
| 913 | COX17 | 7.24 | 151 | Q14061 | 63 | COX17 family |
| 914 | COX19 | 7.69 | 207 | Q49B96 | 90 | COX19 family |
| 915 | COX41 | 7.37 | 165 | P13073 | 169 | Cytochrome c oxidase IV family |
| 916 | COX7S/A2 | 7.49 | 179.5 | O60397 | 106 | Cytochrome c oxidase VIIa family |
| 917 | Cytochrome P450 17A1 | 7.61 | 195 | P05093 | 508 | Cytochrome P450 family |
| 918 | Cytochrome P450 19A1 | 7.49 | 180 | P11511 | 503 | Cytochrome P450 family |
| 919 | Cytochrome P450 1A2 | 7.14 | 141 | P05177 | 515 | Cytochrome P450 family |
| 920 | Cytochrome P450 26A1 | 8.95 | 494 | O43174 | 497 | Cytochrome P450 family |
| 921 | Cytochrome P450 26C1 | 7.41 | 170 | Q6V0L0 | 522 | Cytochrome P450 family |
| 922 | Cytochrome P450 2A6 | 7.27 | 154 | P11509 | 494 | Cytochrome P450 family |
| 923 | Cytochrome P450 2A13 | 7.66 | 202.5 | Q16696 | 494 | Cytochrome P450 family |
| 924 | Cytochrome P450 2B6 | 8.11 | 276.5 | P20813 | 491 | Cytochrome P450 family |
| 925 | Cytochrome P450 2C8 | 7.11 | 138.5 | P10632 | 490 | Cytochrome P450 family |
| 926 | Cytochrome P450 2U1 | 7.35 | 163 | Q7Z449 | 544 | Cytochrome P450 family |
| 927 | Cytochrome P450 2W1 | 7.7 | 208 | Q8TAV3 | 490 | Cytochrome P450 family |
| 928 | Cytochrome P450 3A43 | 7.07 | 134.5 | Q9HB55 | 503 | Cytochrome P450 family |
| 929 | CST9L | 6.92 | 121.5 | Q9H4G1 | 147 | Cystatin family |
| 930 | CSTL1 | 7.11 | 138.5 | Q9H114 | 145 | Cystatin family |
| 931 | CST2 | 7.25 | 152 | P09228 | 141 | Cystatin family |
| 932 | CST1 | 7.06 | 133 | P01037 | 141 | Cystatin family |
| 933 | PLA2G4D | 7.2 | 147 | Q86XP0 | 818 | — |
| 934 | PLA2G4E | 7.35 | 163.5 | Q3MJ16 | 856 | — |
| 935 | PLA2G4C | 7.21 | 148.5 | Q9UP65 | 541 | — |
| 936 | GNPAT | 7.4 | 168.5 | O15228 | 680 | GPAT/DAPAT family |
| 937 | DMGDH | 7.25 | 152.5 | Q9UI17 | 866 | GcvT family |
| 938 | POLE1 | 7.21 | 148 | Q07864 | 2286 | DNA polymerase type-B family |
| 939 | POLI | 7.55 | 187.5 | Q9UNA4 | 740 | DNA polymerase type-Y family |
| 940 | POLD3 | 7.24 | 151 | Q15054 | 466 | — |
| 941 | POLG2 | 7.3 | 158 | Q9UHN1 | 485 | — |
| 942 | PRIM1 | 7.27 | 154.5 | P49642 | 420 | Eukaryotic-type primase small subunit family |
| 943 | CD3EAP | 7.82 | 225.5 | O15446 | 510 | Eukaryotic RPA34 RNA polymerase subunit family |
| 944 | RPC1 | 7.3 | 157.5 | O14802 | 1390 | RNA polymerase beta chain family |
| 945 | RPC4 | 7.22 | 149.5 | P05423 | 398 | Eukaryotic RPC4/POLR3D RNA polymerase subunit family |
| 946 | RPC8 | 7.17 | 144 | Q9Y535 | 204 | Eukaryotic RPB7/RPC8 RNA polymerase subunit family |
| 947 | DNAJB11 | 7.12 | 139 | Q9UBS4 | 358 | — |
| 948 | RASSF6 | 7.11 | 138.5 | Q6ZTQ3 | 369 | — |
| 949 | G3BP2 | 7.2 | 147 | Q9UN86 | 482 | Cytoplasm |
| 950 | RAB18 | 7.4 | 169 | Q9NP72 | 206 | Small GTPase superfamily, Rab family |
| 951 | RAB20 | 7.88 | 235.5 | Q9NX57 | 234 | Small GTPase superfamily, Rab family |
| 952 | RAB34 | 7.21 | 148.5 | Q9BZG1 | 259 | Small GTPase superfamily, Rab family |
| 953 | RAB37 | 7.76 | 217 | Q96AX2 | 223 | Small GTPase superfamily, Rab family |
| 954 | RAB38 | 7.24 | 151.5 | P57729 | 211 | Small GTPase superfamily, Rab family |
| 955 | RAB40B | 7.29 | 157 | Q12829 | 278 | Small GTPase superfamily, Rab family |
| 956 | RAB41 | 7.45 | 174.5 | Q5JT25 | 222 | Small GTPase superfamily, Rab family |
| 957 | RAB5C | 7.07 | 134.5 | P51148 | 216 | Small GTPase superfamily, Rab family |
| 958 | RAB6A | 7.27 | 154.5 | P20340 | 208 | Small GTPase superfamily, Rab family |
| 959 | RAB6C | 7.15 | 142 | Q9H0N0 | 254 | Small GTPase superfamily, Rab family |
| 960 | RAB7L1 | 7.25 | 152.5 | O14966 | 203 | Small GTPase superfamily, Rab family |
| 961 | RGS1 | 7.29 | 157 | Q08116 | 209 | — |
| 962 | UPF1 | 7.32 | 160 | Q92900 | 1129 | DNA2/NAM7 helicase family |
| 963 | REN | 7.65 | 201.5 | P00797 | 406 | Peptidase A1 family |
| 964 | RFPL4A | 7.27 | 154 | A6NLU0 | 287 | — |
| 965 | ALDH1A2 | 7.21 | 148 | O94788 | 518 | Aldehyde dehydrogenase family |
| 966 | RHG17 | 7.17 | 144.5 | Q68EM7 | 881 | — |

TABLE 2-continued

| ID | Antibody Name | Normalized data (log2) | Raw data | SwissProt | Length | Protein family |
|---|---|---|---|---|---|---|
| 967 | Histone H3 (Acetyl-Lys9) | 7.36 | 164 | P68431 | 136 | Histone H3 family |
| 968 | Histone H3 (Acetyl-Lys18) | 7.25 | 152 | P68431 | 136 | Histone H3 family |
| 969 | Histone H3 (Acetyl-Lys23) | 7.21 | 148 | P68431 | 136 | Histone H3 family |
| 970 | Histone H3 (Acetyl-Lys27) | 7.13 | 140.5 | P68431 | 136 | Histone H3 family |
| 971 | Histone H4 (Acetyl-Lys5) | 7.42 | 171.5 | P62805 | 103 | Histone H4 family |
| 972 | Histone H4 (Acetyl-Lys8) | 7.41 | 170.5 | P62805 | 103 | Histone H4 family |
| 973 | Histone H4 (Acetyl-Lys12) | 7.46 | 176 | P62805 | 103 | Histone H4 family |
| 974 | C3AR1 | 7.15 | 142 | Q16581 | 482 | G-protein coupled receptor 1 family |
| 975 | Aggrecan (Cleaved-Asp369) | 7.31 | 158.5 | P16112 | 2415 | Aggrecan/versican proteoglycan family |
| 976 | BAD (Cleaved-Asp71) | 7.12 | 139 | Q61337 | 204 | Bcl-2 family |
| 977 | Caspase 3 (Cleaved-Asp175) | 7.33 | 161 | P42574 | 277 | Peptidase C14A family |
| 978 | DFF45 (Cleaved-Asp224) | 7.42 | 171 | O00273 | 331 | — |
| 979 | IL-1beta (Cleaved-Asp210) | 7.16 | 143 | P29466 | 404 | Peptidase C14A family |
| 980 | Notch 1 (Cleaved-Val1754) | 7.25 | 152 | P46531 | 2555 | NOTCH family |
| 981 | Notch 2 (Cleaved-Asp1733) | 7.12 | 139 | Q04721 | 2471 | NOTCH family |
| 982 | FA10 (activated heavy chain, Cleaved-Ile235) | 7.34 | 162 | P00742 | 488 | Peptidase S1 family |
| 983 | ADAM 17 (Cleaved-Arg215) | 7.54 | 186.5 | P78536 | 824 | — |
| 984 | SPTA2 (Cleaved-Asp1185) | 7.37 | 165 | Q13813 | 2472 | Spectrin family |
| 985 | CASP3 (p17, Cleaved-Asp175) | 8.45 | 350.5 | P42574 | 277 | Peptidase C14A family |
| 986 | CD37 | 7 | 128 | P11049 | 281 | Tetraspanin (TM4SF) family |
| 987 | IKK Alpha | 7.02 | 130 | O15111 | 745 | Protein kinase superfamily, Ser/Thr protein kinase family, I-kappa-B kinase subfamily |
| 988 | MYL2 | 7.04 | 131.5 | P10916 | 166 | — |
| 989 | WNT5A | 7.04 | 131.5 | P41221 | 380 | Wnt family |
| 990 | LPL | 7.15 | 142.5 | P06858 | 475 | AB hydrolase superfamily, Lipase family |
| 991 | TrkA | 7.14 | 141.5 | P04629 | 796 | Protein kinase superfamily, Tyr protein kinase family, Insulin receptor subfamily |
| 992 | CD80 | 8.01 | 258.5 | P33681 | 288 | — |
| 993 | MYL3 | 6.99 | 127 | P08590 | 195 | — |
| 994 | CD18 (ITGB2) | 7.21 | 148.5 | P05107 | 769 | Integrin beta chain family |
| 995 | MUSK | 7.17 | 144 | O15146 | 869 | Protein kinase superfamily, Tyr protein kinase family |
| 996 | SOD1 | 7.54 | 185.5 | P00441 | 154 | Cu—Zn superoxide dismutase family |
| 997 | MPS1 | 7.18 | 145 | P42677 | 84 | Ribosomal protein S27e family |
| 998 | PAK2 | 7.14 | 141.5 | Q13177 | 524 | Protein kinase superfamily, STE Ser/Thr protein kinase family, STE20 subfamily |
| 999 | RTN3 | 7.18 | 145.5 | O95197 | 1032 | — |
| 1000 | PDGFR beta | 7.17 | 144.5 | P09619 | 1106 | Protein kinase superfamily, Tyr protein kinase family, CSF-1/PDGF receptor subfamily |
| 1001 | PROZ | 7.25 | 152.5 | P22891 | 400 | Peptidase S1 family |
| 1002 | ROR1 | 7.15 | 142 | Q01973 | 937 | Protein kinase superfamily, Tyr protein kinase family, ROR subfamily |
| 1003 | Proteinase 3 | 7.15 | 142.5 | P24158 | 256 | Peptidase S1 family, Elastase subfamily |
| 1004 | TUBB3 (Tubulin beta 3) | 7.38 | 166.5 | Q13509 | 450 | Tubulin family |
| 1005 | SLC25A21 | 7.17 | 144.5 | Q9BQT8 | 299 | Mitochondrial carrier family |
| 1006 | SLC6A16 | 7.37 | 165.5 | Q9GZN6 | 736 | Sodium:neurotransmitter symporter (SNF) (TC 2.A.22) family, SLC6A16 subfamily |
| 1007 | SLC6A15 | 7.18 | 145 | Q9H2J7 | 730 | Sodium:neurotransmitter symporter (SNF) (TC 2.A.22) family, SLC6A15 subfamily |
| 1008 | AFP | 7.09 | 136.5 | P02771 | 609 | ALB/AFP/VDB family |
| 1009 | beta-2-Microglobulin | 9.73 | 849 | P61769 | 119 | Beta-2-microglobulin family |
| 1010 | CEA | 6.97 | 125.5 | P11465 | 335 | Immunoglobulin superfamily, CEA family |
| 1011 | Ferritin | 7.1 | 137.5 | P02794 | 183 | Ferritin family |
| 1012 | Free PSA (KLK3) | 7.01 | 128.5 | P07288 | 261 | Peptidase S1 family, Kallikrein subfamily |
| 1013 | Total PSA | 7.07 | 134 | P07288 | 261 | Peptidase S1 family, Kallikrein subfamily |
| 1014 | PSA-ACT | 7.07 | 134.5 | P07288 | 261 | Peptidase S1 family, Kallikrein subfamily |
| 1015 | FSH | 7.08 | 135.5 | P01225 | 129 | Glycoprotein hormones subunit beta family |
| 1016 | alpha hCG | 7.04 | 131.5 | P01215 | 116 | Glycoprotein hormones subunit alpha family |
| 1017 | beta hCG | 7.1 | 137.5 | P01233 | 165 | Glycoprotein hormones subunit beta family |
| 1018 | hCG | 7.08 | 135 | P01215/P01233 | — | glycoprotein hormones subunit alpha family, glycoprotein hormones subunit beta family |

TABLE 2-continued

| ID | Antibody Name | Normalized data (log2) | Raw data | SwissProt | Length | Protein family |
|---|---|---|---|---|---|---|
| 1019 | HGH | 7.02 | 130 | P01241 | 217 | Somatotropin/prolactin family |
| 1020 | Insulin | 7.07 | 134.5 | P01308 | 110 | Insulin family |
| 1021 | LH | 7.1 | 137 | P01229 | 141 | Glycoprotein hormones subunit beta family |
| 1022 | Prolactin | 7.12 | 139 | P01236 | 227 | Somatotropin/prolactin family |
| 1023 | Testosterone | 9.64 | 800.5 | P04278 | 402 | — |
| 1024 | Keratin 15 | 8.23 | 300 | P19012 | 456 | Intermediate filament family |
| 1025 | Keratin 16 | 7.03 | 130.5 | P08779 | 473 | Intermediate filament family |
| 1026 | Keratin 17 | 7.32 | 160 | Q04695 | 432 | Intermediate filament family |
| 1027 | Keratin 18 | 7.28 | 155 | P05783 | 430 | Intermediate filament family |
| 1028 | Keratin 19 | 7.17 | 144 | P08727 | 400 | Intermediate filament family |
| 1029 | Keratin 20 | 7.29 | 157 | P35900 | 424 | Intermediate filament family |
| 1030 | Keratin 5 | 7.29 | 157 | P13647 | 590 | Intermediate filament family |
| 1031 | Keratin 7 | 7.26 | 153 | P08729 | 469 | Intermediate filament family |
| 1032 | Keratin 8 | 7.14 | 141 | P05787 | 483 | Intermediate filament family |
| 1033 | Keratin 10 | 7.52 | 183 | P13645 | 584 | Intermediate filament family |
| 1034 | Ki67 | 7.29 | 156 | P46013 | 3256 | — |
| 1035 | iNOS | 7.71 | 209.5 | P35228 | 1153 | NOS family |
| 1036 | Ku70/80 | 7.14 | 141.5 | P13010 | 732 | Ku80 family |
| 1037 | Ku70 | 7.18 | 145.5 | P12956 | 609 | Ku70 family |
| 1038 | MAGE-1 | 7.42 | 171.5 | P43355 | 309 | |
| 1039 | Mammaglobin | 7.14 | 141.5 | Q13296 | 93 | Secretoglobin family, Lipophilin subfamily |
| 1040 | Mammaglobin B | 7.41 | 170 | O75556 | 95 | Secretoglobin family, Lipophilin subfamily |
| 1041 | MART-1 | 7.52 | 184 | Q16655 | 118 | — |
| 1042 | MCL1 | 7.46 | 176.5 | Q07820 | 350 | Bcl-2 family |
| 1043 | TAF4 | 7.07 | 134 | O00268 | 1085 | TAF4 family |
| 1044 | CDC7 | 7.32 | 160 | O00311 | 574 | Protein kinase superfamily, Ser/Thr protein kinase family, CDC7 subfamily |
| 1045 | LHR2A | 7.68 | 205 | O00534 | 786 | — |
| 1046 | CDKA1 | 7.14 | 141.5 | O14519 | 115 | CDK2AP family |
| 1047 | TP53I11 | 7.33 | 161 | O14683 | 189 | — |
| 1048 | TNF11 | 7.38 | 167 | O14788 | 317 | Tumor necrosis factor family |
| 1049 | BACH1 | 7.1 | 137 | O14867 | 736 | BZIP family, CNC subfamily |
| 1050 | MAST4 | 7.5 | 180.5 | O15021 | 2626 | Protein kinase superfamily, AGC Ser/Thr protein kinase family |
| 1051 | EPHB6 | 7.32 | 160 | O15197 | 1021 | Protein kinase superfamily, Tyr protein kinase family, Fphrin receptor subfamily |
| 1052 | p73 | 7.46 | 176.5 | O15350 | 636 | P53 family |
| 1053 | M3K13 | 7.9 | 238.5 | O43283 | 966 | Protein kinase superfamily, STE Ser/Thr protein kinase family, MAP kinase kinase kinase subfamily |
| 1054 | TPD54 | 7.67 | 204 | O43399 | 206 | TPD52 family |
| 1055 | TNF12 | 7.44 | 173.5 | O43508 | 249 | Tumor necrosis factor family |
| 1056 | TNF14 | 7.24 | 151 | O43557 | 240 | Tumor necrosis factor family |
| 1057 | BUB1 | 7.41 | 170 | O43683 | 1085 | Protein kinase superfamily, Ser/Thr protein kinase family, BUB1 subfamily |
| 1058 | AIRE | 7.27 | 154 | O43918 | 545 | — |
| 1059 | EFNA2 | 7.39 | 168 | O43921 | 213 | Ephrin family |
| 1060 | MAST3 | 7.7 | 208.5 | O60307 | 1309 | Protein kinase superfamily, AGC Ser/Thr protein kinase family |
| 1061 | SDCG1 | 7.82 | 226 | O60524 | 1076 | NEMF family |
| 1062 | MAP4K3 | 7.12 | 139 | Q8IVH8 | 894 | Protein kinase superfamily, STE Ser/Thr protein kinase family, STE20 subfamily |
| 1063 | CDKL3 | 7.16 | 143 | Q8IVW4 | 592 | Protein kinase superfamily, CMGC Ser/Thr protein kinase family, CDC2/CDKX subfamily |
| 1064 | TUSC5 | 7.12 | 139 | Q8IXB3 | 177 | CD225/Dispanin family |
| 1065 | TP53INP2 | 7.37 | 165.5 | Q8CFU8 | 221 | — |
| 1066 | KIAA1967 | 7.29 | 156.5 | Q8N163 | 923 | — |
| 1067 | MAP4K6 | 7.23 | 150.5 | Q8N4C8 | 1332 | Protein kinase superfamily, STE Ser/Thr protein kinase family, STE20 subfamily |
| 1068 | CKI-alpha1/L | 7.5 | 181.5 | Q8N752 | 337 | Protein kinase superfamily, CK1 Ser/Thr protein kinase family, Casein kinase I subfamily |
| 1069 | CAMK5 | 7.22 | 149.5 | Q8NCB2 | 501 | Protein kinase superfamily, CAMK Ser/Thr protein kinase family |
| 1070 | HIPK4 | 7.4 | 169 | Q8NE63 | 616 | Protein kinase superfamily, CMGC Ser/Thr protein kinase family, HIPK subfamily |
| 1071 | PPHLN | 7.29 | 156.5 | Q8NEY8 | 458 | — |
| 1072 | STEA2 | 7.29 | 156 | Q8NFT2 | 490 | STEAP family |
| 1073 | AGR3 | 7.86 | 232 | Q8TD06 | 166 | AGR family |
| 1074 | MAPK15 | 7.34 | 161.5 | Q8TD08 | 544 | Protein kinase superfamily, CMGC Ser/Thr protein kinase family, MAP kinase subfamily |
| 1075 | BRSK1 | 7.4 | 168.5 | Q8TDC3 | 778 | Protein kinase superfamily, CAMK Ser/Thr protein kinase family, SNF1 subfamily |

TABLE 2-continued

| ID | Antibody Name | Normalized data (log2) | Raw data | SwissProt | Length | Protein family |
|---|---|---|---|---|---|---|
| 1076 | DOK4 | 7.21 | 148 | Q8TEW6 | 326 | DOK family, Type B subfamily |
| 1077 | GRK7 | 8.59 | 385.5 | Q8WTQ7 | 553 | Protein kinase superfamily, AGC Ser/Thr protein kinase family, GPRK subfamily |
| 1078 | ORAV1 | 7.77 | 218 | Q8WV07 | 137 | ORAOV1 family |
| 1079 | MADD | 7.14 | 141 | Q8WXG6 | 1647 | MADD family |
| 1080 | CNKR2 | 7.08 | 135.5 | Q8WXI2 | 1034 | CNKSR family |
| 1081 | Cytochrome P450 39A1 | 7.41 | 170.5 | Q9NYL5 | 469 | Cytochrome P450 family |
| 1082 | Cytochrome P450 3A4/5 | 7.29 | 157 | P08684 | 503 | Cytochrome P450 family |
| 1083 | Cytochrome P450 4F2 | 7.25 | 152.5 | P78329 | 520 | Cytochrome P450 family |
| 1084 | Cytochrome P450 4X1 | 7.16 | 143 | Q8N118 | 509 | Cytochrome P450 family |
| 1085 | CYTL1 | 7.1 | 137 | Q9NRR1 | 136 | — |
| 1086 | DNAJB4 | 7.34 | 161.5 | Q9UDY4 | 337 | — |
| 1087 | FGF18 | 7.13 | 140.5 | O76093 | 207 | Heparin-binding growth factors family |
| 1088 | FRS3 | 7.24 | 151 | O43559 | 492 | — |
| 1089 | GRID2 | 7.38 | 166 | O43424 | 1007 | Glutamate-gated ion channel (TC 1.A.10.1) family, GRID2 subfamily |
| 1090 | HSPB2 | 7.38 | 166 | Q16082 | 182 | Small heat shock protein (HSP20) family |
| 1091 | IL20RB | 7.21 | 148 | Q6UXL0 | 311 | Type II cytokine receptor family |
| 1092 | MAPK9 | 7.76 | 217 | P45984 | 424 | Protein kinase superfamily, CMGC Ser/Thr protein kinase family, MAP kinase subfamily |
| 1093 | Cyclosome 1 | 7.35 | 163.5 | Q9H1A4 | 1944 | APC1 family |
| 1094 | PRKAB1 | 7.41 | 169.5 | Q9Y478 | 270 | 5'-AMP-activated protein kinase beta subunit family |
| 1095 | BARD1 | 7.11 | 138 | Q99728 | 777 | — |
| 1096 | BCLW | 7.48 | 178 | Q92843 | 193 | Bcl-2 family |
| 1097 | CIDEB | 7.69 | 206 | Q9UHD4 | 219 | — |
| 1098 | DCC | 7.29 | 156 | P43146 | 1447 | Immunoglobulin superfamily, DCC family |
| 1099 | DFFA | 7.76 | 216.5 | O00273 | 331 | — |
| 1100 | DNAL1 | 7.16 | 143.5 | Q4LDG9 | 190 | Dynein light chain LC1-type family |
| 1101 | DNAL4 | 7.19 | 146.5 | O96015 | 105 | Dynein light chain family |
| 1102 | March2 | 7.29 | 156 | Q9P0N8 | 246 | — |
| 1103 | March3 | 7.48 | 178 | Q86UD3 | 253 | — |
| 1104 | March4 | 7.19 | 146 | Q9P2E8 | 410 | — |
| 1105 | March5 | 7.3 | 157.5 | Q9NX47 | 278 | — |
| 1106 | MYLIP | 7.6 | 193.5 | Q8WY64 | 445 | — |
| 1107 | RFWD2 | 7.54 | 186 | Q8NHY2 | 731 | COP1 family |
| 1108 | UBR1 | 7.8 | 223 | Q8IWV7 | 1749 | UBR1 family |
| 1109 | ELOVL3 | 7.25 | 152.5 | Q9HB03 | 270 | ELO family |
| 1110 | ELOVL4 | 7.21 | 148.5 | Q9GZR5 | 314 | ELO family |
| 1111 | ELOVL5 | 7.43 | 173 | Q9NYP7 | 299 | ELO family |
| 1112 | ENDOGL1 | 7.28 | 155.5 | Q9Y2C4 | 368 | DNA/RNA non-specific endonuclease family |
| 1113 | EPHB1/2/3 | 7.61 | 196 | P54762 | 984 | Protein kinase superfamily, Tyr protein kinase family, Ephrin receptor subfamily |
| 1114 | EPN3 | 7.33 | 161 | Q9H201 | 632 | Epsin family |
| 1115 | FKBPL | 7.39 | 167.5 | Q9UIM3 | 349 | — |
| 1116 | FOXJ3 | 7.23 | 150 | Q9UPW0 | 622 | — |
| 1117 | FOXN4 | 7.16 | 143 | Q96NZ1 | 517 | — |
| 1118 | FOXR1 | 7.2 | 147 | Q6PIV2 | 292 | — |
| 1119 | RHG22 | 7.18 | 145.5 | Q7Z5H3 | 698 | — |
| 1120 | RHG9 | 7.11 | 138 | Q9BRR9 | 750 | — |
| 1121 | ARHGEF10 | 7.35 | 163 | O15013 | 1369 | — |
| 1122 | ARHGEF12 | 7.23 | 150.5 | Q9NZN5 | 1544 | — |
| 1123 | ARHGEF3 | 7.08 | 135.5 | Q9NR81 | 526 | — |
| 1124 | ARHGEF5 | 7.42 | 171 | Q12774 | 1597 | — |
| 1125 | ARHGEF9 | 7.11 | 138.5 | O43307 | 516 | — |
| 1126 | ARHGEF2 | 7.53 | 184.5 | Q92974 | 986 | — |
| 1127 | RHOBTB3 | 7.29 | 157 | O94955 | 611 | — |
| 1128 | Septin-2 | 7.34 | 162 | Q15019 | 361 | Septin family |
| 1129 | Septin-7 | 7.15 | 142 | Q16181 | 437 | Septin family |
| 1130 | Septin-8 | 7.4 | 168.5 | Q92599 | 483 | Septin family |
| 1131 | SPINK6 | 7.24 | 151.5 | Q6UWN8 | 80 | — |
| 1132 | STK24 | 7.16 | 143.5 | Q9Y6E0 | 443 | Protein kinase superfamily, STE Ser/Thr protein kinase family, STE20 subfamily |
| 1133 | STK36 | 7.39 | 168 | Q9NRP7 | 1315 | Protein kinase superfamily, Ser/Thr protein kinase family |
| 1134 | PLK2 | 7.42 | 171.5 | Q9NYY3 | 685 | Protein kinase superfamily, Ser/Thr protein kinase family, CDC5/Polo subfamily |
| 1135 | PLK3 | 7.16 | 143.5 | Q9H4B4 | 646 | Protein kinase superfamily, Ser/Thr protein kinase family, CDC5/Polo subfamily |
| 1136 | PLK5 | 7.79 | 221.5 | Q496M5 | 336 | Protein kinase superfamily, Ser/Thr protein kinase family, CDC5/Polo subfamily |
| 1137 | PRKX | 7.34 | 162 | P51817 | 358 | Protein kinase superfamily, AGC Ser/Thr protein kinase family, cAMP subfamily |

TABLE 2-continued

| ID | Antibody Name | Normalized data (log2) | Raw data | SwissProt | Length | Protein family |
|---|---|---|---|---|---|---|
| 1138 | CATD (light chain, Cleaved-Gly65) | 7.15 | 142 | P07339 | 412 | Peptidase A1 family |
| 1139 | CATD (heavy chain, Cleaved-Leu169) | 7.24 | 151 | P07339 | 412 | Peptidase A1 family |
| 1140 | CATG (Cleaved-Ile21) | 7.18 | 145 | P08311 | 255 | Peptidase S1 family |
| 1141 | CATL1 (heavy chain, Cleaved-Thr288) | 7.11 | 138 | P07711 | 333 | Peptidase C1 family |
| 1142 | CATL2 (Cleaved-Leu114) | 7.27 | 154 | O60911 | 334 | Peptidase C1 family |
| 1143 | CATZ (Cleaved-Leu62) | 7.42 | 171 | Q9UBR2 | 303 | Peptidase C1 family |
| 1144 | CD97beta (Cleaved-Ser531) | 7.63 | 198 | P48960 | 835 | G-protein coupled receptor 2 family, LN-TM7 subfamily |
| 1145 | FA12 (heavy chain, Cleaved-Arg372) | 7.23 | 150.5 | P00748 | 615 | Peptidase S1 family |
| 1146 | FA13A (Cleaved-Gly39) | 7.2 | 147.5 | P00488 | 732 | Transglutaminase superfamily, Transglutaminase family |
| 1147 | Collagen III alpha1 (Cleaved-Gly1221) | 7.1 | 137.5 | P02461 | 1466 | Fibrillar collagen family |
| 1148 | Collagen I alpha2 (Cleaved-Gly1102) | 7.13 | 140 | P08123 | 1366 | Fibrillar collagen family |
| 1149 | Collagen IV alpha3 (Cleaved-Leu1425) | 7.37 | 165 | Q01955 | 1670 | Type IV collagen family |
| 1150 | Collagen IV alpha3 (Cleaved-Pro1426) | 7.21 | 148 | Q01955 | 1670 | Type IV collagen family |
| 1151 | C1R (light chain, Cleaved-Ile464) | 7.73 | 213 | P00736 | 705 | Peptidase S1 family |
| 1152 | C1S (heavy chain, Cleaved-Arg437) | 7.52 | 183.5 | P09871 | 688 | Peptidase S1 family |
| 1153 | CFAB Bb (Cleaved-Lys260) | 7.1 | 137 | P00751 | 764 | Peptidase S1 family |
| 1154 | MASP1 (heavy chain, Cleaved-Arg448) | 7.38 | 166 | P48740 | 699 | Peptidase S1 family |
| 1155 | Dipeptidyl-peptidase 1 (heavy chain, Cleaved-Arg394) | 7.15 | 142 | P53634 | 463 | Peptidase C1 family |
| 1156 | FA7 (light chain, Cleaved-Arg212) | 7.41 | 169.5 | P08709 | 466 | Peptidase S1 family |
| 1157 | FOXA2 | 7 | 128 | Q9Y261 | 457 | — |
| 1158 | Neurogenin-3 | 7.07 | 134 | Q9Y4Z2 | 214 | — |
| 1159 | NKX2.5 | 7.1 | 137 | P52952 | 324 | NK-2 homeobox family |
| 1160 | DAXX | 7.09 | 136 | Q9UER7 | 740 | DAXX family |
| 1161 | MATK (CTK) | 7.14 | 141.5 | P42679 | 507 | Protein kinase superfamily, Tyr protein kinase family, CSK subfamily |
| 1162 | WNT 108 | 7.23 | 150 | O00744 | 389 | Wnt family |
| 1163 | eNOS | 7.33 | 161 | P29474 | 1203 | NOS family |
| 1164 | JAK3 | 7.21 | 148.5 | P52333 | 1124 | Protein kinase superfamily, Tyr protein kinase family, JAK subfamily |
| 1165 | DDX4 | 7.07 | 134 | Q9NQI0 | 724 | DEAD box helicase family, DDX4/VASA subfamily |
| 1166 | ITGA5 | 7.15 | 142.5 | P08648 | 1049 | Integrin alpha chain family |
| 1167 | CD38 | 7.29 | 156 | P28907 | 300 | ADP-ribosyl cyclase family |
| 1168 | EGF | 7.21 | 148.5 | P01133 | 1207 | — |
| 1169 | NGFR | 7.15 | 142 | P08138 | 427 | — |
| 1170 | AKT2 | 7.23 | 150 | P31751 | 481 | Protein kinase superfamily, AGC Ser/Thr protein kinase family, RAC subfamily |
| 1171 | Pirh2 (RCHY1) | 7.07 | 134 | Q96PM5 | 261 | — |
| 1172 | CSF-1 (MCSF) | 7.24 | 151.5 | P09603 | 554 | — |
| 1173 | MAP2K2 (MEK2) | 7.26 | 153.5 | P36507 | 400 | Protein kinase superfamily, STE Ser/Thr protein kinase family, MAP kinase kinase subfamily |
| 1174 | PARP | 7.27 | 154 | P09874 | 1014 | — |
| 1175 | CD247 (CD3Z) | 7.1 | 137 | P20963 | 164 | CD3Z/FCER1G family |
| 1176 | TSH | 6.93 | 122 | P01222 | 138 | Glycoprotein hormones subunit beta family |
| 1177 | CRP | 7.45 | 174.5 | P02741 | 224 | Pentaxin family |
| 1178 | IgA | 7.07 | 134 | 0 | — | — |
| 1179 | IgE | 6.98 | 126 | 0 | — | — |
| 1180 | IgM | 7.04 | 132 | 0 | — | — |
| 1181 | IgG | 7.11 | 138.5 | 0 | — | — |
| 1182 | PKM2 | 7.27 | 154.5 | P14618 | 531 | Pyruvate kinase family |
| 1183 | Laminin | 7.14 | 141.5 | Q9Y6N6 | 1575 | — |
| 1184 | Fibronectin | 7.09 | 136.5 | P02751 | 2386 | — |
| 1185 | Hepatitis B Surface Antigen | 7.03 | 131 | N/A | — | — |
| 1186 | CA19-9 | 7.01 | 129 | P78552 | 427 | Type I cytokine receptor family, Type 5 subfamily |
| 1187 | CA 15-3 | 7.11 | 138 | P15941 | 1255 | — |
| 1188 | ZAP70 | 7.17 | 144.5 | P43403 | 619 | Protein kinase superfamily, Tyr protein kinase family, SYK/ZAP-70 subfamily |

TABLE 2-continued

| ID | Antibody Name | Normalized data (log2) | Raw data | SwissProt | Length | Protein family |
|---|---|---|---|---|---|---|
| 1189 | C-Kit | 7.59 | 192.5 | P10721 | 976 | Protein kinase superfamily, Tyr protein kinase family, CSF-1/PDGF receptor subfamily |
| 1190 | GSK3 alpha | 7.2 | 147.5 | P49840 | 483 | Protein kinase superfamily, CMGC Ser/Thr protein kinase family, GSK-3 subfamily |
| 1191 | IGF 1R | 7.29 | 156 | P08069 | 1367 | Protein kinase superfamily, Tyr protein kinase family, Insulin receptor subfamily |
| 1192 | Survivin | 7.13 | 140 | O15392 | 142 | IAP family |
| 1193 | KDR (VEGFR2) | 7.19 | 146.5 | P35968 | 1356 | Protein kinase superfamily, Tyr protein kinase family, CSF-1/PDGF receptor subfamily |
| 1194 | PTEN | 7.2 | 147.5 | P60484 | 403 | — |
| 1195 | MCM2 | 7.13 | 140 | P49736 | 904 | MCM family |
| 1196 | MCM5 | 7.17 | 144.5 | P33992 | 734 | MCM family |
| 1197 | MDM2 | 7.2 | 147 | Q00987 | 491 | MDM2/MDM4 family |
| 1198 | MMP-1 | 7.38 | 166 | P03956 | 469 | Peptidase M10A family |
| 1199 | MMP-10 | 8.35 | 327 | P09238 | 476 | Peptidase M10A family |
| 1200 | MMP-11 | 7.23 | 150.5 | P24347 | 488 | Peptidase M10A family |
| 1201 | MMP-13 | 7.54 | 185.5 | P45452 | 471 | Peptidase M10A family |
| 1202 | MMP-14 | 7.24 | 151 | P50281 | 582 | Peptidase M10A family |
| 1203 | MMP-15 | 7.37 | 165.5 | P51511 | 669 | Peptidase M10A family |
| 1204 | MMP-16 | 7.24 | 151.5 | P51512 | 607 | Peptidase M10A family |
| 1205 | MMP-19 | 7.29 | 156.5 | Q99542 | 508 | Peptidase M10A family |
| 1206 | MMP-2 | 8.39 | 335 | P08253 | 660 | Peptidase M10A family |
| 1207 | MMP-23 | 7.2 | 147.5 | O75900 | 390 | Peptidase M10A family |
| 1208 | MMP-3 | 7.15 | 142 | P08254 | 477 | Peptidase M10A family |
| 1209 | MMP-7 | 7.16 | 143 | P09237 | 267 | Peptidase M10A family |
| 1210 | MMP-8 | 7.28 | 155 | P22894 | 467 | Peptidase M10A family |
| 1211 | MMP-9 | 7.12 | 139 | P14780 | 707 | Peptidase M10A family |
| 1212 | NCK2 | 7.31 | 159 | O43639 | 380 | — |
| 1213 | NKX3.1 | 7.31 | 158.5 | Q99801 | 234 | NK-3 homeobox family |
| 1214 | BUB1B | 7.19 | 146.5 | O60566 | 1050 | Protein kinase superfamily, Ser/Thr protein kinase family, BUB1 subfamily |
| 1215 | DNA Polymerase zeta | 7.35 | 163.5 | O60673 | 3130 | DNA polymerase type-B family |
| 1216 | 6-Phosphofructo-2-Kinase | 7.28 | 155.5 | O60825 | 505 | Phosphoglycerate mutase family |
| 1217 | Dyskerin | 7.31 | 159 | O60832 | 514 | Pseudouridine synthase TruB family |
| 1218 | LAT3 | 7.98 | 252.5 | O75387 | 559 | SLC43A transporter (TC 2.A.1.44) family |
| 1219 | TACC1 | 7.64 | 199 | O75410 | 805 | TACC family |
| 1220 | DNA Polymerase theta | 7.33 | 160.5 | O75417 | 2590 | DNA polymerase type-A family |
| 1221 | TAF5L | 7.71 | 210 | O75529 | 589 | WD repeat TAF5 family |
| 1222 | CIB2 | 7.45 | 174.5 | O75838 | 187 | — |
| 1223 | TALL-2 | 7.29 | 156.5 | O75888 | 250 | Tumor necrosis factor family |
| 1224 | TUSC2 | 7.63 | 198.5 | O75896 | 110 | TUSC2 family |
| 1225 | CDKA2 | 7.28 | 155.5 | O75956 | 126 | CDK2AP family |
| 1226 | MEKKK 4 | 7.41 | 170 | O95819 | 1239 | Protein kinase superfamily, STE Ser/Thr protein kinase family, STE20 subfamily |
| 1227 | TOP3B | 7.49 | 180 | O95985 | 862 | Type IA topoisomerase family |
| 1228 | PTTG1 | 7.69 | 206 | O95997 | 202 | Securin family |
| 1229 | ABL1 | 7.48 | 178 | P00519 | 1130 | Protein kinase superfamily, Tyr protein kinase family, ABL subfamily |
| 1230 | TNFA | 8.14 | 283 | P01375 | — | — |
| 1231 | KITH | 7.46 | 176.5 | P04183 | 234 | Thymidine kinase family |
| 1232 | CDC2 | 7.58 | 192 | P06493 | 297 | Protein kinase superfamily, CMGC Ser/Thr protein kinase family, CDC2/CDKX subfamily |
| 1233 | BRI3B | 7.29 | 156 | Q8WY22 | 251 | — |
| 1234 | Septin-1 | 7.85 | 230 | Q8WYJ6 | 367 | Septin family |
| 1235 | AP2C | 7.33 | 160.5 | Q92754 | 450 | AP-2 family |
| 1236 | CDKL2 | 7.89 | 237.5 | Q92772 | 493 | Protein kinase superfamily, CMGC Ser/Thr protein kinase family, CDC2/CDKX subfamily |
| 1237 | TAF15 | 7.37 | 165 | Q92804 | 592 | RRM TET family |
| 1238 | MEKKK 1 | 7.38 | 166 | Q92918 | 833 | Protein kinase superfamily, STE Ser/Thr protein kinase family, STE20 subfamily |
| 1239 | Histone H2B | 7.45 | 175 | Q93079 | 126 | Histone H2B family |
| 1240 | TP53INP1 | 7.75 | 216 | Q96A56 | 240 | — |
| 1241 | ORCTL-2 | 7.65 | 200.5 | Q96BI1 | 424 | Major facilitator (TC 2.A.1) superfamily, Organic cation transporter (TC 2.A.1.19) family |
| 1242 | IP3KC | 7.41 | 169.5 | Q96DU7 | 683 | Inositol phosphokinase (IPK) family |
| 1243 | FAM84B | 7.37 | 165 | Q96KN1 | 310 | FAM84 family |
| 1244 | CIB3 | 7.26 | 153.5 | Q96Q77 | 187 | — |
| 1245 | SERC2 | 7.45 | 174.5 | Q96SA4 | 455 | TDE1 family |

TABLE 2-continued

| ID | Antibody Name | Normalized data (log2) | Raw data | SwissProt | Length | Protein family |
|---|---|---|---|---|---|---|
| 1246 | MAP3K3 | 7.36 | 164.5 | Q99759 | 626 | Protein kinase superfamily, STE Ser/Thr protein kinase family, MAP kinase kinase kinase subfamily |
| 1247 | FOXB1/2 | 7.32 | 159.5 | Q99853 | 325 | — |
| 1248 | ATF6B | 7.52 | 184 | Q99941 | 703 | BZIP family, ATF subfamily |
| 1249 | IPKB | 7.24 | 151 | Q9C010 | 78 | PKI family |
| 1250 | PBOV1 | 7.17 | 144.5 | Q9GZY1 | 135 | — |
| 1251 | ILKAP | 7.45 | 174.5 | Q9H0C8 | 392 | PP2C family |
| 1252 | GRAH | 7.4 | 169 | P20718 | 246 | Peptidase S1 family, Granzyme subfamily |
| 1253 | EIF4G2 | 7.46 | 175.5 | P78344 | 907 | EIF4G family |
| 1254 | LAMA3 | 7.29 | 156 | Q16787 | 3333 | — |
| 1255 | LAMA4 | 7.76 | 217 | Q16363 | 1823 | — |
| 1256 | LAMA5 | 7.31 | 158.5 | Q15230 | 3695 | — |
| 1257 | LAMB2 | 7.51 | 182.5 | P55268 | 1798 | — |
| 1258 | LAMB3 | 7.69 | 206.5 | Q13751 | 1172 | — |
| 1259 | LAMC3 | 7.4 | 168.5 | Q9Y6N6 | 1575 | — |
| 1260 | LEG4 | 7.35 | 163 | P56470 | 323 | — |
| 1261 | LEG7 | 7.59 | 193 | P47929 | 136 | — |
| 1262 | LEG9 | 7.29 | 156 | O00182 | 355 | — |
| 1263 | MGMT | 7.91 | 240 | P16455 | 207 | MGMT family |
| 1264 | MIPT3 | 7.22 | 149 | Q8TDR0 | 691 | TRAF3IP1 family |
| 1265 | MLH3 | 7.85 | 231 | Q9UHC1 | 1453 | DNA mismatch repair MutL/HexB family |
| 1266 | MSH2 | 8.32 | 318.5 | P43246 | 934 | DNA mismatch repair MutS family |
| 1267 | MSH3 | 7.49 | 179.5 | P20585 | 1137 | DNA mismatch repair MutS family, MSH3 subfamily |
| 1268 | MSH6 | 7.46 | 175.5 | P52701 | 1360 | DNA mismatch repair MutS family |
| 1269 | MUTYH | 7.75 | 215.5 | Q9UIF7 | 546 | Nth/MutY family |
| 1270 | NF1 | 7.5 | 181 | P21359 | 2839 | — |
| 1271 | FMN2 | 7.17 | 144 | Q9NZ56 | 1722 | Formin homology family, Cappuccino subfamily |
| 1272 | ALDOB | 7.22 | 149 | P05062 | 364 | Class I fructose-bisphosphate aldolase family |
| 1273 | ALDOC | 7.25 | 152 | P09972 | 364 | Class I fructose-bisphosphate aldolase family |
| 1274 | KCNJ9 | 7.44 | 174 | Q92806 | 393 | Inward rectifier-type potassium channel (TC 1.A.2.1) family, KCNJ9 subfamily |
| 1275 | GPRIN1 | 7.43 | 172 | Q7Z2K8 | 1008 | — |
| 1276 | GPRIN2 | 7.51 | 182 | O60269 | 458 | — |
| 1277 | GPRIN3 | 7.24 | 151 | Q6ZVF9 | 776 | — |
| 1278 | GABRA6 | 7.29 | 156 | Q16445 | 453 | Ligand-gated ion channel (TC 1.A.9) family, Gamma-aminobutyric acid receptor (TC 1.A.9.5) subfamily, GABRA6 sub-subfamily |
| 1279 | GABRG1 | 7.34 | 162.5 | Q8N1C3 | 465 | Ligand-gated ion channel (TC 1.A.9) family, Gamma-aminobutyric acid receptor (TC 1.A.9.5) subfamily, GABRG1 sub-subfamily |
| 1280 | GGH | 7.42 | 171.5 | Q92820 | 318 | Peptidase C26 family |
| 1281 | TUBGCP3 | 7.41 | 169.5 | Q96CW5 | 907 | TUBGCP family |
| 1282 | TUBGCP4 | 7.33 | 161 | Q9UGJ1 | 667 | TUBGCP family |
| 1283 | TUBGCP5 | 7.32 | 159.5 | Q96RT8 | 1024 | TUBGCP family |
| 1284 | TUBGCP6 | 7.41 | 170.5 | Q96RT7 | 1819 | TUBGCP family |
| 1285 | GADD45GIP1 | 7.5 | 181.5 | Q8TAE8 | 222 | — |
| 1286 | GRB14 | 9.42 | 684 | Q14449 | 540 | GRB7/10/14 family |
| 1287 | GRTP1 | 7.38 | 166 | Q5TC63 | 336 | — |
| 1288 | GAS1 | 7.26 | 153.5 | P54826 | 345 | — |
| 1289 | ERAS | 7.53 | 184.5 | Q7Z444 | 233 | Small GTPase superfamily, Ras family |
| 1290 | PRKY | 7.11 | 138 | O43930 | 277 | Protein kinase superfamily, Ser/Thr protein kinase family, cAMP subfamily |
| 1291 | QSK | 7.36 | 164.5 | Q9Y2K2 | 1263 | Protein kinase superfamily, CAMK Ser/Thr protein kinase family, SNF1 subfamily |
| 1292 | SRPK1 | 7.69 | 206.5 | Q96SB4 | 655 | Protein kinase superfamily, CMGC Ser/Thr protein kinase family |
| 1293 | TNNI3K | 7.7 | 207.5 | Q59H18 | 835 | Protein kinase superfamily, TKL Ser/Thr protein kinase family, MAP kinase kinase kinase subfamily |
| 1294 | ULK3 | 7.39 | 167.5 | Q6PHR2 | 472 | Protein kinase superfamily, Ser/Thr protein kinase family, APG1/unc-51/ULK1 subfamily |
| 1295 | SERPINB7 | 7.67 | 204 | O75635 | 380 | Serpin family, Ov-serpin subfamily |
| 1296 | SERPINB9 | 8.16 | 286 | P50453 | 376 | Serpin family, Ov-serpin subfamily |
| 1297 | SAA4 | 7.38 | 166 | P35542 | 130 | SAA family |
| 1298 | SESN1 | 7.23 | 150.5 | Q9Y6P5 | 492 | Sestrin family |
| 1299 | SHD | 7.45 | 175 | Q96IW2 | 340 | — |
| 1300 | SHC2 | 7.58 | 191 | P98077 | 582 | — |
| 1301 | SHC3 | 7.29 | 156 | Q92529 | 594 | — |
| 1302 | SIRPB1 | 7.77 | 218.5 | O00241 | 398 | — |
| 1303 | SIRPG | 7.64 | 199 | Q9P1W8 | 387 | — |

TABLE 2-continued

| ID | Antibody Name | Normalized data (log2) | Raw data | SwissProt | Length | Protein family |
|---|---|---|---|---|---|---|
| 1304 | SLC6A6 | 7.34 | 162 | P31641 | 620 | Sodium:neurotransmitter symporter (SNF) (TC 2.A.22) family, SLC6A6 subfamily |
| 1305 | SLC4A11 | 7.38 | 166 | Q8NBS3 | 891 | Anion exchanger (TC 2.A.31) family |
| 1306 | SLC5A2 | 7.46 | 176 | P31639 | 672 | Sodium:solute symporter (SSF) (TC 2.A.21) family |
| 1307 | SLC9A7 | 7.33 | 160.5 | Q96T83 | 725 | Monovalent cation:proton antiporter 1 (CPA1) transporter (TC 2.A.36) family |
| 1308 | SLC9A9 | 7.31 | 158.5 | Q8IVB4 | 645 | Monovalent cation:proton antiporter 1 (CPA1) transporter (TC 2.A.36) family |
| 1309 | Gamma-glutamyltransferase 4 (heavy chain; Cleaved-Thr472) | 7.35 | 163 | Q9UJ14 | 662 | Gamma-glutamyltransferase family |
| 1310 | ITGAV (heavy chain, Cleaved-Lys889) | 7.25 | 152.5 | P06756 | 1048 | Integrin alpha chain family |
| 1311 | Kallikrein-11 (Cleaved-Ile54) | 7.27 | 154.5 | Q9UBX7 | 282 | Peptidase S1 family, Kallikrein subfamily |
| 1312 | PPGB (32k, Cleaved-Arg326) | 7.17 | 144 | P10619 | 480 | Peptidase S10 family |
| 1313 | MMP17(Cleaved-Gln129) | 7.16 | 143 | Q9ULZ9 | 603 | Peptidase M10A family |
| 1314 | Neuropsin (Cleaved-Val33) | 7.45 | 175 | O60259 | 260 | Peptidase S1 family, Kallikrein subfamily |
| 1315 | Notch 2 (Cleaved-Ala1734) | 7.2 | 147.5 | Q04721 | 2471 | NOTCH family |
| 1316 | Notch 2 (Cleaved-Val1697) | 7.18 | 145.5 | Q04721 | 2471 | NOTCH family |
| 1317 | PARP (Cleaved-Gly215) | 7.55 | 187.5 | P09874 | 1014 | — |
| 1318 | KLKB1 (heavy chain, Cleaved-Arg390) | 7.55 | 188 | P03952 | 638 | Peptidase S1 family, Plasma kallikrein subfamily |
| 1319 | PAR4 (Cleaved-Gly48) | 7.51 | 182.5 | Q96RI0 | 385 | G-protein coupled receptor 1 family |
| 1320 | THRB (AP2, Cleaved-Arg327) | 7.49 | 180 | P00734 | 622 | Peptidase S1 family |
| 1321 | MAP3K6 | 7.2 | 147 | O95382 | 1288 | Protein kinase superfamily, STE Ser/Thr protein kinase family, MAP kinase kinase kinase subfamily |
| 1322 | MAP3K9 | 7.66 | 202.5 | P80192 | 1104 | Protein kinase superfamily, STE Ser/Thr protein kinase family, MAP kinase kinase kinase subfamily |
| 1323 | MAP3K10 | 7.29 | 156 | Q02779 | 954 | Protein kinase superfamily, STE Ser/Thr protein kinase family, MAP kinase kinase kinase subfamily |
| 1324 | MAP3K1 | 7.29 | 156 | Q13233 | 1512 | Protein kinase superfamily, STE Ser/Thr protein kinase family, MAP kinase kinase kinase subfamily |
| 1325 | MAP3K4 | 7.22 | 149 | Q9Y6R4 | 1608 | Protein kinase superfamily, STE Ser/Thr protein kinase family, MAP kinase kinase kinase subfamily |
| 1326 | FADD | 7.58 | 192 | Q13158 | 208 | — |
| 1327 | Lys-acetylated proteins | 7.6 | 193.5 | N/A | — | — |
| 1328 | CD69 | 7.11 | 138 | Q07108 | 199 | — |
| 1329 | CDC25C | 7.13 | 140 | P30307 | 473 | MPI phosphatase family |
| 1330 | CSF2 (GM-CSF) | 7.22 | 149 | P04141 | 144 | GM-CSF family |
| 1331 | PTH (Parathyroid Hormone) | 7.25 | 152.5 | P01270 | 115 | Parathyroid hormone family |
| 1332 | NKX3A | 7.25 | 152.5 | Q99801 | 234 | NK-3 homeobox family |
| 1333 | EGR1 | 7.2 | 147 | P18146 | 543 | EGR C2H2-type zinc-finger protein family |
| 1334 | ICAM1 | 7.22 | 149.5 | P05362 | 532 | Immunoglobulin superfamily, ICAM family |
| 1335 | CD3E | 7.23 | 150 | P07766 | 207 | — |
| 1336 | SNAI2 (SLUG) | 7.29 | 156.5 | O43623 | 268 | Snail C2H2-type zinc-finger protein family |
| 1337 | JAK2 | 7.26 | 153.5 | O60674 | 1132 | Protein kinase superfamily, Tyr protein kinase family, JAK subfamily |
| 1338 | BMX (ETK) | 7.26 | 153.5 | P51813 | 675 | Protein kinase superfamily, Tyr protein kinase family, TEC subfamily |
| 1339 | VCAM1 | 7.11 | 138.5 | P19320 | 739 | — |
| 1340 | MUM1 | 7.39 | 167.5 | Q2TAK8 | 710 | MUM1 family |
| 1341 | EPCAM | 7.24 | 151 | P16422 | 314 | EPCAM family |
| 1342 | FAK | 7.33 | 160.5 | Q05397 | 1052 | Protein kinase superfamily, Tyr protein kinase family, FAK subfamily |
| 1343 | A1BG | 7.26 | 153.5 | P04217 | 495 | — |
| 1344 | ERN1 (IRE1) | 7.33 | 160.5 | O75460 | 977 | Protein kinase superfamily, Ser/Thr protein kinase family |
| 1345 | GATA1 | 7.38 | 167 | P15976 | 413 | — |
| 1346 | FABP4 | 7.31 | 158.5 | P15090 | 132 | Calycin superfamily, Fatty-acid binding protein (FABP) family |
| 1347 | NF-kB p65 | 7.21 | 148.5 | Q04206 | 551 | — |
| 1348 | GSK3 beta | 7.23 | 150.5 | P49841 | 420 | Protein kinase superfamily, CMGC Ser/Thr protein kinase family, GSK-3 subfamily |

TABLE 2-continued

| ID | Antibody Name | Normalized data (log2) | Raw data | SwissProt | Length | Protein family |
|---|---|---|---|---|---|---|
| 1349 | Androgen receptor | 7.13 | 140 | P10275 | 919 | Nuclear hormone receptor family, NR3 subfamily |
| 1350 | Flt-1 (VEGFR1) | 7.4 | 169 | P17948 | 1338 | Protein kinase superfamily, Tyr protein kinase family, CSF-1/PDGF receptor subfamily |
| 1351 | FGF-1 | 7.06 | 133 | P05230 | 155 | Heparin-binding growth factors family |
| 1352 | FGF-2 | 7.11 | 138 | P09038 | 288 | Heparin-binding growth factors family |
| 1353 | IL-1 alpha | 7.08 | 135.5 | P01583 | 271 | IL-1 family |
| 1354 | IL-1 beta | 7.29 | 157 | P01584 | 269 | IL-1 family |
| 1355 | Angiopoietin-1 | 7.09 | 136 | Q15389 | 498 | — |
| 1356 | Angiopoietin-2 | 7.27 | 154.5 | O15123 | 496 | — |
| 1357 | CD154 (sCD40-Ligand) | 7.18 | 145.5 | P29965 | 261 | Tumor necrosis factor family |
| 1358 | CA125 | 6.98 | 126.5 | Q8WXI7 | 22152 | — |

As shown in the above Table 2, according to the mass production method of the mesenchymal stem cell-derived protein of the present invention, proteins containing a variety of growth factors and cytokines which have been known to be not or a little produced in conventional mesenchymal stem cells was confirmed to have been mass produced.

Example 7. Quantitative Comparison Using Growth Factor Array of Growth Factors Contained in Stem Cell Conditioned Medium Obtained Under Optimum Culture and Storage Conditions Proteins produced in the culture and storage conditions of mesenchymal stem cells established through the above Examples 1 to Examples 5 were quantitatively analyzed.

Specifically, in human amniotic fluid-derived stem cell conditioned medium obtained under previously known serum-free culture conditions and cryopreservation conditions and human amniotic fluid-derived stem cell conditioned medium obtained under optimal serum-free culture conditions and cryopreservation conditions established through the present invention, both contents of growth factors present were investigated by the microarray quantitative method and compared.

The existing conditioned medium means the mixed conditioned medium cultured in serum-free medium and collected at 72 hours, 144 hours, and 216 hours, respectively, after inoculating mesenchymal stem cells stored together with 10% DMSO+20% FBS+70% cDMEM mixed medium in −196° C. liquid nitrogen tank, at a density of 10,000 cells/cm² in a culture vessel, and the new conditioned medium means the mixed conditioned medium cultured in serum-free medium and collected at 120 hours, 240 hours, and 360 hours, respectively, after inoculating mesenchymal stem cells stored together with CRYO-GOLD solution in −80° C. deep freezer, at a density of 20,000 cells/cm² in a culture vessel.

Also, Raybiotech Quantibody Human Growth Factor Array 1 (Cat. #QAH-GF-1) was used as the above microarray. Specific experimental methods are as follows.

First, the slide glass was taken out from the Quantibody Human Cytokine Antibody Array Q1000 (RayBiotech, Inc.) and dried at room temperature. Next, a cytokine standard solution dilution was prepared at seven concentrations. Next, each well of the slide was added cytokine standard solution or reagent solution and placed at room temperature for 1 to 2 hours, then the added solution was removed and washed with rinsing solution for 5 times. Next, an antibody conjugate solution was added to each well in an amount of 80 μl each and incubated for 1 to 2 hours. After incubation, it was rinsed twice with a rinsing solution, and then the rinsing solution was completely removed. Next, 80 μl of streptavidin conjugated with cyanine fluorescent dye was added to each well, and the light-blocked by covering the aluminum foil or incubated under darkness for 1 hour. After inoculation, the added solution was removed and washed with rinsing solution for 5 times, and then the rinsing solution was completely removed from each well.

The above specimen was analyzed using a microarray laser scanner and the detected amounts of standard solutions were compared to calculate the cytokine content of the samples.

As a result, among the total of 56 comparative growth factors, 23 growth factors among the undetectable growth factors in the conditioned medium mixed with the stem cell conditioned medium obtained at 72, 144, and 216 hours under the serum-free culture condition in the human amniotic fluid-derived stem cells stored by the previously cryopreservation method (−196° C., 10% DMSO+20% FBS+ 70% cDMEM) at a density of 10,000 cells/cm² in a culture vessel, was confirmed to be detected in the conditioned medium mixed with the stem cell conditioned medium obtained at 120, 240, and 360 hours under the serum-free culture condition in the human amniotic fluid-derived stem cells stored by the newly established cryopreservation method (−80° C., CRYO-GOLD) at a density of 20,000 cells/cm² in a same culture vessel. Also, among the total of 56 growth factors to be compared, the content of growth factors increased from at least 51% to a maximum of 276,400% for the remaining 33 growth factors (Table 3).

TABLE 3

| number | growth factor | previous (pg/ml) | new (pg/ml) | Increasing rate (%) |
|---|---|---|---|---|
| 1 | AR | 0.0 | 104.7 | newly expressed |
| 2 | BDNF | 2.0 | 7.5 | 275 |
| 3 | bFGF | 0.0 | 84.35 | newly expressed |
| 4 | BMP-4 | 41.0 | 237.85 | 480 |
| 5 | BMP-5 | 0.0 | 983.2 | newly expressed |
| 6 | BMP-7 | 0.0 | 251.25 | newly expressed |
| 7 | b-NGF | 2.0 | 14.5 | 625 |
| 8 | EGF R | 112.0 | 1243.8 | 1011 |
| 9 | FGF-4 | 131.0 | 213.2 | 63 |
| 10 | FGF-7 | 5.0 | 407.45 | 8049 |
| 11 | GDF-15 | 1.0 | 336 | 33500 |
| 12 | GDNF | 2.0 | 50.05 | 2403 |
| 13 | GH | 0.0 | 48.9 | newly expressed |
| 14 | HGF | 7.0 | 1757.95 | 25014 |
| 15 | IGFBP-1 | 0.0 | 132.4 | newly expressed |

TABLE 3-continued

| number | growth factor | previous (pg/ml) | new (pg/ml) | Increasing rate (%) |
|---|---|---|---|---|
| 16 | IGFBP-2 | 0.0 | 54 | newly expressed |
| 17 | IGFBP-3 | 0.0 | 43691.75 | newly expressed |
| 18 | IGFBP-4 | 0.0 | 4612.25 | newly expressed |
| 19 | IGFBP-6 | 2090.0 | 40427.8 | 1834 |
| 20 | IGF-I | 85.0 | 128.2 | 51 |
| 21 | Insulin | 46.0 | 253.35 | 451 |
| 22 | MCSF R | 26.0 | 117.65 | 353 |
| 23 | NGF R | 18.0 | 46.6 | 159 |
| 24 | NT-3 | 58.0 | 104.45 | 80 |
| 25 | NT-4 | 3.0 | 16.8 | 460 |
| 26 | OPG | 6.0 | 2946.7 | 49012 |
| 27 | PDGF-AA | 32.0 | 373.9 | 1068 |
| 28 | PlGF | 6.0 | 223.25 | 3621 |
| 29 | SCF | 0.0 | 58.55 | newly expressed |
| 30 | SCF R | 156.0 | 433.75 | 178 |
| 31 | TGFa | 0.0 | 23 | newly expressed |
| 32 | TGFb1 | 0.0 | 2350.1 | newly expressed |
| 33 | VEGF | 116.0 | 4483.7 | 3765 |
| 34 | VEGF R3 | 0.0 | 37.6 | newly expressed |
| 35 | VEGF-D | 0.0 | 33.9 | newly expressed |
| 36 | G-CSF | 15 | 587 | 3913 |
| 37 | ICAM-1 | 0 | 17298 | newly expressed |
| 38 | IL-1a | 0 | 25 | newly expressed |
| 39 | IL-2 | 5 | 34 | 680 |
| 40 | IL-5 | 2 | 16 | newly expressed |
| 41 | IL-6 | 2 | 5528 | 276400 |
| 42 | IL-8 | 4 | 473 | 11825 |
| 43 | IL-11 | 323 | 14643 | 4533 |
| 44 | MCP-1 | 233 | 4256 | 1827 |
| 45 | MCSF | 589 | 1816 | 308 |
| 46 | MIG | 35 | 114 | 326 |
| 47 | MIP-1a | 0 | 7436 | newly expressed |
| 48 | MIP-1b | 0 | 193 | newly expressed |
| 49 | MIP-1d | 0 | 131 | newly expressed |
| 50 | RANTES | 0 | 141 | newly expressed |
| 51 | TIMP-1 | 87405 | 119191 | 136 |
| 52 | TIMP-2 | 102452 | 288596 | 282 |
| 53 | TNFa | 12 | 43 | 358 |
| 54 | TNFb | 26 | 95 | 365 |
| 55 | TNF R1 | 0 | 5334 | newly expressed |
| 56 | TNF RII | 0 | 658 | newly expressed |

The next, the contents of the growth factors present in the adipose-derived mesenchymal stem cell conditioned medium obtained under previously known serum-free culture conditions and cryopreservation conditions and in the adipose-derived mesenchymal stem cell conditioned medium obtained under optimal serum-free culture conditions and freezing storage conditions established through the present invention were investigated by microarray quantification method and compared.

As the measurement samples, the existing conditioned medium means the mixed conditioned medium cultured in serum-free medium and collected at 72 hours, 144 hours, and 216 hours, respectively, after inoculating adipose-derived mesenchymal stem cells stored together with 10% DMSO+20% FBS+70% cDMEM mixed medium in −196° C. liquid nitrogen tank, at a density of 10,000 cells/cm² in a culture vessel, and the new conditioned medium means the mixed conditioned medium cultured in serum-free medium and collected at 120 hours, 240 hours, and 360 hours, respectively, after inoculating adipose-derived mesenchymal stem cells stored together with CRYO-GOLD solution in −80° C. deep freezer, at a density of 20,000 cells/cm² in a culture vessel.

Also, Raybiotech Quantibody Human Growth Factor Array 1 (Cat. #QAH-GF-1) was used as the microarray. The experimental method is the same as the method performed in the above human amniotic fluid derived mesenchymal stem cells.

As a result, among the total of 18 comparative growth factors, 6 growth factors among the undetectable growth factors in the conditioned medium mixed with the stem cell conditioned medium obtained at 72, 144, and 216 hours under the serum-free culture condition in the adipose-derived mesenchymal stem cells stored by the previously cryopreservation method (−196° C., 10% DMSO+20% FBS+70% cDMEM) at a density of 10,000 cells/cm² in a culture vessel, was confirmed to be detected in the conditioned medium mixed with the stem cell conditioned medium obtained at 120, 240, and 360 hours under the serum-free culture condition in the adipose-derived mesenchymal stem cells stored by the newly established cryopreservation method (−80° C., CRYO-GOLD) at a density of 20,000 cells/cm² in a same culture vessel.

Among the total of 18 comparative growth factors, it was confirmed that the contents of growth factors increased from least 133% to a maximum of 8,833% for the remaining 12 growth factors (Table 4).

TABLE 4

| number | growth factor | previous (pg/ml) | new (pg/ml) | Increasing rate (%) |
|---|---|---|---|---|
| 1 | bFGF | 6.0 | 14.0 | 133.0 |
| 2 | EGF R | 187.0 | 606.0 | 224.0 |
| 3 | FGF-4 | 44.0 | 340.0 | 673.0 |
| 4 | FGF-7 | 0.0 | 159.0 | newly expressed |
| 5 | GDF-15 | 1.0 | 23.0 | 2,200.0 |
| 6 | HGF | 3.0 | 268.0 | 8,833.0 |
| 7 | IGFBP-1 | 0.0 | 7.0 | newly expressed |
| 8 | IGFBP-3 | 0.0 | 55224.0 | newly expressed |
| 9 | IGFBP-4 | 252.0 | 2537.0 | 907.0 |
| 10 | IGFBP-6 | 994.0 | 52997.0 | 5,232.0 |
| 11 | MCSF R | 0.0 | 54 | newly expressed |
| 12 | NT-3 | 11.0 | 55.0 | 400.0 |
| 13 | NT-4 | 0.0 | 18.0 | newly expressed |
| 14 | OPG | 134.0 | 1855.0 | 1,284.0 |
| 15 | PDGF-AA | 7.0 | 253.0 | 3,514.0 |
| 16 | PlGF | 2.0 | 55.0 | 2,650.0 |
| 17 | TGFb1 | 0.0 | 553.0 | newly expressed |
| 18 | VEGF | 591.0 | 4546.0 | 669.0 |

As a result, the mass production method of the mesenchymal stem cell-derived proteins established in the present invention was confirmed to have the effect of increasing the contents of the protein secreted from the mesenchymal stem cell or secreting the new proteins as compared with the conventional method.

Example 8. Absolute Quantitation of Collagen Content in Stem Cell Conditioned Medium Obtained Under Optimal Serum-Free Culture and Storage Conditions Since collagen is well known to play an important role in skin regeneration and wrinkle improvement, the contents of collagen contained in the mesenchymal stem cell conditioned medium obtained under the previously known serum-free culture and storage conditions and the mesenchymal stem cell conditioned medium obtained under the optimum serum-free culture and storage conditions established through the present invention were investigated by an absolute quantitative method and compared.

The existing conditioned medium means the mixed conditioned medium cultured in serum-free medium and collected at 72 hours, 144 hours, and 216 hours, respectively, after inoculating mesenchymal stem cells stored together with 10% DMSO+20% FBS+70% cDMEM mixed medium in −196° C. liquid nitrogen tank, at a density of 10,000 cells/cm² in a culture vessel, and the new conditioned medium means the mixed conditioned medium cultured in serum-free medium and collected at 120 hours, 240 hours, and 360 hours, respectively, after inoculating mesenchymal stem cells stored together with CRYO-GOLD solution in −80° C. deep freezer, at a density of 20,000 cells/cm² in a culture vessel.

Specific experimental methods are as follows.

Protein of the sample solution was quantitated using the BCA quantification method, 100 μg of which was taken and freeze-drying was carried out. The dried sample was added to 25 μg of 6 M urea and dissolved, and then the reaction was carried out at 90° C. for 20 minutes. 25 μl of 0.2 M ammonium bicarbonate solution dissolved in 10 mM ethylenediaminetetraacetic acid, 4% sodium dodecylsulfate, and 6 M urea buffer solution was added and reacted at 37° C. for 30 minutes, then acylamide/bisacylamide (40% v/v 29:1) was used the gel was solidified in the sample. The remaining washing was carried out while germ containing the sample was repeatedly exchanged for 1 day by adding 1 ml of distilled water. 50% acetonitrile and 50 mM ammonium bicarbonate were sequentially added to 1 ml, and the remaining washing was carried out while replacing them each for 1 day each.

Next, the dried sample was dissolved in 100 μl of 50 mM sodium phosphate, pH 7.3, and 5 μl of 1 M dithiothreitol was added and mixed well, and the reaction was carried out at 55° C. for 30 minutes.

Next, after adding 5 μl of 1 M iodoacetamide to the sample which completed the disulfide bond reduction reaction, the carbamido methylation reaction progressed for 30 minutes in a light-shielded state at room temperature and was completely dried.

Next, the dried sample was thoroughly mixed with 100 μl of 100 mM ammonium bicarbonate solution, then 2 μl of trypsin (1 mg/me) was added and the reaction was carried out at 37° C. for about 18 hours. Next, 200 μl of 50 mM ammonium bicarbonate solution, 200 μl of 0.1% (v/v) trifluoroacetic acid, 100 μl of 0.1% trifluoroacetic acid dissolved in acetonitrile, and 100 μl of acetonitrile solution were extracted for 1 hour each. The extracted sample was frozen and then thoroughly dried and then reacted at 80° C. for 30 minutes to decompose ammonium bicarbonate.

Next, the above sample was taken and placed in a column of Oasis SPE (Waters Co.), desalted by using vacuum and completely dried.

Next, a standard protein peptide solution was prepared by dissolving the standard protein peptide in 1 ml (400 nM) of 0.1% formic acid. Next, to the sample subjected to trypsin hydrolysis, 2 μl of the above standard protein peptide protein solution (final concentration 10 nM) was added, and then 98 μl of 0.1% formic acid was further added to prepare a final volume of 100 μl, followed by mass spectrometry was carried out. The conditions at this time are as follows.

<NANO UPLC Operation Condition>
Column:
  nanoAcquity BEH 300 C18, 1.7 μm×150 mm
  temperature: 40° C.
Mobile phase:
  mobile phase A: 0.1% v/v formic acid
  mobile phase B: 0.1% v/v formic acid, acetonitrile

TABLE 5

|   | time (min) | A(% v/v) | B(% v/v) |
|---|---|---|---|
| 1 | initial | 97.0 | 3.0 |
| 2 | 5 | 97.0 | 3.0 |
| 3 | 300 | 65.0 | 35.0 |

TABLE 5-continued

|   | time (min) | A(% v/v) | B(% v/v) |
|---|---|---|---|
| 4 | 320 | 20.0 | 80.0 |
| 5 | 340 | 20.0 | 80.0 |
| 6 | 355 | 97.0 | 3.0 |
| 7 | 360 | 97.0 | 3.0 | velocity: 300 nL/min
injection amount: 3 μl
<Mass Spectrometry Operation Condition>
Equipment: Synapt G2-Si HDMS (Waters, UK)
Source: NanoLockSpray Exact Mass ionization source
  Positive
Mass spectrometry setting condition
  capillary (kV): 3.0
  Voltage (V): 30
  Temperature (° C.): 120
  Scanning time (sec): 0.5

Protein identification and absolute quantification were carried out using ProteinLynx Global Server (PLGS) Ver 3.0 for the results obtained through the above mass spectrometry. Protein identification was performed using the Human Database (Ver. 3.87) of International Protein Index, and absolute quantification was performed based on the mass value information of standard BSA (SwissProt P2769).

As a result of assaying for a total of 30 μg protein samples, it was confirmed that the stem cell conditioned medium obtained under the optimum serum-free culture and storage conditions of the present invention increased the collagen content about 230% as compared with the conventional conditioned medium (Table 6).

TABLE 6

|   | Existing | New |
|---|---|---|
| Total detected protein (μg) | 21.94 | 25.12 |
| Total detected collagen (μg) | 1.18 | 3.12 |
| collagen content (%) | 5.42 | 12.4 |

Example 9. Comparison of Collagen Synthesis Effect of Stem Cell Conditioned Medium Obtained Under Optimal Serum-Free Culture and Storage Conditions Intracellular collagen production test of mesenchymal stem cell conditioned medium obtained under the optimum serum-free culture and storage conditions established through the present invention was performed using human fibroblast cell (CCD 98sk).

As a result of performing the sample concentration setting preliminary test in order to set the concentration of the sample solution for the intracellular collagen production test, it was confirmed that cytotoxicity was not induced when the concentration of the sample solution was 0 to 0.5%. Among them, the maximum concentration of 0.5% was set to the concentration of the sample solution for intracellular collagen production test. And as the positive control substance, 0.04% of adenosine which is the notification content of adenosine which is the raw material for wrinkle amelioration functional announcement by KFDA was used.

As a result of intracellular collagen production test, it was confirmed that the collagen production is promoted 13 times or more as compared with positive control group (0.04% of Adenosine)(FIG. 7).

Accordingly, the mesenchymal stem cell conditioned medium of the present invention not only contains a large amount of collagen but also has the efficacy of inducing collagen production of fibroblasts, therefore it is possible to know that it is effective for skin regeneration and wrinkle improvement.

Example 10. Comparison of the Efficacy of Wound Healing of the Stem Cell Conditioned Medium Obtained Under Optimal Serum-Free Culture and Storage Conditions The wound healing effects of the mesenchymal stem cell conditioned medium obtained under the previously known serum-free culture and storage conditions and the mesenchymal stem cell conditioned medium obtained under the optimum serum-free culture and storage conditions established through the present invention were investigated and compared.

The existing conditioned medium means the mixed conditioned medium cultured in serum-free medium and collected at 72 hours, 144 hours, and 216 hours, respectively, after inoculating mesenchymal stem cells stored together with 10% DMSO+20% FBS+70% cDMEM mixed medium in −196° C. liquid nitrogen tank, at a density of 10,000 cells/cm$^2$ in a culture vessel, and the new conditioned medium means the mixed conditioned medium cultured in serum-free medium and collected at 120 hours, 240 hours, and 360 hours, respectively, after inoculating mesenchymal stem cells stored together with CRYO-GOLD solution in −80° C. deep freezer, at a density of 20,000 cells/cm$^2$ in a culture vessel. Human Fibroblast were inoculated with 7.5× 10$^5$ cells in a culture vessel, and take photos of wound distances to measure after make wound on the cells using the microchip, and immediately add 3 ml of the existing conditioned medium and the new conditioned medium on each wound, and take photos again after 12 hours to measure the wound distances.

As a result, the stem cell conditioned medium obtained under optimum serum-free culture and storage conditions of the present invention showed the wound healing effect which was about 79% higher than that of the conventional conditioned medium (FIG. 8).

Example 11. Comparison of the Growth Promoting Effect of the Stem Cell Conditioned Medium Obtained Under Optimal Serum-Free Culture and Storage Conditions Using the Hair Growth Suppression Model A comparative test was performed to examine the hair growth effect of the mesenchymal stem cell conditioned medium of the present invention using C57BL/6 mice.

After depilating the test animals, the depilatory was treated to induce them from the telogen (resting phase) to the anagen (growing phase), and then to suppress the growth of hair follicles, 0.1% of dexamethanone was transdermally administered for 5 days from 8 days after depilation repeatedly. Next, in order to compare the growth promoting effect of the test substance containing 3% of the mesenchymal stem cell conditioned medium of the present invention, the growth promoting effects were compared with the test substance by transdermally administered repeatedly of G1 (distilled water control), G2 (placebo control), G3 (test substance) and G4 (positive control-minoxidil 5%) for 8 days.

As a result of visual observation for hair growth (Table 7 and FIGS. 9 to 12), the hair color began to change to gray from the 4 day of administration of the test substance, and as a result of scoring the degree of hair growth on the 8th day of administration, G1: 1.70 points, G2: 1.45 points, G3: 3.50 points, G4: 2.68 points were observed. In conclusion, it was confirmed that the test substance administration group statistically significantly increased hair growth compared with the control group and the Placebo control group (p<0.01).

TABLE 7

Visual observation for hair growth of mouse hair growth score (gender: female)

| Group | Animal ID | Score 1st | 2nd | 3rd | 4th | Average | S.D | Total Average | Total S.D |
|---|---|---|---|---|---|---|---|---|---|
| G1 | 0101 | 2 | 2 | 3 | 4 | 2.75 | 0.96 | 1.70 | 1.01 |
|  | 0102 | 1 | 1 | 1 | 2 | 1.25 | 0.50 |  |  |
|  | 0103 | 1 | 2 | 2 | 3 | 2.00 | 0.82 |  |  |
|  | 0104 | 1 | 1 | 0 | 2 | 1.00 | 0.82 |  |  |
|  | 0105 | 3 | 3 | 2 | 4 | 3.00 | 0.82 |  |  |
|  | 0106 | 1 | 2 | 1 | 3 | 1.75 | 0.96 |  |  |
|  | 0107 | 0 | 0 | 0 | 0 | 0.00 | 0.00 |  |  |
|  | 0108 | 3 | 3 | 2 | 4 | 3.00 | 0.82 |  |  |
|  | 0109 | 1 | 1 | 1 | 3 | 1.50 | 1.00 |  |  |
|  | 0110 | 0 | 1 | 0 | 2 | 0.75 | 0.96 |  |  |
| G2 | 0201 | 0 | 1 | 0 | 1 | 0.50 | 0.58 | 1.45 | 1.13 |
|  | 0202 | 0 | 1 | 0 | 1 | 0.50 | 0.58 |  |  |
|  | 0203 | 2 | 1 | 2 | 2 | 1.75 | 0.50 |  |  |
|  | 0204 | 2 | 2 | 2 | 3 | 2.25 | 0.50 |  |  |
|  | 0205 | 2 | 1 | 1 | 3 | 1.75 | 0.96 |  |  |
|  | 0206 | 0 | 0 | 0 | 0 | 0.00 | 0.00 |  |  |
|  | 0207 | 4 | 2 | 3 | 4 | 3.25 | 0.96 |  |  |
|  | 0208 | 4 | 2 | 2 | 4 | 3.00 | 1.15 |  |  |
|  | 0209 | 0 | 0 | 0 | 2 | 0.50 | 1.00 |  |  |
|  | 0210 | 1 | 0 | 0 | 3 | 1.00 | 1.41 |  |  |
| G3 | 0301 | 4 | 4 | 4 | 4 | 4.00 | 0.00 | 3.50**/## | 0.37 |
|  | 0302 | 3 | 2 | 4 | 4 | 3.25 | 0.96 |  |  |
|  | 0303 | 3 | 2 | 4 | 4 | 3.25 | 0.96 |  |  |
|  | 0304 | 4 | 2 | 4 | 4 | 3.50 | 1.00 |  |  |
|  | 0305 | 4 | 3 | 4 | 4 | 3.75 | 0.50 |  |  |
|  | 0306 | 4 | 2 | 4 | 4 | 3.50 | 1.00 |  |  |
|  | 0307 | 3 | 2 | 4 | 3 | 3.00 | 0.82 |  |  |
|  | 0308 | 4 | 4 | 4 | 4 | 4.00 | 0.00 |  |  |
|  | 0309 | 4 | 3 | 4 | 4 | 3.75 | 0.50 |  |  |
|  | 0310 | 3 | 3 | 3 | 3 | 3.00 | 0.00 |  |  |
| G4 | 0401 | 2 | 2 | 4 | 4 | 3.00 | 1.15 | 2.68** | 0.67 |
|  | 0402 | 2 | 2 | 4 | 4 | 3.00 | 1.15 |  |  |
|  | 0403 | 2 | 2 | 4 | 4 | 3.00 | 1.15 |  |  |
|  | 0404 | 1 | 1 | 2 | 3 | 1.75 | 0.96 |  |  |
|  | 0405 | 1 | 2 | 3 | 3 | 2.25 | 0.96 |  |  |
|  | 0406 | 2 | 2 | 3 | 4 | 2.75 | 0.96 |  |  |
|  | 0407 | 3 | 2 | 2 | 4 | 2.75 | 0.96 |  |  |
|  | 0408 | 2 | 1 | 1 | 3 | 1.75 | 0.96 |  |  |
|  | 0409 | 2 | 2 | 2 | 4 | 2.50 | 1.00 |  |  |
|  | 0410 | 4 | 4 | 4 | 4 | 4.00 | 0.00 |  |  |

G1: distilled water control, G2: Placebo control, G3: test substance, G4: positive control (5% Minoxidil)
Score: 0~19% (0), 20~39% (1), 40~59% (2), 60~79% (3), 80~100% (4)
**Significant difference compared with vehicle control group value, p < 0.01
Significant difference compared with placebo group value, p < 0.01

Also, as a result of measuring the number of hair follicles by histopathological examination (Table 8, FIGS. 13 and 14), G1: 54.37, G2: 53.97, G3: 105.53, and G4: 66.37 were judged, and it showed that the test substance administration group statistically significantly increased the number of hair follicles compared with the control group and the Placebo control group (p<0.01).

TABLE 8

Result of measuring the number of hair follicles of mouse
number of hair follicles (gender: female)

| Group | Aminal ID | Measured number | | | | | Total | Total |
|---|---|---|---|---|---|---|---|---|
| | | Area 1 | Area 2 | Area 3 | Average | S.D. | Average | S.D. |
| G1 | 0101 | 73 | 22 | 37 | 44.00 | 26.21 | 54.37 | 23.48 |
| | 0102 | 47 | 33 | 0 | 26.67 | 24.13 | | |
| | 0103 | 61 | 74 | 82 | 72.33 | 10.60 | | |
| | 0104 | 28 | 55 | 37 | 40.00 | 13.75 | | |
| | 0105 | 66 | 98 | 89 | 84.33 | 16.50 | | |
| | 0106 | 60 | 84 | 113 | 85.67 | 26.54 | | |
| | 0107 | 16 | 4 | 19 | 13.00 | 7.94 | | |
| | 0108 | 47 | 62 | 58 | 55.67 | 7.77 | | |
| | 0109 | 82 | 70 | 75 | 75.67 | 60.3 | | |
| | 0110 | 45 | 51 | 43 | 46.33 | 4.16 | | |
| G2 | 0201 | 1 | 13 | 13 | 9.00 | 6.93 | 53.87 | 40.05 |
| | 0202 | 35 | 27 | 30 | 30.67 | 4.04 | | |
| | 0203 | 87 | 67 | 63 | 72.33 | 12.86 | | |
| | 0204 | 88 | 72 | 36 | 65.33 | 26.63 | | |
| | 0205 | 85 | 108 | 77 | 90.00 | 16.09 | | |
| | 0206 | 18 | 13 | 5 | 12.00 | 6.56 | | |
| | 0207 | 124 | 110 | 106 | 113.33 | 9.45 | | |
| | 0208 | 140 | 127 | 74 | 113.67 | 34.96 | | |
| | 0209 | 28 | 9 | 8 | 15.00 | 11.27 | | |
| | 0210 | 13 | 24 | 15 | 17.33 | 5.86 | | |
| G3 | 0301 | 138 | 136 | 135 | 136.33 | 1.53 | 105.33**/## | 15.52 |
| | 0302 | 81 | 120 | 99 | 100.00 | 19.52 | | |
| | 0303 | 86 | 92 | 115 | 97.67 | 15.31 | | |
| | 0304 | 95 | 117 | 103 | 105.00 | 11.14 | | |
| | 0305 | 112 | 100 | 109 | 107.00 | 6.24 | | |
| | 0306 | 124 | 112 | 126 | 120.67 | 7.57 | | |
| | 0307 | 91 | 85 | 88 | 88.00 | 3.00 | | |
| | 0308 | 156 | 72 | 84 | 104.00 | 45.43 | | |
| | 0309 | 92 | 87 | 59 | 79.33 | 17.79 | | |
| | 0310 | 110 | 124 | 118 | 117.33 | 7.02 | | |
| G4 | 0401 | 70 | 96 | 97 | 87.67 | 15.31 | 66.37 | 27.22 |
| | 0402 | 97 | 87 | 93 | 92.33 | 5.03 | | |
| | 0403 | 66 | 65 | 82 | 71.00 | 9.54 | | |
| | 0404 | 53 | 37 | 19 | 36.33 | 17.01 | | |
| | 0405 | 114 | 108 | 103 | 108.33 | 5.51 | | |
| | 0406 | 65 | 52 | 67 | 61.33 | 8.14 | | |
| | 0407 | 78 | 37 | 21 | 45.33 | 29.40 | | |
| | 0408 | 46 | 19 | 24 | 29.67 | 14.36 | | |
| | 0409 | 37 | 48 | 23 | 36.00 | 12.53 | | |
| | 0410 | 95 | 87 | 105 | 95.67 | 9.02 | | |

G1: distilled water control, G2: Placebo control, G3: test substance, G4: positive control (5% Minoxidil)
**Significant difference compared with vehicle control group value, $p < 0.01$
Significant difference compared with placebo group value, $p < 0.01$ According to the above results, in this test condition, induction of growth inhibition by administering 0.1% of dexamethasone to the anagen hair C57BL/6 mice model for 5 days, at the same time the test substance containing the human mesenchymal stem cell conditioned medium established through the present invention, as a result of repeated transdermal administration for 8 days, it was confirmed that the hair growth promotion effect was remarkably superior to that of the Minoxidil as a positive control group.

Example 12. Comparison of Growth Promoting Effect of the Stem Cell Conditioned Medium Obtained Under Optimal Serum-Free Culture and Storage Conditions in the Anagen Hair Model A comparative test was performed to investigate the effect of hair growth promotion of the mesenchymal stem cell conditioned medium of the present invention using C57BL/6 mice.

After induction of the hair follicles of the test animal from the telogen (resting phase) to the anagel (growing phase) and depilatione, in order to compare the growth promoting effect of the test substance containing 3% of the mesenchymal stem cell conditioned medium of the present invention, G1 (distilled water control), G2 (placebo control), G3 (test substance) and G4 (positive control-minoxidil 5%) were transdermally administered repeatedly for 14 days respectively, and the hair growth promoting effects were compared with the test substance.

As a result of visual observation of hair growth (Table 9, Table 10, and FIGS. 15 to 17), on the 13th day, the degree of hair growth was scored as G1: 1.47 point, G2: 1.33 point, G3: 2.53 point, G4: 3.27 point. On the 15th day, the degree of hair growth was scored as G1: 3.05 point, G2: 2.80 point, G3: 3.60 point, G4: 3.78 point. According to the test result, it was confirmed that the test substance administration group on the 13th and 15th day was statistically significantly increased compared to the Placebo control group ($p<0.01$).

TABLE 9

Gross observation of hair growth of mouse (13th day) hair growth score (gender: female)

| Group | Animal ID | Score 1st | 2nd | 3rd | 4th | Average | S.D. | Total Average | Total S.D. |
|---|---|---|---|---|---|---|---|---|---|
| G1 | 0101 | 0 | 0 | 0 | 2 | 0.67 | 1.00 | 1.47 | 1.00 |
|  | 0102 | 3 | 2 | 3 | 3 | 2.67 | 0.50 |  |  |
|  | 0103 | 0 | 0 | 0 | 2 | 0.67 | 1.00 |  |  |
|  | 0104 | 3 | 3 | 3 | 4 | 3.33 | 0.50 |  |  |
|  | 0105 | 1 | 0 | 1 | 3 | 1.33 | 1.26 |  |  |
|  | 0106 | 1 | 0 | 1 | 3 | 1.33 | 1.26 |  |  |
|  | 0107 | 1 | 0 | 0 | 2 | 0.67 | 0.96 |  |  |
|  | 0108 | 0 | 0 | 0 | 1 | 0.33 | 0.50 |  |  |
|  | 0109 | 3 | 2 | 2 | 3 | 2.33 | 0.58 |  |  |
|  | 0110 | 2 | 0 | 1 | 3 | 1.33 | 1.29 |  |  |
| G2 | 0201 | 2 | 1 | 3 | 4 | 2.67 | 1.29 | 1.33 | 0.92 |
|  | 0202 | 3 | 2 | 3 | 4 | 3.00 | 0.82 |  |  |
|  | 0203 | 1 | 0 | 1 | 3 | 1.33 | 1.26 |  |  |
|  | 0204 | 0 | 0 | 0 | 3 | 1.00 | 1.50 |  |  |
|  | 0205 | 0 | 0 | 0 | 2 | 0.67 | 1.00 |  |  |
|  | 0206 | 1 | 0 | 0 | 3 | 1.00 | 1.41 |  |  |
|  | 0207 | 2 | 1 | 2 | 3 | 2.00 | 0.82 |  |  |
|  | 0208 | 0 | 0 | 0 | 1 | 0.33 | 0.50 |  |  |
|  | 0209 | 0 | 0 | 0 | 2 | 0.67 | 1.00 |  |  |
|  | 0210 | 0 | 0 | 0 | 2 | 0.67 | 1.00 |  |  |
| G3 | 0301 | 3 | 3 | 4 | 4 | 3.67 | 0.58 | 2.53**/## | 0.98 |
|  | 0302 | 0 | 0 | 1 | 3 | 1.33 | 1.41 |  |  |
|  | 0303 | 2 | 2 | 3 | 3 | 2.67 | 0.58 |  |  |
|  | 0304 | 1 | 1 | 2 | 3 | 2.00 | 0.96 |  |  |
|  | 0305 | 2 | 1 | 3 | 4 | 2.67 | 1.29 |  |  |
|  | 0306 | 4 | 4 | 4 | 4 | 4.00 | 0.00 |  |  |
|  | 0307 | 4 | 4 | 3 | 4 | 3.67 | 0.50 |  |  |
|  | 0308 | 2 | 1 | 3 | 3 | 2.33 | 0.96 |  |  |
|  | 0309 | 1 | 1 | 1 | 3 | 1.67 | 1.00 |  |  |
|  | 0310 | 1 | 0 | 1 | 3 | 1.33 | 1.26 |  |  |
| G4 | 0401 | 3 | 3 | 4 | 4 | 3.67 | 0.58 | 3.27** | 0.58 |
|  | 0402 | 4 | 4 | 4 | 4 | 4.00 | 0.00 |  |  |
|  | 0403 | 2 | 3 | 4 | 3 | 3.33 | 0.82 |  |  |
|  | 0404 | 3 | 3 | 4 | 4 | 3.67 | 0.58 |  |  |
|  | 0405 | 2 | 3 | 3 | 3 | 3.00 | 0.50 |  |  |
|  | 0406 | 3 | 3 | 3 | 4 | 3.33 | 0.50 |  |  |
|  | 0407 | 4 | 4 | 4 | 4 | 4.00 | 0.00 |  |  |
|  | 0408 | 3 | 1 | 3 | 3 | 2.33 | 1.00 |  |  |
|  | 0409 | 2 | 2 | 3 | 3 | 2.67 | 0.58 |  |  |
|  | 0410 | 2 | 1 | 4 | 3 | 2.67 | 1.29 |  |  |

G1: distilled water control, G2: Placebo control, G3: test substance, G4: positive control (5% Minoxidil)
Score: 0~19% (0), 20~39% (1), 40~59% (2), 60~79% (3), 80~100% (4)
**Significant difference compared with vehicle control group value, $p < 0.01$
Significant difference compared with placebo group value, $p < 0.01$

TABLE 10

Gross observation of hair growth of mouse (15th day) hair growth score (gender: female)

| Group | Animal ID | Score 1st | 2nd | 3rd | 4th | Average | S.D. | Total Average | Total S.D. |
|---|---|---|---|---|---|---|---|---|---|
| G1 | 0101 | 1 | 1 | 3 | 3 | 2 | 1.15 | 3.05 | 1.07 |
|  | 0102 | 4 | 4 | 4 | 4 | 4 | 0.00 |  |  |
|  | 0103 | 1 | 1 | 3 | 2 | 1.75 | 0.96 |  |  |
|  | 0104 | 4 | 4 | 4 | 4 | 4 | 0.00 |  |  |
|  | 0105 | 2 | 2 | 3 | 3 | 2.5 | 0.58 |  |  |
|  | 0106 | 4 | 4 | 4 | 4 | 4 | 0.00 |  |  |
|  | 0107 | 3 | 3 | 4 | 4 | 3.5 | 0.58 |  |  |
|  | 0108 | 1 | 1 | 1 | 2 | 1.25 | 0.50 |  |  |
|  | 0109 | 4 | 4 | 4 | 4 | 4 | 0.00 |  |  |
|  | 0110 | 4 | 3 | 4 | 3 | 3.5 | 0.58 |  |  |
| G2 | 0201 | 4 | 3 | 4 | 4 | 3.75 | 0.50 | 2.80 | 0.90 |
|  | 0202 | 4 | 4 | 4 | 4 | 4 | 0.00 |  |  |
|  | 0203 | 2 | 2 | 4 | 3 | 2.75 | 0.96 |  |  |
|  | 0204 | 1 | 1 | 3 | 2 | 1.75 | 0.96 |  |  |
|  | 0205 | 1 | 1 | 2 | 2 | 1.5 | 0.58 |  |  |
|  | 0206 | 2 | 2 | 3 | 4 | 2.75 | 0.96 |  |  |
|  | 0207 | 4 | 4 | 4 | 4 | 4 | 0.00 |  |  |
|  | 0208 | 1 | 1 | 3 | 3 | 2 | 1.15 |  |  |
|  | 0209 | 2 | 2 | 4 | 3 | 2.75 | 0.96 |  |  |
|  | 0210 | 2 | 2 | 4 | 3 | 2.75 | 0.96 |  |  |
| G3 | 0301 | 4 | 4 | 4 | 4 | 4 | 0.00 | 3.60**/## | 0.46 |
|  | 0302 | 2 | 3 | 3 | 3 | 2.75 | 0.50 |  |  |
|  | 0303 | 4 | 4 | 4 | 4 | 4 | 0.00 |  |  |
|  | 0304 | 4 | 4 | 4 | 4 | 4 | 0.00 |  |  |
|  | 0305 | 4 | 3 | 4 | 4 | 3.75 | 0.50 |  |  |
|  | 0306 | 4 | 3 | 4 | 4 | 3.75 | 0.50 |  |  |
|  | 0307 | 4 | 4 | 4 | 4 | 4 | 0.00 |  |  |
|  | 0308 | 4 | 3 | 4 | 3 | 3.5 | 0.58 |  |  |
|  | 0309 | 3 | 2 | 4 | 3 | 3 | 0.82 |  |  |
|  | 0310 | 3 | 2 | 4 | 4 | 3.25 | 0.96 |  |  |
| G4 | 0401 | 4 | 4 | 4 | 4 | 4 | 0.00 | 3.78** | 0.22 |
|  | 0402 | 4 | 3 | 4 | 4 | 3.75 | 0.50 |  |  |
|  | 0403 | 3 | 4 | 4 | 3 | 3.5 | 0.58 |  |  |
|  | 0404 | 4 | 3 | 4 | 3 | 3.5 | 0.58 |  |  |
|  | 0405 | 4 | 3 | 4 | 4 | 3.75 | 0.50 |  |  |
|  | 0406 | 4 | 3 | 4 | 3 | 3.5 | 0.58 |  |  |
|  | 0407 | 4 | 4 | 4 | 4 | 4 | 0.00 | 4 |  |
|  | 0408 | 4 | 3 | 4 | 4 | 3.75 | 0.50 |  |  |
|  | 0409 | 4 | 4 | 4 | 4 | 4 | 0.00 |  |  |
|  | 0410 | 4 | 4 | 4 | 4 | 4 | 0.00 |  |  |

G1: distilled water control, G2: Placebo control, G3: test substance, G4: positive control (5% Minoxidil)
Score: 0~19% (0), 20~39% (1), 40~59% (2), 60~79% (3), 80~100% (4)
**Significant difference compared with vehicle control group value, $p < 0.01$
Significant difference compared with placebo group value, $p < 0.01$ Also, as a result of measuring the number of hair follicles by histopathological examination (Table 11, FIG. 18 and FIG. 19), G1: 87.80, G2: 103.57, G3: 130.63, G4: 104.70 were judged, and it showed that the test substance administration group statistically significantly increased the number of hair follicles compared with the control group and the Placebo control group ($p<0.01$).

TABLE 11

Result of measuring the number of hair follicles of mouse
number of hair follicles (gender: female)

| Group | Animal ID | Measured number | | | | | Total | Total |
|---|---|---|---|---|---|---|---|---|
| | | Area 1 | Area 2 | Area 3 | Average | S.D. | Average | S.D. |
| G1 | 0101 | 108 | 86 | 115 | 103.00 | 15.13 | 87.80 | 26.77 |
| | 0102 | 87 | 121 | 119 | 109.00 | 19.08 | | |
| | 0103 | 57 | 74 | 76 | 69.00 | 10.44 | | |
| | 0104 | 129 | 137 | 124 | 130.00 | 6.56 | | |
| | 0105 | 91 | 87 | 105 | 94.33 | 9.45 | | |
| | 0106 | 40 | 51 | 48 | 46.33 | 5.69 | | |
| | 0107 | 112 | 120 | 100 | 110.67 | 10.07 | | |
| | 0108 | 26 | 47 | 61 | 44.67 | 17.62 | | |
| | 0109 | 78 | 73 | 76 | 75.67 | 2.52 | | |
| | 0110 | 31 | 106 | 149 | 95.33 | 59.72 | | |
| G2 | 0201 | 114 | 104 | 132 | 116.67 | 14.19 | 103.57 | 23.18 |
| | 0202 | 133 | 130 | 136 | 133.00 | 3.00 | | |
| | 0203 | 132 | 130 | 154 | 138.67 | 13.32 | | |
| | 0204 | 124 | 105 | 117 | 115.33 | 9.61 | | |
| | 0205 | 111 | 79 | 137 | 109.00 | 29.05 | | |
| | 0206 | 104 | 98 | 84 | 95.33 | 10.26 | | |
| | 0207 | 113 | 98 | 107 | 106.00 | 7.55 | | |
| | 0208 | 73 | 91 | 94 | 86.00 | 11.36 | | |
| | 0209 | 66 | 71 | 64 | 67.00 | 3.61 | | |
| | 0210 | 75 | 56 | 75 | 68.67 | 10.97 | | |
| G3 | 0301 | 145 | 116 | 92 | 117.67 | 26.54 | 130.63**/## | 28.45 |
| | 0302 | 135 | 121 | 104 | 120.00 | 15.52 | | |
| | 0303 | 167 | 156 | 171 | 164.67 | 7.77 | | |
| | 0304 | 143 | 133 | 215 | 163.67 | 44.74 | | |
| | 0305 | 164 | 172 | 142 | 159.33 | 15.53 | | |
| | 0306 | 166 | 167 | 108 | 147.00 | 33.78 | | |
| | 0307 | 139 | 102 | 138 | 126.33 | 21.08 | | |
| | 0308 | 91 | 45 | 60 | 65.33 | 23.46 | | |
| | 0309 | 129 | 125 | 103 | 119.00 | 14.00 | | |
| | 0310 | 98 | 158 | 114 | 123.33 | 31.07 | | |
| G4 | 0401 | 232 | 209 | 133 | 191.33 | 51.81 | 104.70 | 44.25 |
| | 0402 | 48 | 135 | 140 | 107.67 | 51.73 | | |
| | 0403 | 92 | 55 | 60 | 69.00 | 20.07 | | |
| | 0404 | 135 | 155 | 159 | 149.67 | 12.86 | | |
| | 0405 | 45 | 50 | 69 | 54.67 | 12.66 | | |
| | 0406 | 90 | 94 | 64 | 82.67 | 16.29 | | |
| | 0407 | 71 | 79 | 67 | 72.33 | 6.11 | | |
| | 0408 | 149 | 126 | 116 | 130.33 | 16.92 | | |
| | 0409 | 121 | 164 | 131 | 138.67 | 22.50 | | |
| | 0410 | 53 | 41 | 58 | 50.67 | 8.74 | | |

G1: distilled water control, G2: Placebo control, G3: test substance, G4: positive control (5% Minoxidil)
**Significant difference compared with vehicle control group value, $p < 0.01$
Significant difference compared with placebo group value, $p < 0.01$ According to the above results of repeated transdermal administration of the test substance containing the human mesenchymal stem cell conditioned medium established through the present invention in the anagen hair C57BL/6 mice model under the present test condition for 14 days, it was confirmed that it has the excellent effect on hair growth promotion.

Example 13. Validation of Optimal Serum-Free Culture Conditions in Adipose-Derived Mesenchymal Stem Cell Culture In order to confirm that the optimal serum-free culture conditions of the present invention are applicable to other tissue-derived mesenchymal stem cells, the total protein contents present in the stem cell conditioned medium obtained by culturing the human adipose-derived mesenchymal stem cells (STEMPRO Human Adipose-Derived Stem Cells, INVITROGEN, Cat. #R7788-110) in two serum-free culture conditions were examined by BCA measurement method and compared as the same manner as in Example 5.

The existing conditioned medium means conditioned medium mixed with stem cell conditioned medium obtained at 72 hours, 144 hours, and 216 hours respectively after inoculating adipose-derived mesenchymal stem cells at a density of 10,000 cell/cm$^2$ in a culture vessel and serum-free culture, and the new conditioned medium means conditioned medium mixed with stem cell conditioned medium obtained at 120 hours, 240 hours, and 360 hours after inoculating adipose-derived mesenchymal stem cells at a density of 20,000 cell/cm$^2$ in a culture vessel and serum-free culture.

Figure 20:
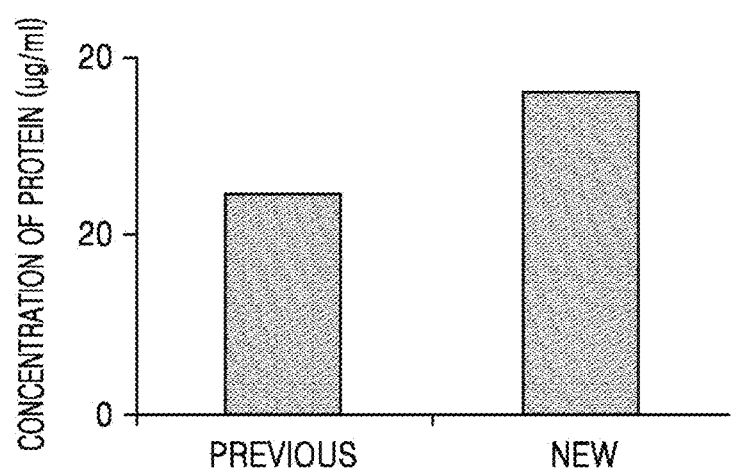
FIG. 20 is the graph showing the optimal serum-free culture conditions in the adipose-derived mesenchymal stem cell conditioned medium.

As a result, the total protein content present in the conditioned medium mixed with stem cell conditioned medium obtained at 72 hours, 144 hours, and 216 hours respectively under serum-free culture condition after inoculating human adipose-derived mesenchymal stem cells at a density of 10,000 cells in the culture vessel was 12.46 μg/ml, and the total protein content present in the conditioned medium mixed with stem cell conditioned medium obtained at 120 hours, 240 hours, and 360 hours respectively under serum-free culture condition after inoculating human adipose-derived mesenchymal stem cells at a density of 20,000 cells/cm$^2$ in the same culture vessel was 18.27 μg/ml which was 50% more improved protein content than the former (FIG. 20).

According to the above result, it could be confirmed that the optimal serum-free culture conditions that can maximize the secreted protein content from human mesenchymal stem cells established through the present invention can be applied not only human amniotic fluid-derived mesenchymal stem cells but also human adipose-derived mesenchymal stem cells.

Example 14. Validation of Optimal Serum-Free Culture Conditions in Bone Marrow-Derived Mesenchymal Stem Cell Conditioned Medium In order to confirm that the optimal serum-free culture conditions of the present invention are applicable to other tissue-derived mesenchymal stem cells, the total protein content present in the stem cell conditioned medium obtained by culturing the human bone marrow-derived mesenchymal stem cells (Human Bone Marrow-Derived Mesenchymal Stem Cell, SCIENCELL, Cat. #7500) in two serum-free culture conditions was examined by BCA measurement method and compared as the same manner as in Example 5.

The existing conditioned medium means conditioned medium mixed with stem cell conditioned medium obtained at 72 hours, 144 hours, and 216 hours respectively after inoculating bone marrow-derived mesenchymal stem cells at a density of 10,000 cell/cm$^2$ in a culture vessel and serum-free culture, and the new conditioned medium means conditioned medium mixed with stem cell conditioned medium obtained at 120 hours, 240 hours, and 360 hours respectively after inoculating bone-marrow-derived mesenchymal stem cells at a density of 20,000 cell/cm$^2$ in a culture vessel and serum-free culture.

Figure 21:
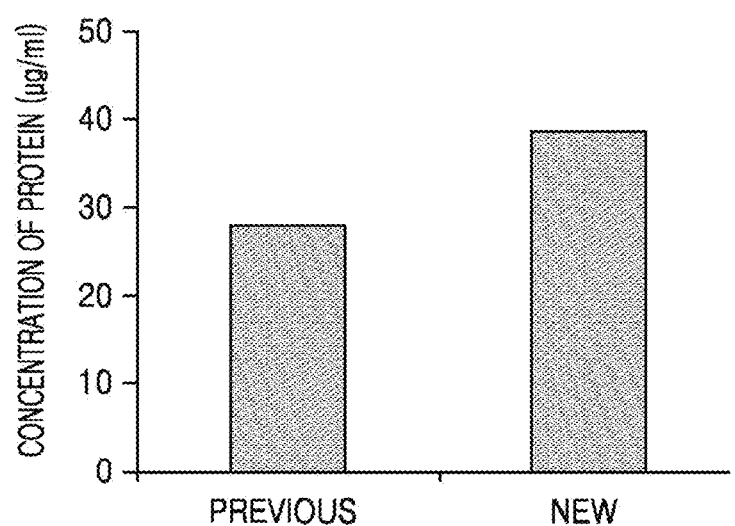
FIG. 21 is the graph showing the optimal serum-free culture conditions in the bone marrow-derived mesenchymal stem cell conditioned medium.

As a result, the total protein content present in the conditioned medium mixed with stem cell conditioned medium obtained at 72 hours, 144 hours, and 216 hours respectively under serum-free culture condition after inoculating human bone marrow-derived mesenchymal stem cells at a density of 10,000 cells in the culture vessel was 28.16 µg/ml, and the total protein content present in the conditioned medium mixed with stem cell conditioned medium obtained in each case at 120 hours, 240 hours, and 360 hours respectively under serum-free culture condition after inoculating human bone marrow-derived mesenchymal stem cells at a density of 20,000 cells/cm$^2$ in the same culture vessel was 38.78 µg/ml, which was 37% more improved protein content than the former (FIG. 21).

According to the above results, it could be confirmed that the optimal serum-free culture conditions that can maximize the secreted protein content from human mesenchymal stem cells established through the present invention can be applied not only human amniotic fluid-derived mesenchymal stem cells but also human bone marrow-derived mesenchymal stem cells.

Example 15. Validation of Optimal Serum-Free Culture Conditions in Umbilical Cord Blood Derived Mesenchymal Stem Cell Conditioned Medium In order to confirm that the optimal serum-free culture conditions of the present invention are applicable to other tissue-derived mesenchymal stem cells, the total protein contents present in the stem cell conditioned medium obtained by culturing the human umbilical cord blood derived mesenchymal stem cells (Human Umblical Mesenchymal Stem Cell, SCIENCELL, Cat. #7530) in two serum-free culture conditions was examined by BCA measurement method and compared as the same manner as in Example 5.

The existing conditioned medium means conditioned medium mixed with stem cell conditioned medium obtained at 72 hours, 144 hours, and 216 hours respectively after inoculating umbilical cord blood derived mesenchymal stem cells at a density of 10,000 cell/cm$^2$ in a culture vessel and serum-free culture, and the new conditioned medium means conditioned medium mixed with stem cell conditioned medium obtained at 120 hours, 240 hours, and 360 hours respectively after inoculating at a density of 20,000 cell/cm$^2$ in a culture vessel and serum-free culture.

Figure 22:
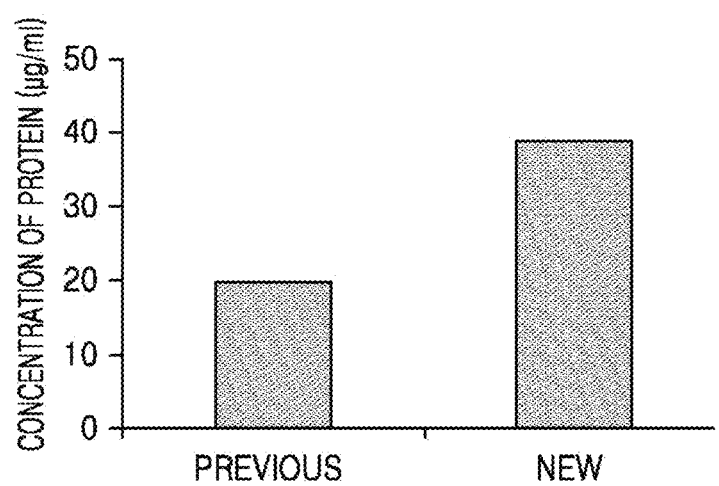
FIG. 22 is the graph showing the optimal serum-free culture conditions in the umbilical cord blood-derived mesenchymal stem cell conditioned medium.
Figure 23:
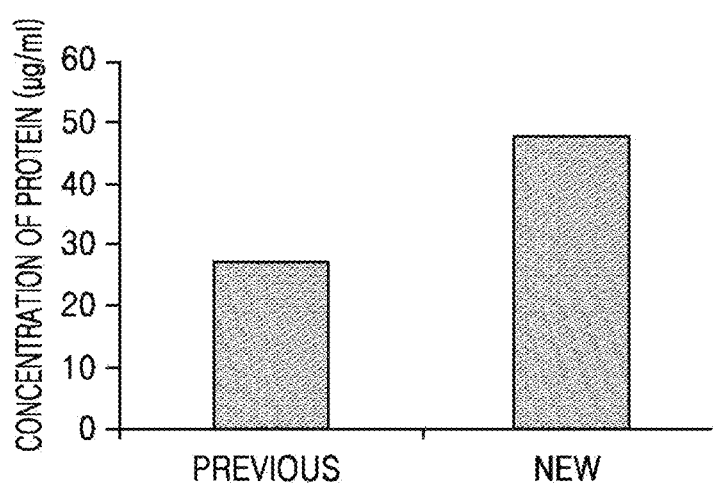
FIG. 23 is the graph showing the optimal serum-free culture conditions in the amnionic membrane-derived mesenchymal stem cell conditioned medium.

As a result, the total protein content present in the conditioned medium mixed with stem cell conditioned medium obtained in each case at 72 hours, 144 hours, and 216 hours respectively under serum-free culture condition after inoculating human umbilical cord blood derived mesenchymal stem cells at a density of 10,000 cells in the culture vessel was 20.056 µg/ml, and the total protein content present in the conditioned medium mixed with stem cell conditioned medium obtained in each case at 120 hours, 240 hours, and 360 hours respectively under serum-free culture condition after inoculating human umbilical cord blood derived mesenchymal stem cells at a density of 20,000 cells in the same culture vessel was 38.991 µg/ml, which was 94% more improved protein content than the former (FIG. 22).

According to the above result, it could be confirmed that the optimal serum-free culture conditions that can maximize the secreted protein content from human mesenchymal stem cells established through the present invention can be applied not only human amniotic fluid-derived mesenchymal stem cells but also human umbilical cord blood derived mesenchymal stem cells.

Example 16. Validation of Optimal Serum-Free Culture Conditions in Amniotic Membrane-Derived Mesenchymal Stem Cell Conditioned Medium In order to confirm that the optimal serum-free culture conditions of the present invention are applicable to other tissue-derived mesenchymal stem cells, the total protein contents present in the stem cell conditioned medium obtained by culturing the human amniotic membrane-derived mesenchymal stem cells (Human Amniotic Mesenchymal Stem Cell, SCIENCELL, Cat. #7501) in two serum-free culture conditions was examined by BCA measurement method and compared as the same manner as in Example 5.

The existing conditioned medium means conditioned medium mixed with stem cell conditioned medium obtained at 72 hours, 144 hours, and 216 hours respectively after inoculating amniotic membrane-derived mesenchymal stem cells at a density of 10,000 cells/cm$^2$ in a culture vessel and serum-free culture, and the new conditioned medium means conditioned medium mixed with stem cell conditioned medium obtained at 120 hours, 240 hours, and 360 hours respectively after inoculating at a density of 20,000 cell/cm$^2$ in a culture vessel and serum-free culture.

As a result, the total protein content present in the conditioned medium mixed with stem cell conditioned medium obtained at 72 hours, 144 hours, and 216 hours respectively under serum-free culture condition after inoculating human amniotic membrane-derived mesenchymal stem cells at a density of 10,000 cells in the culture vessel was 27.269 µg/d. And the total protein content present in the conditioned medium mixed with stem cell conditioned medium obtained at 120 hours, 240 hours, and 360 hours respectively under serum-free culture condition after inoculating at a density of 20,000 cells/cm² in the same culture vessel was 48.379 µg/ml, which was 77% more improved protein content than the former (FIG. 23).

According to the above results, it could be confirmed that the optimal serum-free culture conditions that can maximize the secreted protein content from human mesenchymal stem cells established through the present invention can be applied not only human amniotic fluid-derived mesenchymal stem cells but also human amniotic membrane-derived mesenchymal stem cells.

When combined the above results, the optimal serum-free culture condition established in the present invention is the method for mass-production of the mesenchymal stem cell derived proteins, and is applicable to not only amniotic fluid-derived mesenchymal stem cells but also adipose-derived, bone marrow-derived, umbilical cord blood-derived and amniotic membrane-derived mesenchymal stem cells. So, it can be applied for all mesenchymal stem cells regardless of their origin, and mesenchymal stem cell conditioned medium obtained by this method can be used for a composition for skin regeneration or wrinkle improvement because it contains large quantities of various growth factors and cytokines.

From the above description, those skilled in the technical field to which the present invention belongs will appreciate that the present invention may be practiced in other specific forms without changing the technical idea and essential features thereof. In this regard, it should be understood that the above-described embodiments are illustrative in all aspects and not restrictive. The scope of the present invention rather than the above detailed description, was all changed or modified forms derived from meaning and scope of claims and their equivalent concepts of the claims to be described later should be interpreted as being included in the scope of the present invention

The invention claimed is:

1. A method for mass producing a mesenchymal stem cell-derived protein, the method comprising:
   (A) storing mesenchymal stem cells in a cryopreservation medium solution at a temperature of −80° C.;
   (B) inoculating the mesenchymal stem cells at a density of 20,000 cells/cm²;
   (C) culturing the mesenchymal stem cells in a serum-free medium;
   (D) obtaining a stem cell conditioned medium containing the protein produced by the mesenchymal stem cells after 120 hours of culture; and
   (E) extracting the mesenchymal stem cell-derived protein from the obtained stem cell conditioned medium,
   wherein a total concentration of the extracted protein is 30 µg/ml to 70 µg/ml, and
   wherein said protein is selected from the group consisting of AR, bFGF, BMP-5, BMP-7, GH, IGFBP-1, IGFBP-2, IGFBP-3, IGFBP-4, SCF, TGF α, TGF β1, VEGF R3, VEGF-D, ICAM-1, IL-1a, IL-5, MIP-1a, MIP-b, MIP-d, RANTES, TNF R1, TNF RII, BDNF, BMP-4, b-NGF, EGF R, FGF-4, FGF-7, GDF-15, GDNF, HGF, IGFBP-6, IGF-I, Insulin, MCSF R, NGF R, NT-3, NT-4, OPG, PDGF-AA, PIGF, SCF R, VEGF, G-CSF, IL-2, IL-6, IL-8, IL-11, MCP-1, MCSF, MIG, TIMP-1, TIMP-2, TNFα, and TNFβ, or a combination thereof.

2. The method of claim 1, wherein the mesenchymal stem cells are mesenchymal stem cells derived from amniotic fluid, fat, bone marrow, umbilical cord blood, or amniotic membrane.

3. The method of claim 1, wherein the mesenchymal stem cells are amniotic fluid-derived mesenchymal stem cells.

4. The method of claim 1, wherein the step (D) of obtaining the stem cell condition medium further comprises obtaining the stem cell conditioned medium an additional one to three times at intervals of 114 to 126 hours.

* * * * *